US 7,588,774 B2

(12) United States Patent
Campbell et al.

(10) Patent No.: US 7,588,774 B2
(45) Date of Patent: Sep. 15, 2009

(54) MOLECULES ENHANCING DERMAL DELIVERY OF INFLUENZA VACCINES

(75) Inventors: Robert L. Campbell, Bahama, NC (US); Kevin G. Dolan, Holly Springs, NC (US); Wendy D. Woodley, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 64 days.

(21) Appl. No.: 11/006,422

(22) Filed: Dec. 6, 2004

(65) Prior Publication Data

US 2005/0255121 A1 Nov. 17, 2005

Related U.S. Application Data

(63) Continuation-in-part of application No. 10/842,922, filed on May 10, 2004.

(60) Provisional application No. 60/470,243, filed on May 12, 2003.

(51) Int. Cl.
*A61K 39/00* (2006.01)
*A61K 39/39* (2006.01)
*A61K 39/12* (2006.01)
*A61K 39/02* (2006.01)

(52) U.S. Cl. .............. 424/280.1; 424/184.1; 424/204.1; 424/234.1; 424/265.1; 424/269.1; 424/274.1; 424/278.1; 514/28; 514/57

(58) Field of Classification Search .................. None
See application file for complete search history.

(56) References Cited

U.S. PATENT DOCUMENTS 4,826,687 A 5/1989 Nerome et al.

5,292,506 A 3/1994 Oki et al.

(Continued)

FOREIGN PATENT DOCUMENTS

EP 1 092 444 A1 4/2001

(Continued)

OTHER PUBLICATIONS

England, JL "Stabilization and Release Effects of Pluronic F127 in Protein Drug Delivery" Journal of Undergraduate Research (1999) 5(2): 17-24.*

(Continued)

*Primary Examiner*—Mary E Mosher
*Assistant Examiner*—Stuart W Snyder
(74) *Attorney, Agent, or Firm*—Alston & Bird LLP

(57) ABSTRACT

The present invention relates to dermal vaccine formulations, designed for targeted delivery of an immunogenic composition to a dermal compartment of skin including the intradermal and epidermal compartments. The dermal vaccine formulations of the invention comprise an antigenic or immunogenic agent, and at least one molecule, e.g., a chemical agent, which enhances the presentation and/or availability of the antigenic or immunogenic agent to the immune cells of the intradermal compartment or epidermal compartment resulting in an enhanced immune response. The dermal vaccine formulations of the invention have enhanced efficacy as the antigenic or immunogenic agent is delivered to the intradermal compartment or epidermal compartment with enhanced presentation and/or availability to the immune cells that reside therein. The enhanced efficacy of the dermal vaccine formulations results in a therapeutically effective immune response after a single intradermal or epidermal dose, with lower doses of antigenic or immunogenic agent than conventionally used, and without the need for booster immunizations.

29 Claims, 25 Drawing Sheets

U.S. PATENT DOCUMENTS

| | | | |
|---|---|---|---|
| 5,702,717 | A | 12/1997 | Cha et al. |
| 5,861,174 | A | 1/1999 | Stratton et al. |
| 5,912,000 | A | 6/1999 | Podolski et al. |
| 6,136,606 | A | 10/2000 | Chatfield |
| 6,316,011 | B1 * | 11/2001 | Ron et al. .................... 424/401 |
| 6,372,223 | B1 | 4/2002 | Kistner et al. |
| 6,485,729 | B1 | 11/2002 | Smith et al. |
| 6,494,865 | B1 | 12/2002 | Alchas |
| 6,534,065 | B1 | 3/2003 | Makin et al. |
| 7,258,873 | B2 * | 8/2007 | Truong-Le et al. ........... 424/489 |
| 2002/0025326 | A1 * | 2/2002 | Blonder et al. ............ 424/207.1 |
| 2005/0123550 | A1 | 6/2005 | Laurent et al. |
| 2005/0281832 | A1 * | 12/2005 | Campbell et al. ......... 424/184.1 |

FOREIGN PATENT DOCUMENTS

| | | |
|---|---|---|
| EP | 1250159 | 3/2005 |
| WO | WO 97/74323 | 12/1997 |
| WO | WO 98/42374 | 10/1998 |
| WO | WO 98/42375 | 10/1998 |
| WO | WO 00/50078 | 8/2000 |
| WO | WO 01/34801 A2 | 5/2001 |
| WO | WO 01/35994 | 5/2001 |
| WO | WO 01/54737 | 8/2001 |
| WO | WO 01/83698 | 11/2001 |
| WO | WO 01/98206 | 12/2001 |
| WO | WO 02/00173 | 1/2002 |
| WO | WO 02/25326 | 2/2002 |
| WO | WO 02/28426 | 4/2002 |
| WO | WO 02/062321 | 8/2002 |
| WO | WO 02/067983 | 9/2002 |
| WO | WO 02/074244 A3 | 9/2002 |
| WO | WO 02/074336 | 9/2002 |
| WO | WO 02/087494 A3 | 11/2002 |
| WO | WO 03/026621 | 4/2003 |

OTHER PUBLICATIONS

Hubert, P et al. "Delivery of Granulocyte-Macrophage Colony-Stimulating Factor in Bioadhesive Hydrogel Stimulates Migration of Dendritic Cells in Models of Human Papillomavirus-Associated (Pre)Neoplastic Epithelial Lesions" Antimicrob Agent Chemother (2004) 48(11):4342-4348.*
Preis I and RS Langer. A single-step immunization by sustained antigen release. J. Immunol Meth. 1979. 28(1-2):193-197.*
Wang P-L and TP Johnston. Sustained-release interleukin-2 following intramuscular injection in rats. Int J Pharmaceutics. 1995 113(1-2):73-81.*
Nam, et al. Lysozume Microencapsulation Within Biodegradable PLGA Microspheres: Urea Effect on Protein Release and Stability. Biotech. Bioeng. 2000 70(3):270-277.*
Westerink, et al. ProJuvant(Tm) (Pluronic F127(R)/chitosan) wnhances the immune response to intranasally administered tetanus toxoid. Vaccine, 2002; 85:711-723.*
Bentley, et al. The influence of lecithin and urea on the in vitro permeation of hydrocortisone acetate through skin from hairless mouse. International Journal of Pharmaceutics 146 (1997) 255 262.*
Wilkinson, et al. IgG antibodies and early intradermal reactions to hydrocortisone in patients with cutaneous delayed-type hypersensitivity to hydrocortisone. British journal of dermatology. 1994; 131(4): 495-498. Abstract Only.*
Hunter, et al. The Adjuvant Activity Of Nonionic Block Polymer Surfactants: 1. The Role of Hydrophile- Lipophile Balance. The Journal Of Immunology. 1981; vol. 127, No. 3. 1244-1250.*
Morgan, et al. Production and characterization of monoclonal antibody to a melanoma specific glycoprotein. Hybridoma. 1981, 1(1) p. 27-36. Abstract Only.*
U.S. Appl. No. 11/006,686, filed Dec. 6, 2004, Campbell.
"Flu vaccine: skin injection method effective in younger people," *American Health Line: Research Notes* (Nov. 4, 2004).

Alpar et al., "Intranasal vaccination against plague, tetanus and diphtheria," *Advanced Drug Delivery Reviews* 51:173-201 (2001).
Baldrick, 2000, "Pharmaceutical excipient development: The need for preclinical guidance," Regulatory Toxicology Pharmacol. 32:210-218.
Belshe et al., "Serum antibody response after intradermal vaccination against influenza," New England Journal of Medicine 351(22):2286-2294 (2004).
Blonder et al., 1999, "Dose-dependent hyperlipidemia in rabbits following administration of poloxamer 407 gel," Life Sci. 65(21):PL261-266.
Branswell, "Vaccine stretching may be an option for future shortages, pandemics: studies," *Canadian Press News Wire* (Nov. 3, 2004).
Chin et al., 1996, "Manipulating systemic and mucosal immune responses with skin-deliverable adjuvants," J. Biotechnol. 44:13-19.
Chin et al., 1993, "Manipulating mucosal immune response by intradermal immunization," J. Cell Biochem. Supp. 17C:54, Abstract HZ 111.
Chin et al., 1992, "Relationship between the immune response of sheep and the population dynamics of bacteria isolated from fleecerot lesions," Veterinary Microbiology 32:63-74.
Christodoulides et al., "Effect of adjuvant composition on immune response to a multiple antigen peptide (MAP) containing a protective epitope from *Neisseria meningitidis* class 1 porin," *Vaccine* 18:131-139 (2000).
Coeshott et al., 2001, "A novel adjuvant formulation containing a block copolymer with reverse gelation characteristics elicits long lasting IgG antibody responses after a single injection in mice," Abstracts of Submitted Papers, Fourth Ann. Conference Abstract S26.
Couvreur et al., "Multiple emulsion technology for the design of microspheres containing peptides and oligopeptides," *Advanced Drug Delivery Review* 28:85-96 (1997).
De Souza et al., "A novel adjuvant for use with a blood-stage malaria vaccine," *Vaccine* 13(14):1316-1319 (1995).
De Souza et al., "Cytokines and antibody subclass associated with protective immunity against blood-stage malaria in mice vaccinated with the C terminus of merozoite surface protein 1 plus a novel adjuvant," *Infection and Immunity* 64(9):3532-3536 (1996).
Fjerstad, "U. Minnesota professor uses alternative flu vaccine technique," *FSView & Florida Flambeau via U-Wire* (Nov. 15, 2004).
Haas et al., 2002, "Developments in the area of bioadhesive drug delivery systems," Expert Opin. Biol. Ther, 2(3):287-298.
Hunter et al., 1981, "The adjuvant activity on nonionic block polymer surfactants. I. The role of hydrophile-lipophile balance," J. Immunol. 127(3):1244-1250.
Hunter et al., 1984, "The adjuvant activity of nonionic block polymer surfactants. II Antibody formation and inflammation related to the structure of triblock and octablock copolymers," J. Immunol. 133(6):3167-3175.
Hunter et al., 1986, "The adjuvant activity of nonionic block polymer surfactants. III. Characterization of selected biologically active surfactants," Scand. J. Immunol. 23(3):287-300.
Hunter et al., 1991, "Adjuvant activity of nonionic block copolymers. IV. Effect of molecular weight and formulation of titer and isotype of antibody," Vaccine 9:250-256.
Hunter et al., 1994, "Mechanisms of action of nonionic block copolymer adjuvants," AIDS Res. Hum. Retroviruses 10(Supp. 2):S95-98.
Hunter et al., 1995, "Copolymer adjuvant and titermax," in DES Stewart-Tull (ed.), The Theory and Practical Application of Adjuvants, John Wiley and Sons, New York pp. 51-94.
Iida et al., 1987, "Stimulation of non-specific host resistance against Sendai virus and *E. coli* infections by chitin derivatives in mice," 5(4):270-274.
Illum, 1998, "Chitosan and its use as a pharmaceutical excipient," Pharmaceutical Res. 15(9):1326-1331.
Jabbal-Gill et al., "Stimulation of mucosal and systemic antibody responses against *Bordetella pertussis* filamentous haemagglutinin and recombinant pertussis toxin after nasal administration with chitosan in mice," Vaccine 16(20):2039-2046 (1998).
Kabanov et al., "Pluronic® block copolymers: novel functional molecules for gene therapy," Advanced Drug Delivery Reviews 54:223-233 (2002).

Katz et al., 2000, "A nonionic block co-polymer adjuvant (CRL1005) enhances the immunogenicity and protective efficacy of inactivated influenza vaccine in young and aged mice," Vaccine 18(21):2177-2187.

Ke et al., 1997, "Nonionic triblock copolymers facilitate delivery of exogenous proteins into the MHC class I and class II processing pathways," Cell Immunol. 176(2):113-121.

Kenney et al., "Dose sparing with intradermal injection of influenza vaccine," New England Journal of Medicine 351(22):2295-2301 (2004).

Kidane et al., "Effects of cellulose derivatives and poly(ethylene oxide)—poly(propylene oxide) tri-block copolymers (Pluronic® surfactants) on the properties of alginate based microspheres and their interactions with phagocytic cells," Journal of Controlled Release 85:181-189 (2002).

Kim et al., "Temperature-responsive and degradable hyaluronic acid/pluronic composite hydrogels for controlled release of human growth hormone," Journal of Controlled Release 80:69-77 (2002).

Knox et al. "New research shows intradermal rather than intramuscular vaccine injection could stretch flu vaccine supplies," *National Public Radio: All Things Considered* (Nov. 3, 2004).

Kohn, "Flu shot technique yields more doses, studies find; critics say injecting skin rather than muscle is too difficult for common use," *The Baltimore Sun: Telegraph 3A* (Nov. 4, 2004).

Lanier et al., 1999, "Peptide vaccination using nonionic block copolymers induces protective anti-viral CTL responses," Vaccine 18(5-6):549-557.

Majeski et al., "Technique could stretch vaccine; changing the way shots are given means the current supply of flu vaccine could immunize 10 times as many people, two Minnesota physicians say" Saint Paul Pioneer Press: Main 1A (Oct. 27, 2004).

Majeski, "Alternate flu shot less effective in elderly; doctors proposed method to stretch vaccine supply," *Saint Paul Pioneer Press: Main* 17A (Nov. 4, 2004).

McNeela et al., "Manipulating the immune system: humoral versus cell-mediated immunity," *Advanced Drug Delivery Reviews* 51:43-54 (2001).

Moghimi et al., "Poloxamers and poloxamines in nanoparticle engineering and experimental medicine," *Tibtech* 18:412-420 (2000).

Moghimi et al., 1996, "Poloxamer-188 revisited: a potentially valuable immune modulator," J. Natl. Cancer Inst. 88(11):766-768.

Montagne et al., "Intradermal influenza vaccination—can less be more?" New England Journal of Medicine 351(22):2330-2332 (2004).

Murillo et al., "Modulation of the cellular immune response after oral or subcutaneous immunization with microparticles containing *Brucella ovis* antigens," *Journal of Controlled Release* 85:237-246 (2002).

Newman et al., 1998, "Design and development of adjuvant-active nonionic block copolymers," J. Pharm. Sci. 87(11):1357-1362.

Newman et al., 1998, Development of adjuvant-active nonionic block copolymers, Adv. Drug Deliv. Rev. 32(3):199-223.

Newman et al., 1998, "Use of nonionic block copolymers in vaccines and therapeutics," Crit. Rev. Ther. Drug Carrier Syst. 15(2):89-142.

Newman et al., 1997, "Increasing the immunogenicity of a trivalent influenza vaccine with adjuvant active nonionic block copolymers for potential use in elderly," Mech. Ageing Dev. 93:189-203.

Nishimura et al., 1984, "Immunological activity of chitin and its derivatives," Vaccine 2:93-99.

Peppas et al., 1996, "Hydrogels as mucoadhesive and bioadhesive materials: a review," Biomaterials 17(16):1553-1561.

Rindfleisch et al., "La Crosse finding could curtail flu vaccine shortages," *Wisconsin State Journal* D9 (Nov. 14, 2004).

Robinson et al., 1987, "Bioadhesive polymers for controlled drug delivery," Ann NY Acad. Sci. 507:307-314.

Ryan et al., "Immunomodulators and delivery systems for vaccination by mucosal routes," *Trends in Biotechnology* 19(8)293-304 (2001).

Seferian et al., "Immune stimulating activity of two new chitosan containing adjuvant formulations," *Vaccine* 19:661-668 (2001).

Singla et al., 2001, "Chitosan: Some pharmaceutical and biological aspects—an update," J. Pharmacy and Pharmacol. 53:1047-1067.

Smith, "Low-dose vaccine helps block flu, study says younger adults seen benefiting," *The Boston Globe: National/Foreign* A2 (Nov. 4, 2004).

Takayama et al., 1991, "Adjuvant activity of non-ionic block copolymers. V. Modulation of antibody isotype by lipopolysaccharides, lipid A and precursors," Vaccine 9(4):257-265.

Todd et al., 1997, "Development of an adjuvant active nonionic block copolymer for use in oil-free subunit vaccines formulation," Vaccine 15:564-570.

Todd et al., 1998, Systematic development of a block copolymer adjuvant for trivalent influenza virus.

Shute, "Second thoughts on the flu vaccine," *Science & Society: Public Health* 137(17):80, 2004.

Van Der Lubben et al., "Chitosan and its derivatives in mucosal drug and vaccine delivery," *European Journal of Pharmaceutical Sciences* 14:201-207 (2001).

Van Der Lubben et al., "Chitosan for mucosal vaccination," *Advanced Drug Delivery Reviews* 52:139-144 (2001).

Verheul et al., 1992, "Nonionic block polymer surfactants as immunological adjuvants," Res. Immunol. 143(5):512-519, discussion pp. 574-576.

Vogel et al., 1995, "A compendium of vaccine adjuvants and excipients," in M.F. Powell, M.J. Newman (eds.) Plenum Press, New York pp. 141-228.

Von Hoegen, "Synthetic biomimetic supra molecular Biovector™ (SMBV™) particles for nasal vaccine delivery," *Advanced Drug Delivery Reviews* 51:113-125 (2001).

Westerink et al., "ProJuvant™ (Pluronic F127®/chitosan) enhances the immune response to intranasally administered tetanus toxoid," *Vaccine* 20:711-723 (2002).

Woodley, 2001, "Bioadhesion: New possibilities for drug administration?" Clin. Pharmacokinet. 40(2):77-84.

Zigterman et al., 1987, "Adjuvant effects of nonionic block polymer surfactants on liposome-induced humoral immune response," J. Immunol. 138(1):220-225.

Zhang, L., et al., "Development and In-Vitro Evaluation of Sustained Release Poloxamer 407 (P407) Gel Formulations of Ceftiofur," *Journal of Controlled Release*, 2002, pp. 73-81, vol. 85.

Halperin, W., et al., "A Comparison of the Interadermal and Subcutaneous Routes of Influenza Vaccination with A/New Jersey/76 (Swine Flu) and A/Victoria/75: Report of a Study and Review of the Literature," *Am. J. of Public Health*, 1979, pp. 1247-1250, vol. 69(12).

Nakayama, T., et al., "A Clinical Analysis of Gelatin Allergy and Determination of its Causal Relationship to the Previous Administration of Gelatin-Containing Acellular Pertussis Vaccine Combined With Diphtheria and Tetanus Toxoids," 1999, *J. Allergy Clin. Immunol.*, pp. 321-325, vol. 103(2)(1).

* cited by examiner

Draize Scoring — Swine model

Saline – negative control

| Time | Erythema | | |
|---|---|---|---|
| 1 hour | 0 | 1 | 0 |
| 6 hours | 0 | 1 | 0 |
| 24 hours | 0 | 1+ | 0 |

0.18% (w/v) methylcellulose (test substance)

| Time | Erythema | | |
|---|---|---|---|
| 1 hour | 1 | 1 | 1 |
| 6 hours | 0 | 0 | 0 |
| 24 hours | 0 | 0 | 0 |

Influenza immunogen

| Time | Erythema | | |
|---|---|---|---|
| 1 hour | 2 | 2 | 2+ |
| 6 hours | 1+ | 1+ | 2 |
| 24 hours | 1 | 0 | 1 |

Influenza immunogen + 0.18% (w/v) methylcellulose (test substance)

| Time | Erythema | | |
|---|---|---|---|
| 1 hour | 2 | 1+ | 2 |
| 6 hours | 1 | 0 | 1 |
| 24 hours | 1 | 0 | 0 |

Draize score scale
- No erythema — 0
- Very slight erythema — 1
- Well defined erythema — 2
- Moderate to severe erythema — 3
- Severe erythema (beet redness injury to depth) — 4

FIG. 7

A.
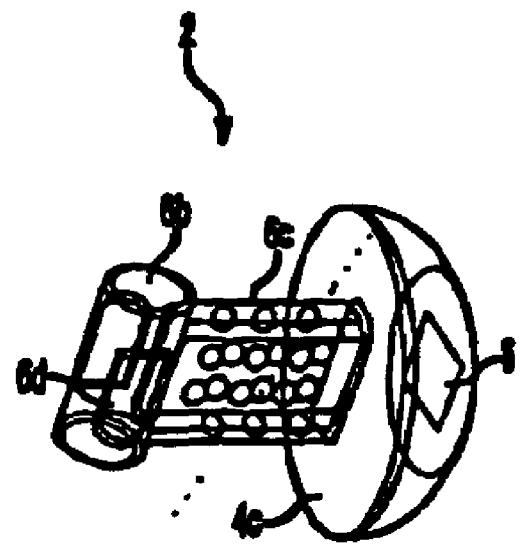
B.
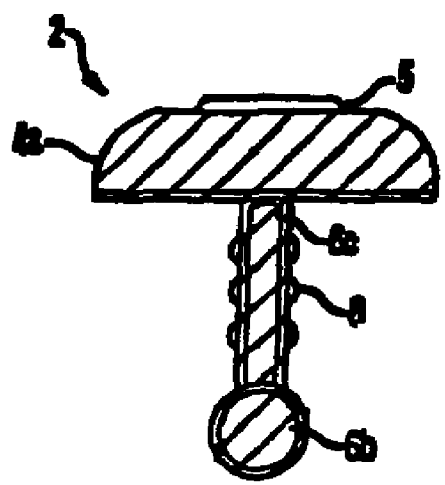
FIG. 12

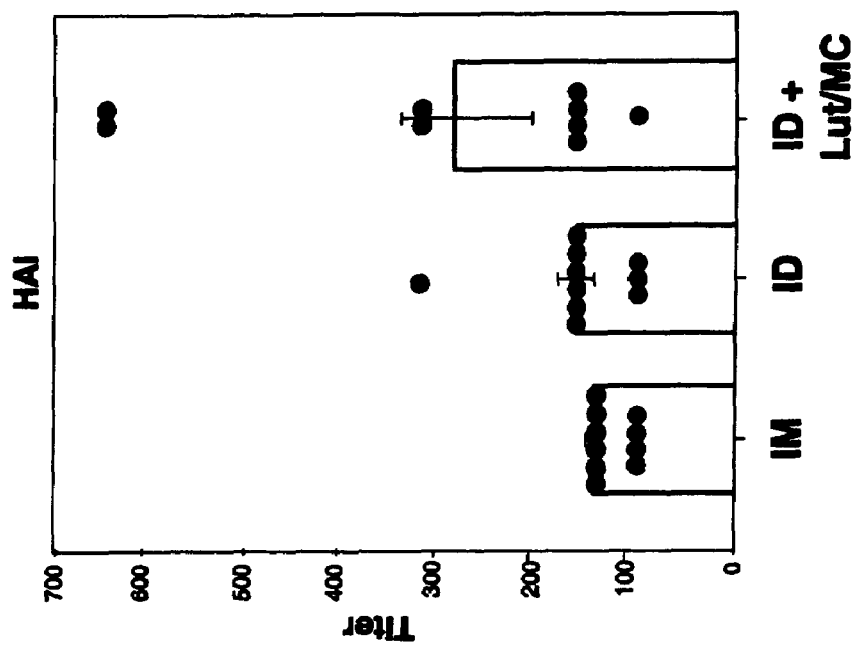
Figure 17: Comparison of Fluzone vaccine alone, IM and ID, vs reformulated Fluzone vaccine with Lutrol 5% + Methylcellulose 0.18% in Guinea pigs by HAI assay (Trivalent cocktail)

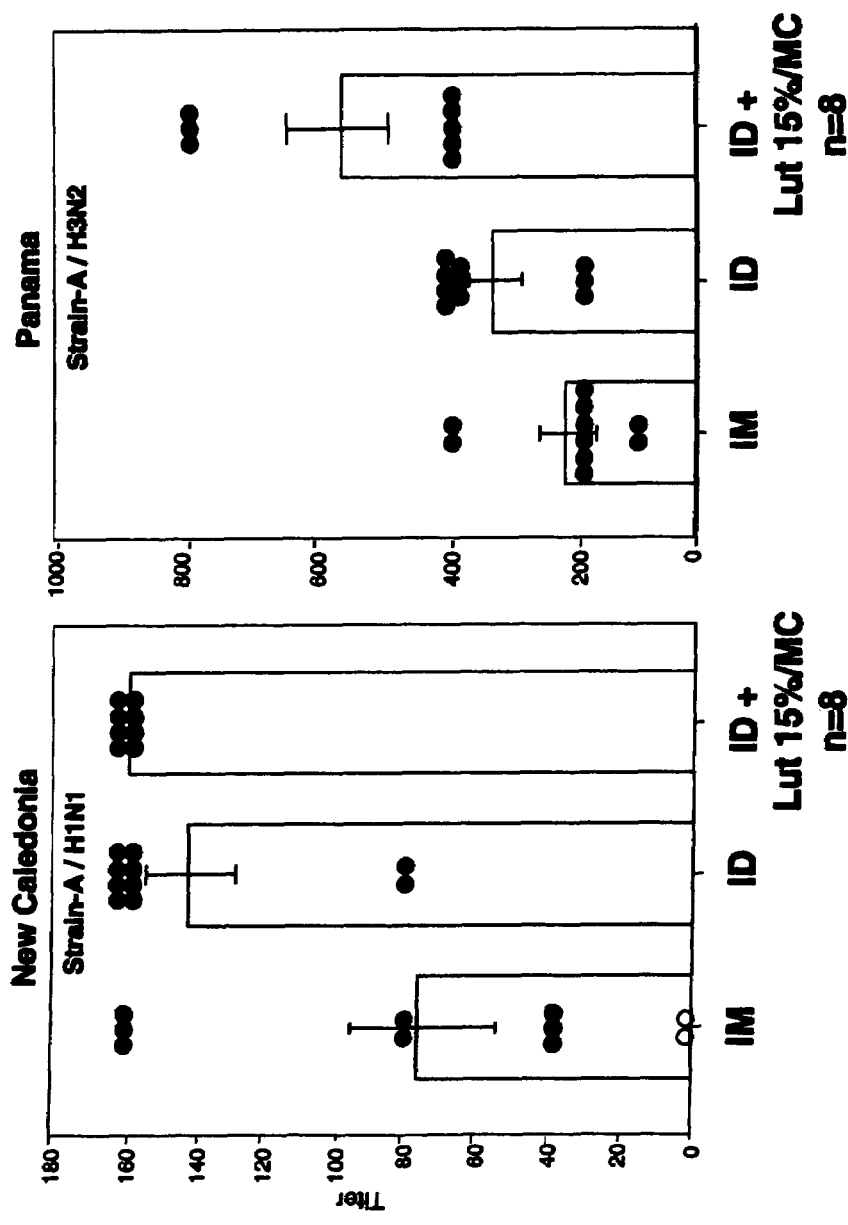
Figure 18: Comparison of IM and ID delivery of Fluzone vaccine alone vs. ID delivery of reformulated Fluzone vaccine (Lutrol 15% + Methylcellulose 0.18%) in Balb/C mice by HAI assay (H1N1 and H3N2 strains)

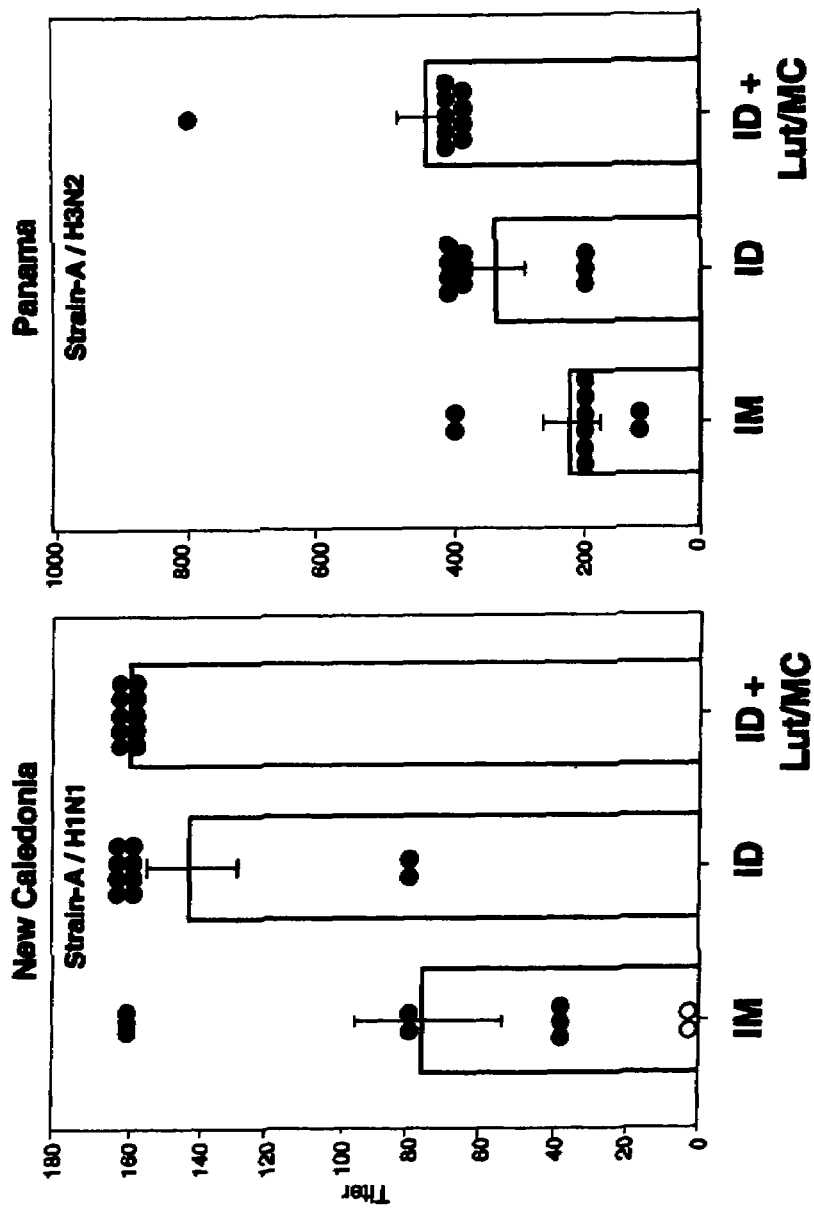
Figure 19: Comparison of IM and ID delivery of Fluzone vaccine alone vs. ID delivery of reformulated Fluzone vaccine (Lutrol 5% + Methylcellulose 0.18%) in BalbC mice by HAI assay (H1N1 and H3N2 strains)

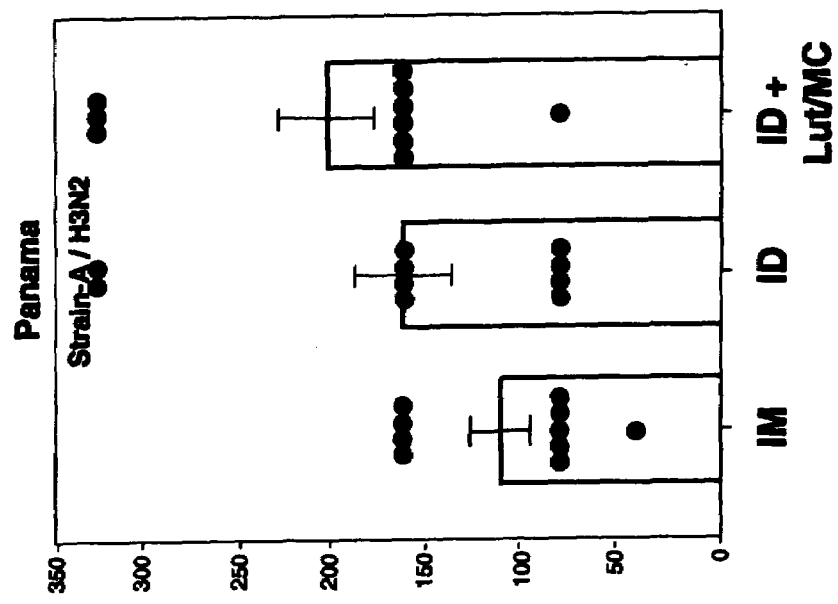
Figure 20: Comparison of IM and ID delivery of Fluzone vaccine alone vs ID delivery of reformulated Fluzone vaccine (Lutrol 5% + Methylcellulose 0.18%) in Guinea pigs by HAI assay (H3N2 strain)

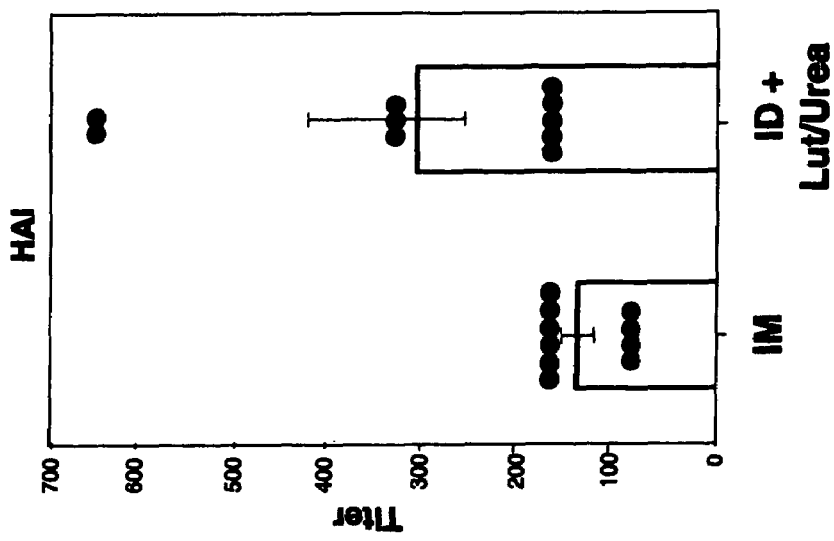
Figure 21 Comparison of IM delivery of Fluzone vaccine alone vs ID delivery of reformulated Fluzone vaccine (Lutrol 5% + Urea 0.2%) in Guinea pigs by HAI assay (Trivalent cocktail)

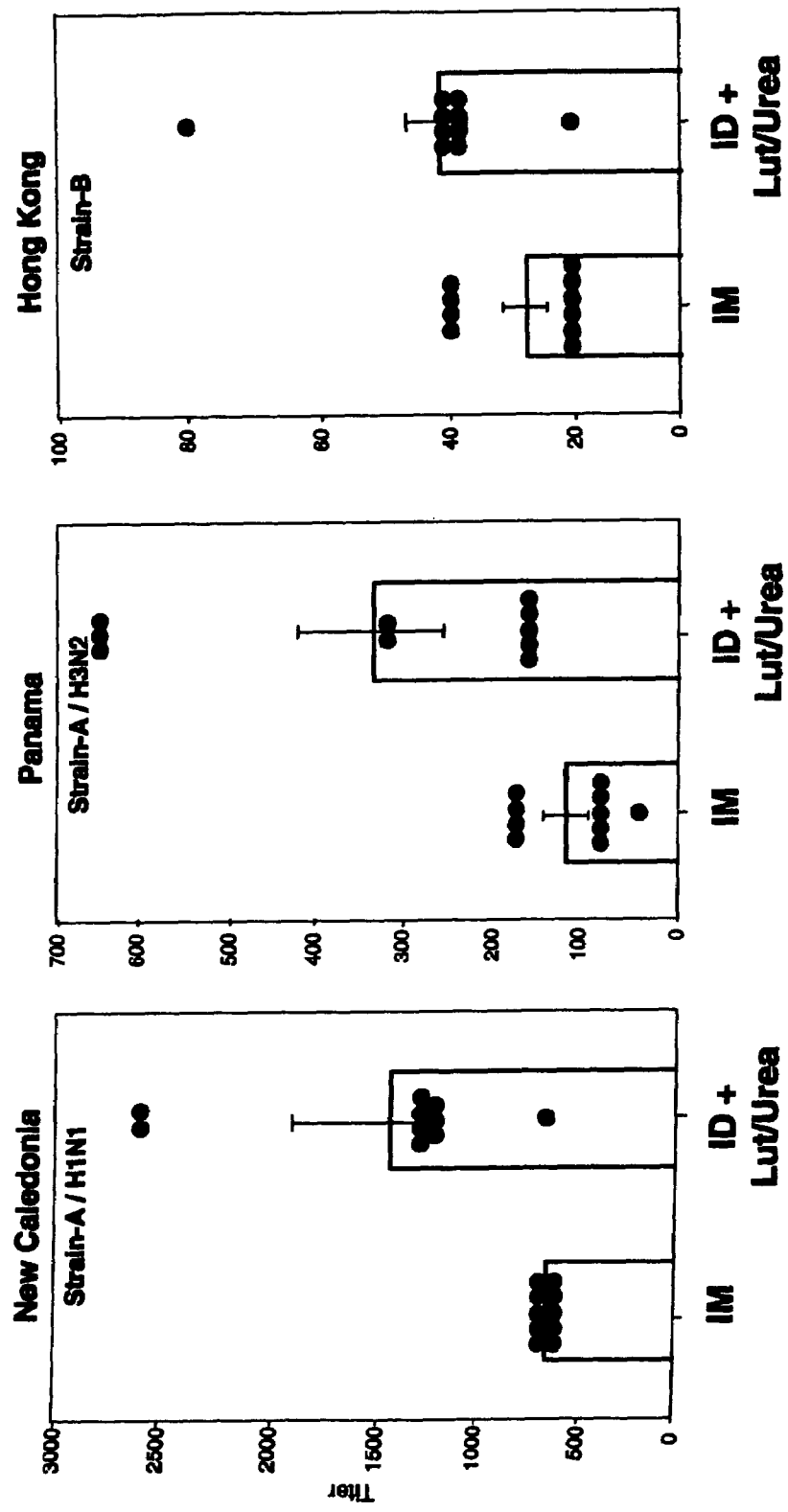
Figure 22: Comparison of IM delivery of Fluzone vaccine alone vs ID delivery of reformulated Fluzone vaccine (Lutrol 5% + Urea 0.2%) in Guinea pigs by HAI assay (H1N1, H3N2 and Hong Kong B-strain strains)

Figure 23: Comparison of IM and ID delivery of Fluzone vaccine alone vs ID delivery of reformulated Fluzone vaccine (Gelatin 0.225% + Methylcellulose 0.18%) in Guinea pigs by HAI assay (Trivalent cocktail)

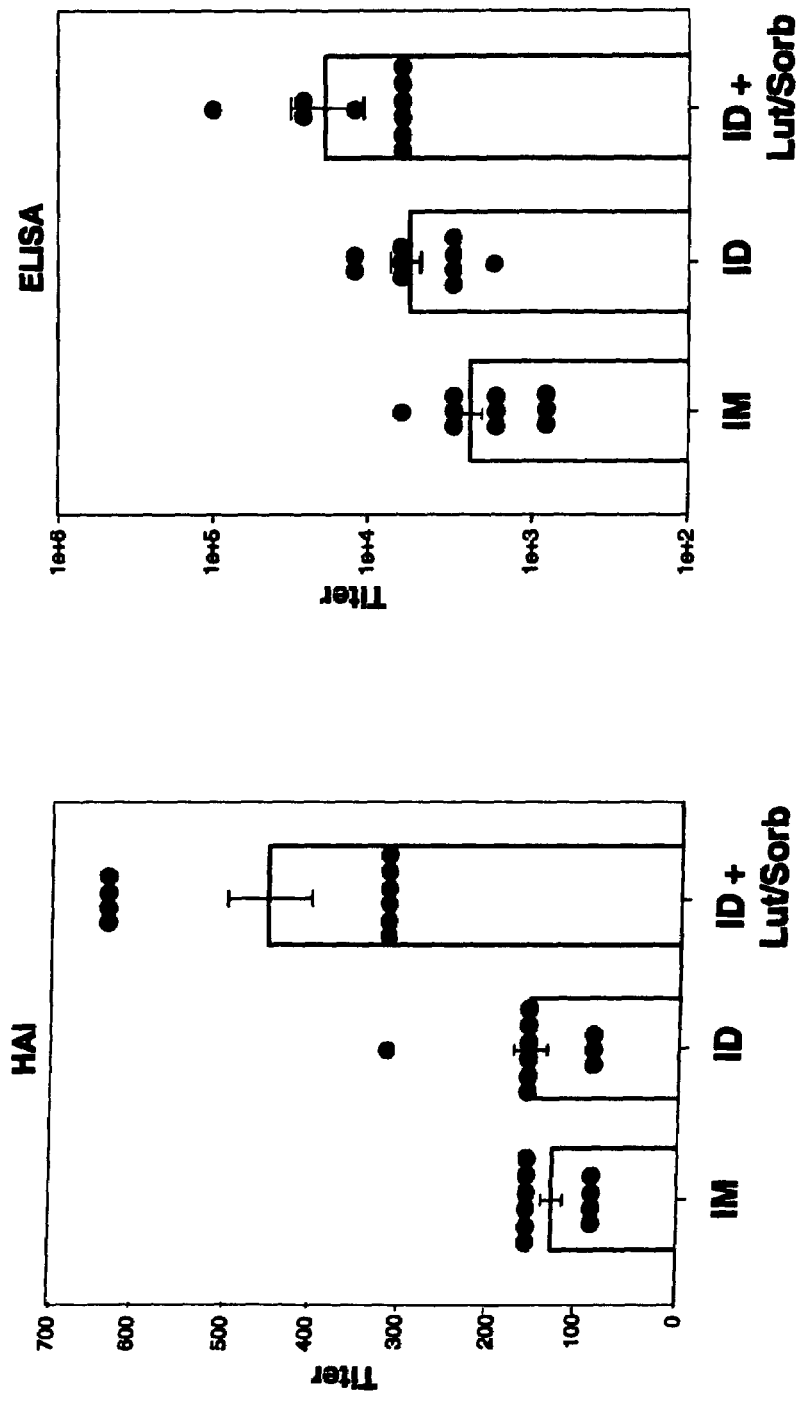
Figure 24: Comparison of IM and ID delivery of Fluzone vaccine alone vs ID delivery of reformulated Fluzone vaccine (Lutrol 5% + D-Sorbitol 5%) in Guinea pigs by HAI assay (Trivalent cocktail) and ELISA (Trivalent cocktail)

MOLECULES ENHANCING DERMAL DELIVERY OF INFLUENZA VACCINES

This application is a continuation-in-part application of U.S. application Ser. No. 10/842,922 filed on May 10, 2004 which claims priority to U.S. provisional application No. 60/470,243, filed May 12, 2003, each of which is incorporated herein by reference in its entirety.

1. FIELD OF THE INVENTION

The present invention relates to dermal vaccine formulations, designed for targeted delivery of an immunogenic composition to a dermal compartment of skin including the intradermal and epidermal compartments. The immunogenic compositions of the invention comprise an antigenic or immunogenic agent, and two or more pre-selected excipients, two or more mucoadhesives, two or more bioadhesives, or two or more geling agents or any combination thereof, resulting in an enhanced immune response to the antigenic or immunogenic agent, when delivered to the dermal compartment. The dermal vaccine formulations of the invention have enhanced efficacy as the antigenic or immunogenic agent is delivered to the intradermal compartment or epidermal compartment with enhanced presentation and/or availability to the immune cells that reside therein. The enhanced efficacy of the dermal vaccine formulations results in a therapeutically effective immune response after a single intradermal or epidermal dose, with lower doses of antigenic or immunogenic agent than conventionally used, and without the need for booster immunizations.

2. BACKGROUND OF THE INVENTION

2.1 Vaccines

Vaccines have traditionally consisted of live attenuated pathogens, whole inactivated organisms or inactivated toxins. In many cases these approaches have been successful at inducing immune protection based on antibody mediated responses. However, certain pathogens, e.g., HIV, HCV, TB, and malaria, require the induction of cell-mediated immunity (CMI). Non-live vaccines have generally proven ineffective in producing CMI. In addition, although live vaccines may induce CMI, some live attenuated vaccines may cause disease in immunosuppressed subjects. As a result of these problems, several new approaches to vaccine development have emerged, such as recombinant protein subunits, synthetic peptides, protein polysaccharide conjugates, and plasmid DNA. While these new approaches may offer important safety advantages, a general problem is that vaccines alone are often poorly immunogenic. Therefore, there is a continuing need for the development of potent and safe adjuvants that can be used in vaccine formulations to enhance their immunogenicity. For a review of the state of the art in vaccine development see, e.g., Edelman, 2002, *Molecular Biotech.* 21: 129-148; O'Hagan et al., 2001, *Biomolecular Engineering,* 18: 69-85; Singh et al., 2002, *Pharm. Res.* 19(6):715-28)

Traditionally, the immunogenicity of a vaccine formulation has been improved by injecting it in a formulation that includes an adjuvant. Immunological adjuvants were initially described by Ramon (1924, *Ann. Inst. Pasteur,* 38: 1) "as substances used in combination with a specific antigen that produced a more robust immune response than the antigen alone". A wide variety of substances, both biological and synthetic, have been used as adjuvants. However, despite extensive evaluation of a large number of candidates over many years, the only adjuvants currently approved by the U.S. Food and Drug administration are aluminum-based minerals (generically called Alum). Alum has a debatable safety record (see, e.g., Malakoff, *Science,* 2000, 288: 1323), and comparative studies show that it is a weak adjuvant for antibody induction to protein subunits and a poor adjuvant for CMI. Moreover, Alum adjuvants can induce IgE antibody response and have been associated with allergic reactions in some subjects (see, e.g., Gupta et al., 1998, *Drug Deliv. Rev.* 32: 155-72; Relyveld et al., 1998, *Vaccine* 16: 1016-23). Many experimental adjuvants have advanced to clinical trials since the development of Alum, and some have demonstrated high potency but have proven too toxic for therapeutic use in humans. Further, while a particular adjuvant may prove to be safe and efficacious in one tissue, the same agent may perform poorly or be toxic in another tissue space. Accordingly, each agent must be reevaluated as new delivery devices allow clinicians to reach new tissue spaces.

The existing vaccine formulations are usually administered several times over a time span of months in order to elicit an immune response that can confer protection on the host upon subsequent encounter with the antigen, e.g., microbe, itself. Thus, although vaccines for a variety of infectious diseases are currently available, many of these, including those for influenza, tetanus, and hepatitis B, require more than one administration to confer a protective benefit. These limitations are extremely problematic in countries where healthcare is not readily available or accessible. Moreover, compliance is also a problem in developed countries, particularly for childhood immunization programs.

Therefore, there is clearly an unmet need for more effective vaccine formulations and more effective means of delivering them to result in an enhanced therapeutic efficacy and protective immune response. Specifically, there is a need to develop vaccine formulations that reduce or eliminate the need for prolonged injection regimens.

2.2 Influenza Vaccines

The influenza viruses are divided into types A, B and C based on antigenic differences. Influenza A viruses are described by a nomenclature which includes the sub-type or type, geographic origin, strain number, and year of isolation, for example, A/Beijing/353/89. There are at least 15 subtypes of HA (H1-H13) and nine sub-types of NA (N1-N9). All sub-types are found in birds, but only H1-H3 and N1-N2 are found in humans, swine and horses (Murphy and Webster, "Orthomyxoviruses", in *Virology*, ed. Fields, B. N., Knipe, D. M., Chanock, R. M., p. 1091-1152, Raven Press, New York, 1990). Influenza A and B virus epidemics can cause a significant mortality rate in older people and in patients with chronic illnesses.

Epidemic influenza occurs annually and is a cause of significant morbidity and mortality worldwide. Children have the highest attack rate and are largely responsible for transmission of influenza virus in the human community. The elderly and persons with underlying health problems, e.g., immuno-compromised individuals, are at an increased risk for complications and hospitalization from influenza infection. In the United States alone, more than 10,000 deaths occurred during each of the seven influenza seasons between 1956 and 1988 due to pneumonia and influenza, and greater than 40,000 deaths were reported for each of the two seasons (Update: Influenza Activity—United States and Worldwide, and Composition of the 1992-1993 Influenza Vaccine, Morbidity and Mortality Weekly Report. U.S. Department of Health and Human Services, Public Health Service, 41 No. 18:315-323, 1992). Typical influenza epidemics cause increases in incidence of pneumonia and lower respiratory disease, as witnessed by increased rates of hospitalization or mortality. The elderly or those with underlying chronic diseases are most likely to experience such complications, but young infants also may suffer severe disease. These groups, in particular, need to be protected.

Currently available influenza vaccines are either inactivated or live attenuated influenza vaccines. Inactivated flu vaccines comprise one of three types of antigen preparation: inactivated whole virus, sub-virions where purified virus particles are disrupted with detergents or other reagents to solubilise the lipid envelope (so-called "split" vaccine) or purified HA and NA (subunit vaccine). These inactivated vaccines are generally given intramuscularly (i.m.).

Influenza vaccines are usually trivalent vaccines. They generally contain antigens derived from two influenza A virus strains and one influenza B strain. A standard 0.5 mL injectable dose in most cases contains 15 µg of haemagglutinin antigen from each strain, as measured by single radial immunodiffusion (SRD) (Wood et al., 1977, *J. Biol. Stand.* 5: 237-247; Wood et al., 1981, *J. Biol. Stand.* 9: 317-330).

Current efforts to control the morbidity and mortality associated with yearly epidemics of influenza are based on the use of intramuscularly administered inactivated split or subunit influenza vaccines. The efficacy of such vaccines in preventing respiratory disease and influenza complications ranges from 75% in healthy adults to less than 50% in the elderly.

Therefore, there is clearly a need for an alternative way of administering influenza vaccines, in particular, a way that is pain-free or less painful than intramuscular injection, does not have the same risk of injection site infection, and does not involve the associated negative effect on patient compliance because of "needle fear". Furthermore, it would be desirable to administer an influenza vaccine via an administration route that does not have negative effects on the health care worker, such as high risk of needle stick injury. Additionally, there is still an unmet need for a more therapeutically effective influenza vaccine formulation that reduces or eliminates the need for a prolonged injection regimen. and additionally reduces any type of irritation, beit local or systemic.

3. SUMMARY OF THE INVENTION

The present invention is based, in part, on the surprising discovery by the inventors that delivering an antigenic or immunogenic agent in combination with a cocktail comprising a combination of two or more agents including but not limited to two or more pre-selected excipients, two or more mucoadhesives, two or more bioadhesives, or two or more geling agents or any combination thereof, results in an enhanced immune response to the antigenic or immunogenic agent, when delivered to the dermal compartment, including the epidermal and intradermal compartments. The enhanced efficacy of the compositions of the invention is based, in part, on the appreciation and recognition by the inventors that specific combinations of such agents, can act as adjuvants, resulting in an enhanced immune response to the antigenic or immunegic agent once delivered to the dermal compartment.

Without being limited by a particular theory, it is found that a combination of two or more agents synergistically or additively act to enhance the immunogenicity of the antigen or immunogen comprised in the compositions of the invention, resulting in an enhanced immune response to the antigen or immunogen. Preferably, the agent used in connection with this invention has not been previously associated with an enhanced immune response, particularly in the intradermal compartment. More preferably, the combination of two or more agents of the invention has not been previously associated with an enhanced immune response, particularly in the intradermal compartment, particularly at the dosages disclosed herein.

In some embodiments, the immunogenic compositions of the invention comprise an antigenic or immunogenic agent in combination with two or more mucoadhesives. In other embodiments, the immunogenic compositions of the invention comprise an antigenic or immunogenic agent in combination with two or more bioadhesives. In a specific embodiment, the muco or bioadhesive includes but is not limited to gelatin, methylcellulose, chitosan and carboxymethylcellulose.

In yet other embodiments, the immunogenic compositions of the invention comprise an antigenic or immunogenic agent in combination with at least two agents, wherein the first agent is a geling agent e.g., polymerizes or gels at a physiological temperature and the second agent is a mucoadhesive or bioadhesive. In a specific embodiment, the geling agent is LUTROL® and the mucoadhesive or bioadhesive includes but is not limited to gelatin, methylcellulose, chitosan and carboxymethylcellulose.

In yet other embodiments, the immunogenic compositions of the invention comprise an antigenic or immunogenic agent in combination of at least two agents, wherein the first agent is a geling agent and the second agent is a pre-selected excipient. In a specific embodiment the geling agent is LUTROL® and the excipient includes but is not limited to methylcellulose, gelatin, sorbitol, chitosan, and urea.

In yet other embodiments, the immunogenic compositions of the invention comprise an antigenic or immunogenic agent in combination of at least two agents, wherein the first agent is a muco or bioadhesive and the second agent is a muco or bioadhesive.

In another embodiment, the composition of the invention comprises an antigenic or immunogenic agent in combination of at least two agents, wherein the first agent is a muco or bioadhesive (e.g., gelatin, methylcellulose, LUTROL® ) and the second agent is a pre-selected excipient including but not limited to, LUTROL® , gelatin, sorbitol, chitosan, and urea.

The benefits of the invention are based, in part, on the appreciation and recognition by the inventors that the intradermal compartment provides an ideal immunological space for a direct access of the antigenic or immunogenic agent to the immune cells residing therein. Indeed, the intradermal compartment has rarely been effectively targeted as a site of delivery of an antigenic or immunogenic agent, at least, in part, due to the difficulty of a specific and reproducible delivery of the antigenic or immunogenic agent, i.e., the precise needle placement into the intradermal space and adequate pressures of delivery.

The benefits of the invention are also appreciated in other dermal compartments including but not limited to the epidermal compartment of skin since. Although not intending to be bound by any particular mechanism of action, the skin represents an attractive target site for delivery of vaccines and gene therapeutic agents. In the case of vaccines (both genetic and conventional), the skin is an attractive delivery site due to the high concentration of antigen presenting cells (APC) and APC precursors found within this tissue, especially the epidermal Langerhan's cells (LC) and the immune cells in the intradermal compartment.

The enhanced efficacy of the formulations of the inventions may be achieved with dermal vaccine formulations including formulations for intradermal and epidermal delivery. In some embodiments, the dermal vaccine formulations of the invention (including the epidermal and intradermal formulations) comprise an antigenic or immunogenic agent, and two or more agents, which enhances the presentation and/or availability of the antigenic or immunogenic agent to an immune cell, e.g., the immune cells of the intradermal compartment (e.g., antigen presenting cells) or the immune cells of the epidermal compartment (e.g., epidermal Langerhan's cells (LC)), resulting in an enhanced protective immune response. In a specific embodiment, the two or more agents acts to prolong the exposure of the antigenic or immunogenic agent to the immune cells of the dermal compartment, e.g., antigen presenting cells, epidermal Langerhan's cells (LC), resulting in an enhanced protective immune response.

The dermal vaccine formulations of the invention (including the epidermal and intradermal formulations) have enhanced efficacy, e.g., enhanced protective immune response, as the antigenic or immunogenic agent is delivered to the dermal compartment with an enhanced availability and/or presentation to the immune cells that reside therein, e.g., antigen presenting cells. Alternatively, the dermal vaccine formulations of the invention have enhanced efficacy as the antigenic or immunogenic agent is delivered to the dermal compartment, with a prolonged exposure of the antigenic or immunogenic agent to the immune cells that reside therein, resulting in an enhanced immune response. The enhanced efficacy of the dermal vaccine formulations (including the epidermal and dermal formulations) results in a therapeutically effective response, e.g., protective immune response, after a single dermal dose, with lower doses of the antigenic or immunogenic agent than conventionally used, and without the need for booster immunizations.

The geling agents that may be used in the compositions of the invention polymerize or gel once administered to the dermal space, creating a semi-solid to solid gelatinous matrix. In some embodiments, the gelatinous matrix allows for an enhanced presentation and/or interaction of the antigenic and/or immunogenic agent with the immune cells in the dermal space. In a specific embodiment, the geling agent is a polymer that polymerizes or gels once administered to the dermal space. Preferably, the polymers for use in the dermal vaccine formulations of the invention enhance the presentation and/or availability of the antigenic or immunogenic agent to the immune cells of the dermal compartment, e.g., antigen presenting cells.

Geling agents that may be used in the dermal vaccine formulations of the invention (including the epidermal and intradermal formulations) include polymers, preferably biocompatible and/or biodegradable polymers, which undergo a thermally induced physical transition from a liquid to a gel at a physiological temperature, e.g., a temperature ranging from 25° to 37° C. It will be appreciated by one skilled in the art, that the physiological temperature should be at a temperature above the liquid-gel transition of the polymer. Preferably, the polymer is a non-ionic block copolymer, also known as a PLURONIC® or Poloxamer, including, but not limited to, PLURONIC® F-127 (generically known as poloxamer 407), PLURONIC® F-68, and PLURONIC® F108. In some embodiments, the polymer acts as a depot. Alternatively, the polymer may enhance the presentation and/or availability of the antigenic or immunogenic agent to the immune cells of the dermal compartments, e.g., antigen presenting cells. In some embodiments, the polymer is an adjuvant. In yet other embodiments, the polymer is also a bioadhesive and/or a mucoadhesive. One advantage of the use of polymers in the intradermal vaccine formulations of the invention is that they are particularly well suited for intradermal delivery in that, at a temperature below the physiological temperature, e.g., a temperature ranging from 25° to 37° C., the intradermal vaccine formulation is a liquid, and after intradermal injection, the intradermal vaccine formulation forms a gel as it is warmed in the subject to a temperature above the liquid-gel transition temperature. In a specific embodiment, the gelatinous formulation may allow slow release of the antigenic or immunogenic agent in the dermis, potentiating an effective immune response. Furthermore, the intradermal vaccine delivery system of the invention is ideal for intradermal administration since the gelatinous material prevents any fluid leakage, thereby adding to an already established benefit of intradermal delivery.

In some embodiments, the muco or bioadhesive used in the dermal vaccine formulations of the invention may facilitate adherence of the antigenic or immunogenic agent to the cell surface of the immune cells of the dermal compartment. Examples of muco or bioadhesives that may be used in the dermal vaccine formulations of the invention include, but are not limited to, polycarbophils, polyacrylic acid (PAA), carobopols, Carbopol EX55, capricol, carbomers, polysaccharides, hyaluronic acid, chitosans; lectins; cellulose, methylcellulose, carboxymethylcellulose, hydroxypropyl methyl cellulose, sodium alginate, gelatin, pectin, acacia, and povidone. Although not intending to be bound by a particular mechanism of action, muco or bioadhesives enhance the presentation and/or availability of the antigenic or immunogenic agent to the immune cells of the dermal compartment. In some embodiments, the muco or bioadhesive may permit the antigenic or immunogenic agent to adhere to the immune cells of the dermal space, e.g., antigen presenting cells. In some embodiments, the invention encompasses an dermal vaccine formulation comprising an antigenic or immunogenic agent and at least two muco or bioadhesive molecules.

Excipients which may be used in the immunogenic compositions of the invention include, but are not limited to, stabilizers, preservatives, solvents, surfactants or detergents, suspending agents, tonicity agents, geling agents, muco/bioadhesives, vehicles and ingredients for growth medium. A non-limiting list of excipients that may be used in the immunogenic compositions of the invention are acetic acid, citric acid, fumaric acid, hydrochloric acid, nitric acid, sodium acetate, cellulose, charcoal, gelatin, ammonia solution, ammonium carbonate, mono-, di- or tri-ethanolamine, potassium hydroxide, sodium borate, sodium carbonate, sodium hydroxide, trolamine, nitrogen gas, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, sodium sulfite, glycine, potassium metaphosphate, potassium phosphate, monobasic sodium acetate, anhydrous or dihydrate sodium citrate, edetate disodium, edetic acid, glycerin, propylene glycol and sorbitol, amphotericin B, benzoic acid, methyl-, ethyl-, propyl- or butyl-paraben, sodium benzoate and sodium propionate, amiprilose, benzalkonium chloride, benzethonium chloride, benzyl alcohol, betapropiolactone, cetylpyridium chloride, chlorobutanol, chlortetracycline, EDTA, formaldehyde, gentamicin, kanamycin, neomycin, phenol, phenoxyethanol, phenylethyl alcohol, phenylmercuric nitrate, polymyxin B, streptomycin, thimerosal, tri-(n)-butyl phosphate, nystatin, water, alcohol especially ethyl alcohol, corn oil, cottonseed oil, glycerin, isopropyl alcohol, mineral oil, oleic acid, peanut oil, purified water, water for injection, sterile water for injection, benzalkonium chloride, magnesium stearate, nonoxynol 10, oxtoxynol 9 (Triton N-101), PLURONIC® or poloxamers such as PLURONIC® F-127, PLURONIC® F-68, PLURONIC® F-108, poloxamer 124, 188 (LUTROL® F-68), 237, 388 or 407 (LUTROL® F-127), polysorbate 20 (TWEEN™ 20), polysorbate 80

(TWEEN™ 80), sodium lauryl sulfate, sorbitan monopalmitate, agar, bentonite, carbomers (e.g., Carbopols such as carbopol EX55), carboxymethylcellulose sodium, gelatin, hydroxyethyl cellulose, hydroxypropyl cellulose, hydroxypropyl methylcellulose, kaolin, methylcellulose, tragacanth, veegum, carboxymethylcellulose sodium, gelatin, dextrose, glucose, sodium chloride, corn oil, mineral oil, peanut oil, sesame oil, bacteriostatic sodium chloride, bacteriostatic water, amino acids, bactopeptone, bovine albumin, bovine serum, egg protein, human serum albumin, mouse serum proteins, MRC-5 cellular protein, ovalbumin, vitamins, yeast proteins, apo-transferrin, aprotinin, anti-foaming agents such as polydimethylsilozone, silicon, fetuin (a serum protein), glycolic acid (a skin exfoliate), hydrogen peroxide (a detoxifier), lactose (a filler), mannose, urea, polycarbophils, polyacrylic acid (PAA), capricol, hyaluronic acid, chitosans, lectins, sodium alginate, pectin, acacia, and povidone.

Antigenic or immunogenic agents that may be used in the immunogenic compositions of the invention include antigens from an animal, a plant, a bacteria, a protozoan, a parasite, a virus or a combination thereof. The antigenic or immunogenic agent may be any viral peptide, protein, polypeptide, or a fragment thereof derived from a virus including, but not limited to, RSV-viral proteins, e.g., RSV F glycoprotein, RSV G glycoprotein, influenza viral proteins, e.g., influenza virus neuraminidase, influenza virus hemagglutinin, herpes simplex viral protein, e.g., herpes simplex virus glycoprotein including for example, gB, gC, gD, and gE. The antigenic or immunogenic agent for use in the compositions of the invention may be an antigen of a pathogenic virus such as, an antigen of adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory syncytial virus), metapneumovirus (e.g., avian pneumovirus and human metapneumovirus), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses), lentivirus (e.g. human immunodeficiency virus 1 and human immunodeficiency virus 2), spumavirus, flaviviridae (e.g., hepatitis C virus), hepadnaviridae (e.g., hepatitis B virus), togaviridae (e.g., alphavirus (e.g., sindbis virus) and rubivirus (e.g., rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Alternatively, the antigenic or immunogenic agent in the immunogenic compositions of the invention may be a cancer or tumor antigen including but not limited to, KS 1/4 pancarcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR (Epidermal growth factor receptor), HER2 antigen ($p185^{HER2}$), polymorphic epithelial mucin (PEM), malignant human lymphocyte antigen-APO-1, differentiation antigen such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group $Le^a$) found in Adenocarcinoma, NS-10 found in adenocarcinomas, CO-43 (blood group $Le^b$), G49 found in EGF receptor of A431 cells, MH2 (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA4 found in 4 to 8-cell stage embryos, and T cell receptor derived peptide from a Cutaneous T cell Lymphoma.

The antigenic or immunogenic agent for use in the immunogenic compositions of the invention may be any substance that under appropriate conditions results in an immune response in a subject, including, but not limited to, polypeptides, peptides, proteins, glycoproteins, lipids, nucleic acids and polysaccharides. The concentration of the antigenic or immunogenic agent in the immunogenic compositions of the invention may be determined using standard methods known to one skilled in the art and depends on the potency and nature of the antigenic or immunogenic agent. Given the enhanced efficacy provided by the compositions of the invention, the concentration of the antigenic or immunogenic agent is preferably less than the conventional amounts used.

In other embodiments, the dermal vaccine formulations of the invention (including the epidermal and dermal formulations) further comprise one or more additives, including, but not limited to, adjuvants, excipients, stabilizers, and penetration enhancers.

The intradermal vaccine delivery system of the invention is exemplified herein by an influenza vaccine formulation, which formulation enhances the protective immune response and efficacy of the influenza vaccine formulation when administered to the intradermal compartment of a subject's skin. In one specific embodiment, the influenza vaccine delivery system comprises one or more antigens derived from an influenza virus, and at least one biocompatible, biodegradable geling agent, e.g., a polymer, which undergoes a thermally induced physical transition from a liquid to a gel at a physiological temperature and at least one other agent including but not limited to a pre-selected excipient, a muco or bioadhesive. In another specific embodiment, the influenza vaccine delivery system comprises one or more antigens derived from an influenza virus, and at least two muco or bioadhesive molecules. In yet another specific embodiment, the influenza vaccine delivery system comprises one or more antigens derived from an influenza virus, at least one geling agent, e.g., a polymer, and at least one muco or bioadhesive.

The intradermal vaccine formulations of the invention are particularly advantageous for developing rapid and high levels of immunity against the antigenic or immunogenic agent, against which an immune response is desired. The intradermal vaccine formulations of the invention can achieve a systemic immunity at a protective level with a low dose of the antigenic or immunogenic agent. In some embodiments, the intradermal vaccine formulations of the invention result in a protective immune response with a dose of the antigenic or immunogenic agent which is 60%, preferably 50%, more preferably 40% of the dose conventionally used for the antigenic or immunogenic agent in obtaining an effective immune response. In preferred embodiments, the intradermal vaccine formulations of the invention comprise a dose of the antigenic or immunogenic agent which is lower than the conventional dose used in the art, e.g., the dose recommended in the Physician's Desk Reference, utilizing the conventional modes of vaccine delivery, e.g., intramuscular and intravenous. Preferably, the intradermal vaccine formulations of the invention result in a therapeutically or prophylactically effective immune response after a single intradermal dose. The intradermal vaccine formulations of the invention may be administered intradermally for annual immunizations.

The dermal vaccine formulations of the instant invention (including the epidermal and intradermal formulations) have an enhanced therapeutic efficacy, safety, and toxicity profile relative to currently available formulations. The benefits and advantages imparted by the dermal vaccine formulations of the invention is, in part, due to the particular formulation and their utility in targeting the intradermal compartment of skin. Preferably, the dermal vaccine formulations of the invention provide a greater and more durable protection, especially for high risk populations that do not respond well to immunization.

The invention further contemplates kits comprising an intradermal administration device and an intradermal vaccine formulation of the invention as described herein. The invention further contemplates kits comprising a dermal administration device and a dermal vaccine formulation of the invention as described herein. The invention further contemplates kits comprising an epidermal administration device and an epidermal vaccine formulation of the invention as described herein.

3.1 Definitions

As used herein, and unless otherwise specified, the term "excipient" means an ingredient or an additive in a composition, which itself possesses no pharmacological or biological activity for which the composition is intended, and preferably which, prior to the instant invention, was not known to directly enhance or otherwise alter such pharmacological or biological activity when administered to a subject, particularly in combination with one or more other excipients. Excipients used in the methods of the present invention are pre-selected excipients. As used herein, "pre-selected" excipients encompass traditional, non-traditional, and any other exicipient that has an adjuvant activity when delivered to a subject in accordance with the methods described herein.

As used herein, a "traditional" excipient is a more or less inert substance added in a composition as a diluent or vehicle. Alternatively, a traditional excipient may be used to give form or consistency to a composition. Examples of such traditional excipients are known to one skilled in the art and encompassed within the instant invention, see, e.g., *Remington's Pharmaceutical Sciences*, Mack Pub. Co., N.J., current edition; all of which is incorporated herein by reference in its entirety.

As used herein a "traditional" adjuvant is a substance added to a composition to enhance the antigenicity of the active ingredient in the composition, e.g., a suspension of minerals, on which an antigenic or immunogenic agent is absorbed, or water-in-oil emulsion in which an antigenic agent is emulsified in mineral oil (e.g., Freunds incomplete adjuvant), sometimes with the inclusion of killed mycobacteria to further enhance the antigenicity of the antigenic agent.

4. BRIEF DESCRIPTION OF THE FIGURES

FIG. 1 SERUM RESPONSE TO FLU ANTIGEN WHEN FLU INOCULUM IS SUPPLEMENTED WITH PLURONIC® F127. Serum antibody response following vaccination of Balb/c mice with a FLUZONE preparation containing PLURONIC® F127 is compared to FLUZONE preparation alone (w/o F127).

FIG. 2 SERUM RESPONSE TO FLU ANTIGEN WHEN FLU INOCULUM IS SUPPLEMENTED WITH PLURONIC® F127 AND A MUCOADHESIVE Serum antibody response following vaccination of Balb/c mice with FLUZONE preparation containing PLURONIC® F127 and a mucoadhesive is compared to FLUZONE preparation alone (w/o F127/mucoadhesive).

FIG. 3 SERUM RESPONSE TO FLU ANTIGEN WHEN FLU INOCULUM IS SUPPLEMENTED WITH PLURONIC® F127 AND CARBOXYMETHYLCELLULOSE. Serum antibody response following vaccination of Balb/c mice with FLUZONE preparation containing PLURONIC® F127 and carboxymethylcellulose is compared to FLUZONE preparation alone (w/o arboxymethylcellulose).

FIG. 4 SERUM RESPONSE TO FLU ANTIGEN WHEN FLU INOCULUM SUPPLEMENTED WITH GELATIN. Serum antibody response following vaccination of Balb/c mice with FLUZONE preparation containing gelatin is compared to FLUZONE preparation alone (w/o gelatin).

FIG. 5 SERUM RESPONSE TO FLU ANTIGEN WHEN FLU INOCULUM IS SUPPLEMENTED WITH METHYL CELLULOSE Serum antibody response following vaccination of Balb/c mice with FLUZONE preparation containing methylcellulose is compared to FLUZONE preparation alone (w/o methylcellulose).

FIG. 6 SERUM RESPONSE to flu antigen when flu inoculum is SUPPLEMENTED WITH METHYL CELLULOSE (END-POINT TITERS) Serum antibody response following vaccination of Balb/c mice with FLUZONE preparation containing methylcellulose is compared to FLUZONE preparation alone (w/o methylcellulose). Individual animal responses are plotted.

FIG. 7 DRAIZE SCORING IN SWINE A skin compatibility measurement is performed on the methylcellulose supplement and the methylcellulose when combined with FLUZONE immunogen.

FIG. 8 NEEDLE DEVICE. An exploded, perspective illustration of a needle assembly designed according to this invention.

FIG. 9 NEEDLE DEVICE. A partial cross-sectional illustration of the embodiment in FIG. 8.

FIG. 10 NEEDLE DEVICE. Embodiment of FIG. 9 attached to a syringe body to form an injection device.

FIG. 11A is an elevated view of the handle end of a preferred embodiment FIG. 11B is a side view of a preferred embodiment of a microabrader.

FIG. 12A is a transparent perspective view of the microabrader device of FIGS. 11A and 11B.

FIG. 12B is a cross sectional view of the microabrader device of FIG. 11B.

Figure 1:
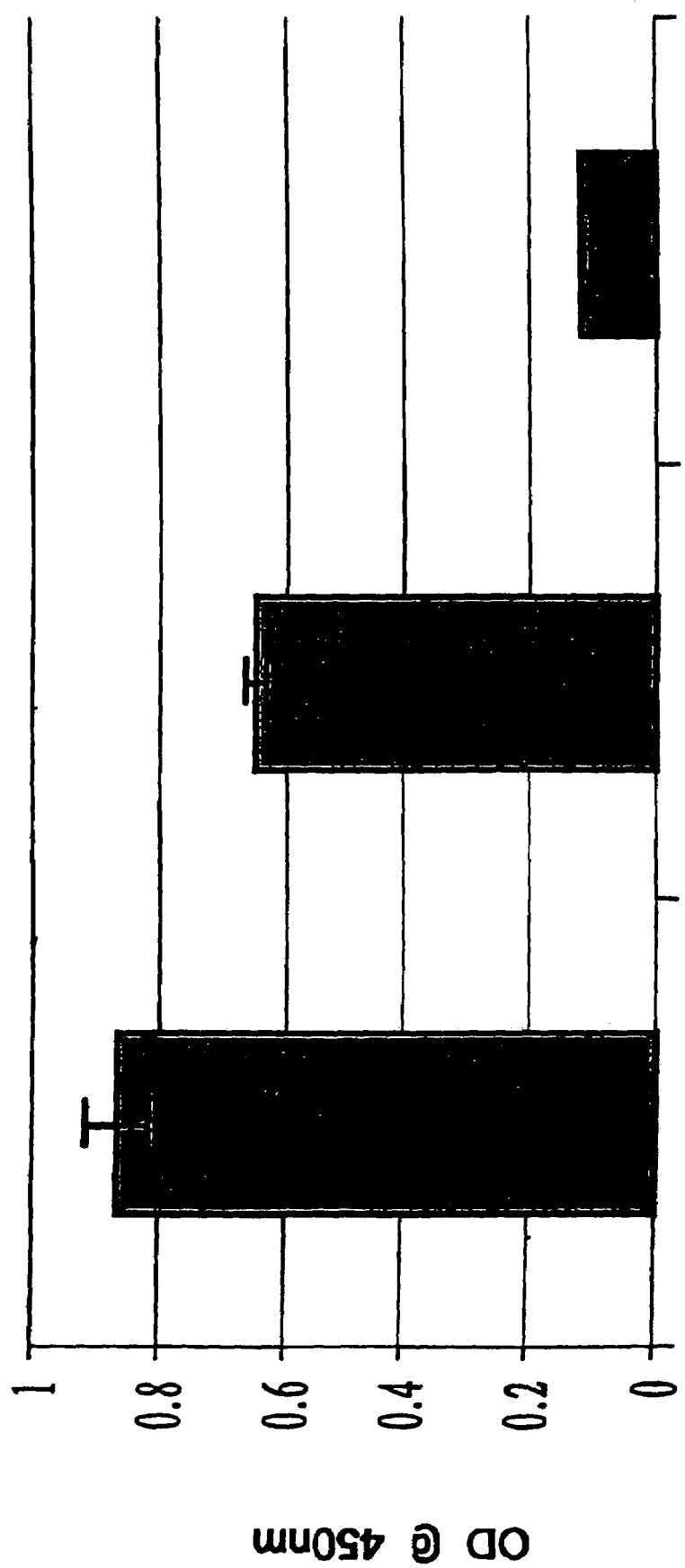
Figure 2:
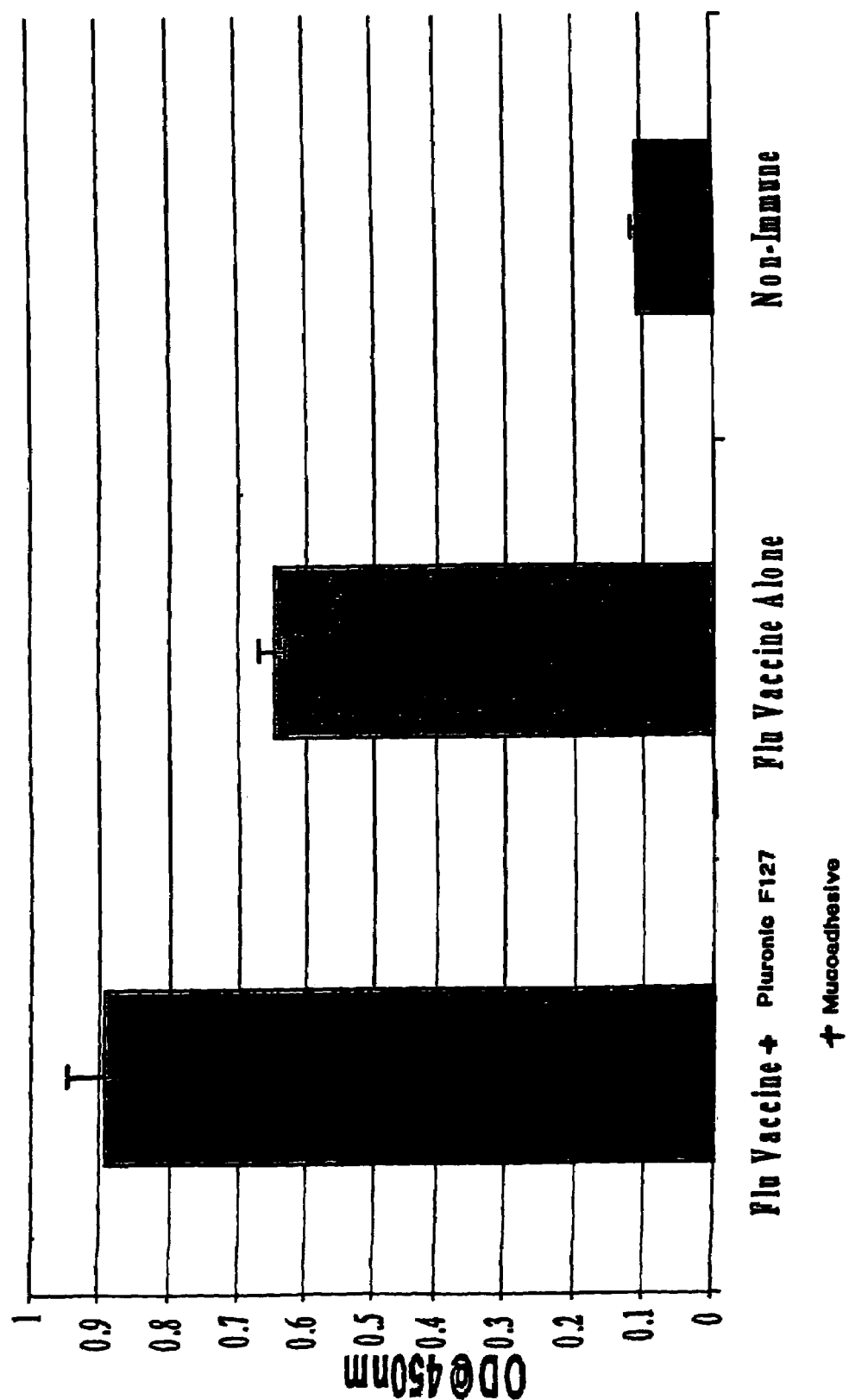
Figure 3:
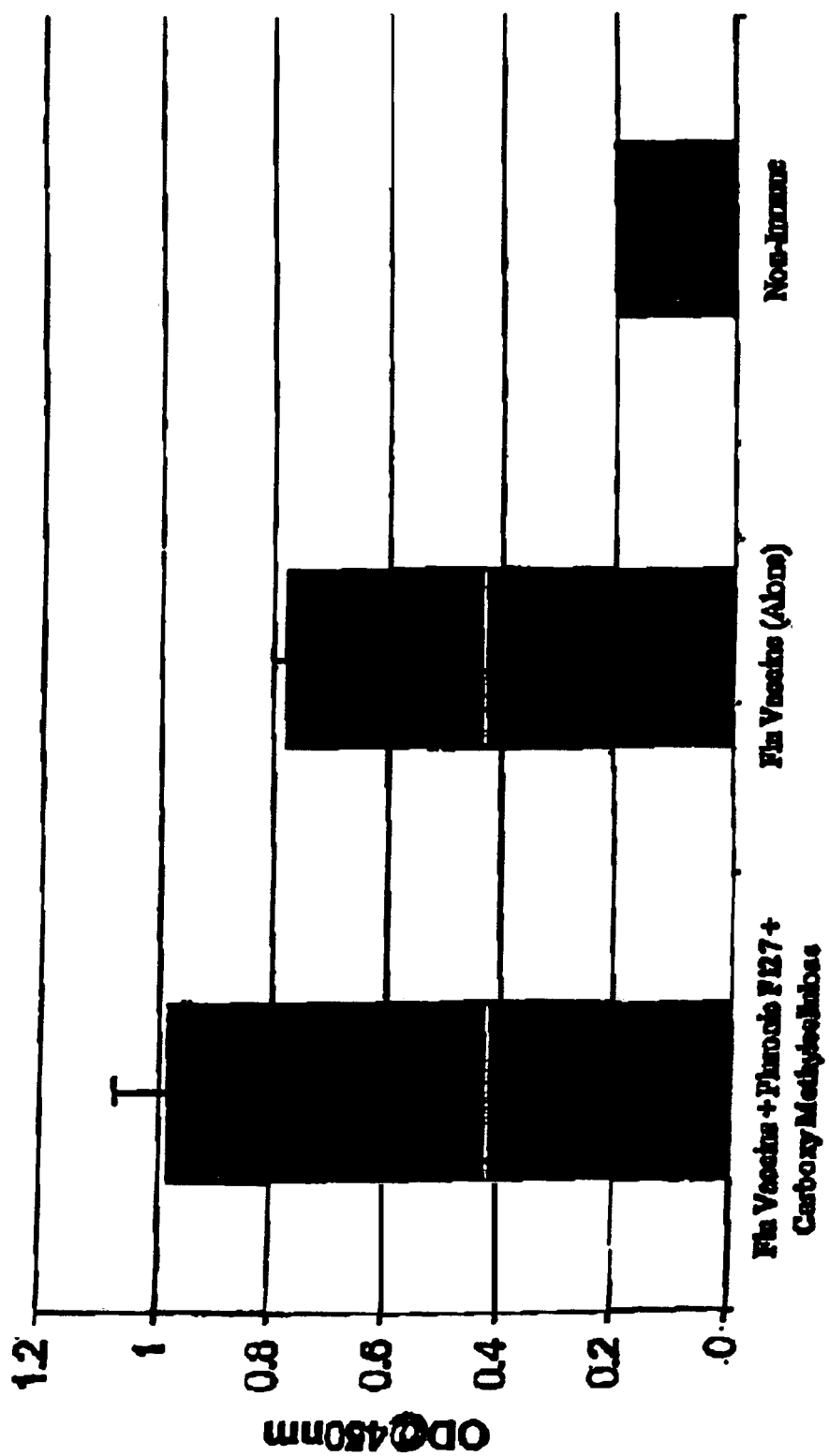
Figure 4:
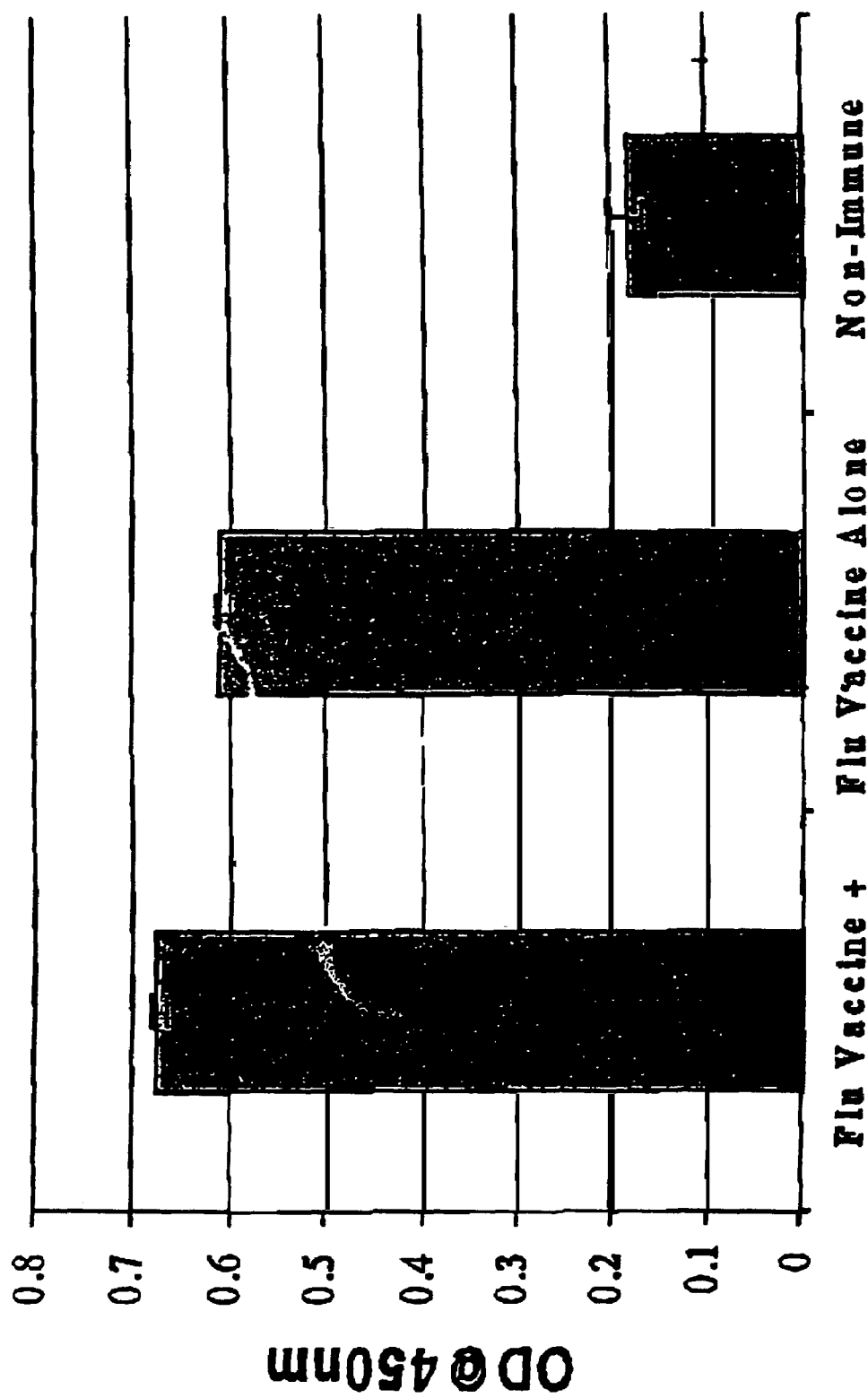
Figure 5:
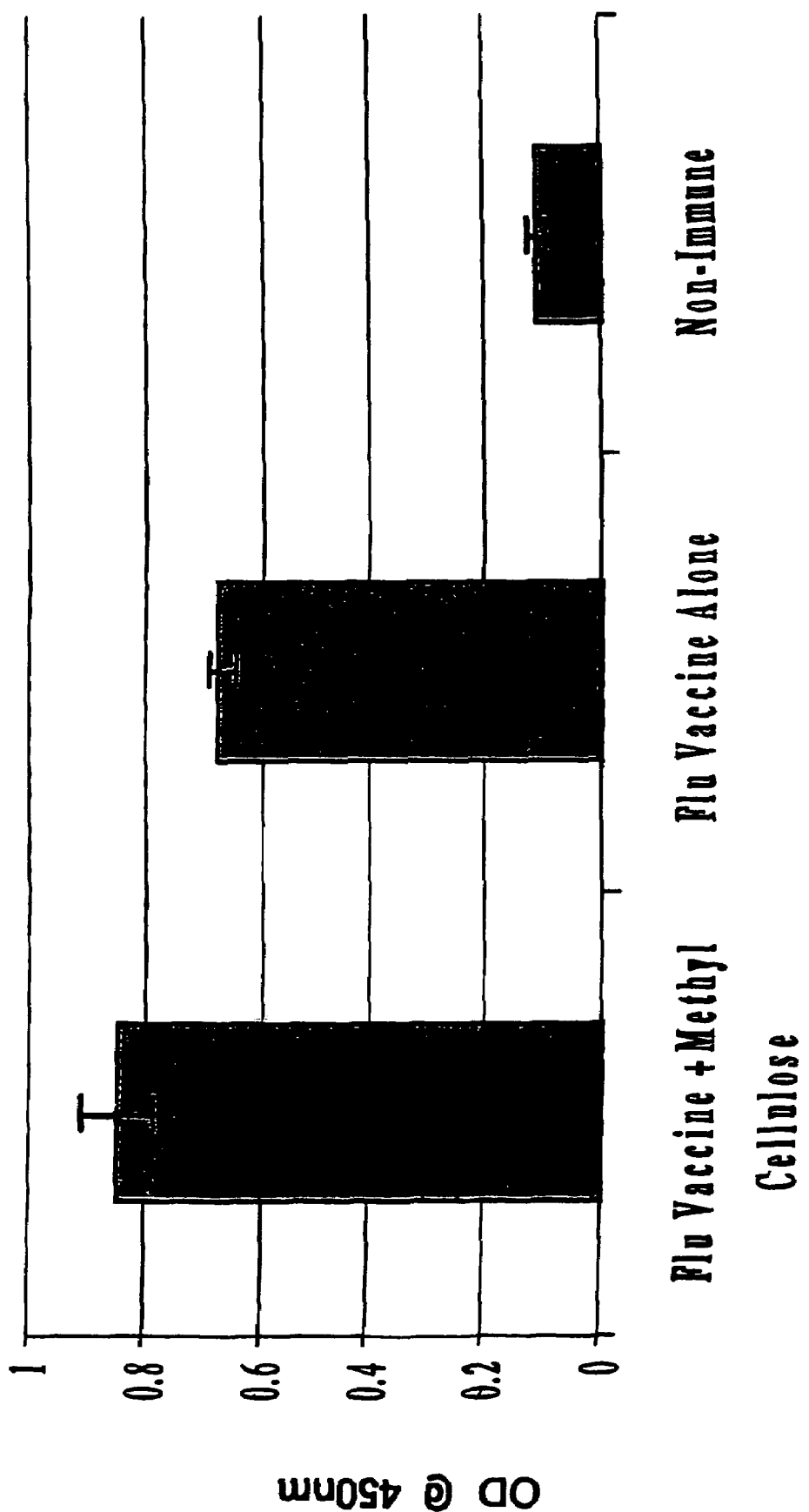

FIG. 17 Comparison of Fluzone vaccine alone, IM and ID 34-gauge 1 mm perpendicular needle, vs reformulated Fluzone vaccine with LUTROL® 5%+Methylcellulose 0.18% in Guinea Pigs by HAI assay (Trivalent cocktail).

FIG. 18 Comparison of IM and ID 34-gauge 1 mm perpendicular needle delivery of Fluzone vaccine alone vs. ID 34-gauge 1 mm perpendicular needle delivery of reformulated Fluzone vaccine (LUTROL® 15%+Methylcellulose 0.18%) in BalbC mice by HAI assay (H1N1 and H3N2 strains).

FIG. 19 Comparison of IM and ID 34-gauge 1 mm perpendicular needle delivery of Fluzone vaccine alone vs. ID 34-gauge 1 mm perpendicular needle delivery of reformulated Fluzone vaccine (LUTROL® 5%+Methylcellulose 0.18%) in BalbC mice by HAI assay (H1N1 and H3N2 strains).

FIG. 20 Comparison of IM and ID delivery of Fluzone vaccine alone vs ID 34-gauge 1 mm perpendicular needle delivery of reformulated Fluzone vaccine (LUTROL® 5%+Methylcellulose 0.18%) in Guinea pigs by HAI assay (H3N2 strain).

FIG. 21 Comparison of IM delivery of Fluzone vaccine alone vs ID 34-gauge 1 mm perpendicular needle delivery of reformulated Fluzone vaccine (LUTROL® 5%+Urea 0.2%) in Guinea pigs by HAI assay (Trivalent cocktail).

FIG. 22 Comparison of IM and ID 34-gauge 1 mm perpendicular needle delivery of Fluzone vaccine alone vs ID 34-gauge mm perpendicular needle delivery of reformulated Fluzone vaccine (LUTROL® 5%+Urea 0.2%) in Guinea pigs by HAI assay (H1N1, H3N2 and Hong Kong B-strain strains)

FIG. 23 Comparison of IM and ID 34-gauge 1 mm perpendicular needle delivery of Fluzone vaccine alone vs ID 34-gauge 1 mm perpendicular needle delivery of reformulated Fluzone vaccine (Gelatin 0.225%+Methylcellulose 0.18%) in Guinea pigs by HAI assay (Trivalent cocktail FIG. 24 Comparison of IM and ID 34-gauge 1 mm perpendicular needle delivery of Fluzone vaccine alone vs ID 34-gauge 1 mm perpendicular needle delivery of reformulated Fluzone vaccine (LUTROL® 5%+D-Sorbitol 5%) in Guine a pigs by HAI assay (Trivalent cocktail) and ELISA (Trivalent cocktail).

5. DETAILED DESCRIPTION OF THE INVENTION

The immunogenic compositions of the invention are designed to elicit an enhanced immunogenicity from the antigenic or immunogenic agent, when delivered to the dermal compartment of the subject's skin, e.g., intradermal or epidermal compartment. The immunogenic compositions of the invention comprise an antigenic or immunogenic agent with a cocktail comprising a combination of two or more agents including but not limited to two or more pre-selected excipients, two or more mucoadhesives, two or more bioadhesives, or two or more geling agents or any combination thereof results in an enhanced immune response to the antigenic or immunogenic agent, when delivered to the dermal compartment, including the epidermal and intradermal compartments. The enhanced efficacy of the compositions of the invention is based, in part, on the appreciation and recognition by the inventors that specific combinations of such agents, can act as adjuvants, resulting in an enhanced immune response to the antigenic or immunegic agent once delivered to the dermal compartment.

Without being limited by a particular theory, it is found that a combination of two or more agents can synergistically or additively act to enhance the immunogenicity of the antigen or immunogen comprised in the compositions of the invention, resulting in an enhanced immune response to the antigen or immunogen. Preferably, the agent used in connection with this invention has not been previously associated with an enhanced immune response, particularly in the intradermal compartment. More preferably, the combination of two or more agents of the invention has not been previously associated with an enhanced immune response, particularly in the intradermal compartment, particularly at the dosages disclosed herein.

In some embodiments, the immunogenic compositions of the invention comprise an antigenic or immunogenic agent in combination with two or more mucoadhesives. In other embodiments, the immunogenic compositions of the invention comprise an antigenic or immunogenic agent in combination with two or more bioadhesives. In a specific embodiment, the muco or bioadhesive includes but is not limited to gelatin, methylcellulose, chitosan and carboxymethylcellulose.

In yet other embodiments, the immunogenic compositions of the invention comprise an antigenic or immunogenic agent in combination with at least two agents, wherein the first agent is a geling agent e.g., polymerizes or gels at a physiological temperature and the second agent is a mucoadhesive or bioadhesive. In a specific embodiment, the geling agent is LUTROL® and the mucoadhesive or bioadhesive includes but is not limited to gelatin, methylcellulose, chitosan and carboxymethylcellulose.

In yet other embodiments, the immunogenic compositions of the invention comprise an antigenic or immunogenic agent in combination of at least two agents, wherein the first agent is a geling agent and the second agent is a pre-selected excipient. In a specific embodiment the geling agent is LUTROL® and the excipient includes but is not limited to methylcellulose, gelatin, sorbitol, chitosan, and urea.

In yet other embodiments, the immunogenic compositions of the invention comprise an antigenic or immunogenic agent in combination of at least two agents, wherein the first agent is a muco or bioadhesive and the second agent is a muco or bioadhesive.

In another embodiment, the composition of the invention comprises an antigenic or immunogenic agent in combination of at least two agents, wherein the first agent is a muco or bioadhesive (e.g., gelatin, methylcellulose, LUTROL® ) and the second agent is a pre-selected excipient including but not limited to, LUTROL® , gelatin, sorbitol, chitosan, and urea In yet another specific embodiment, the composition of the invention comprises an antigenic or immunogenic agent in combination of at least two pre-selected excipients, including but not limited to, LUTROL®, gelatin, sorbitol, chitosan, and urea.

The concentration of the agents in the dermal vaccine formulations (including intradermal and epidermal vaccine formulations) of the invention depends on the particular agent used. In a specific embodiment, when the agent is a polymer, the concentration of the polymer used in the dermal vaccine formulations of the invention may be at least 5% (w/v), at least 10% (w/v), at least 15% (w/v), at least 20% (w/v), at least 25% (w/v), or at least 30% (w/v). In some embodiments, the concentration of the polymer is greater than about 30% (w/v). In another specific embodiment, when the molecule is a muco or bioadhesive, the concentration used in the dermal vaccine formulations of the invention may be at least 0.1% (w/v), at least 0.5% (w/v), at least 1% (w/v), at least 5% (w/v), or at least 10% (w/v).

In one embodiment, the immunogenic composition of the invention comprises LUTROL® in combination with one or more other excipients. The concentration of LUTROL® used in the composition of the invention in combination with other excipients may be from about 0.001% w/v to about 50% w/v, from about 0.01% w/v to about 45% w/v, from about 1% w/v to about 40% w/v, from about 2% w/v to about 30% w/v, from about 3% w/v to about 20% w/v, from about 5% w/v to about 15% w/v, from about 5% w/v to about 10% w/v, or from about 3% w/v to about 7% w/v.

In one embodiment, the immunogenic composition of the invention comprises methylcellulose in combination with one or more other excipients. The concentration of LUTROL® used in the composition of the invention in combination with other excipients may be from about 0.0001% w/v to about 20% w/v, from about 0.001% w/v to about 15% w/v, from about 0.005% w/v to about 10% w/v, from about 0.01% w/v to about 5% w/v, from about 0.05% w/v to about 2% w/v, from about 0.001% w/v to about 1% w/v, from about 0.005% w/v to about 0.5% w/v, or from about 0.01% w/v to about 0.1% w/v.

In another embodiment, the immunogenic composition of the invention comprises gelatin in combination with one or more other excipients. The concentration of gelatin used in the composition of the invention may be from about 0.001 w/v to about 30% w/v, from about 0.005% w/v to about 20% w/v, from about 0.01% w/v to about 10% w/v, from about 0.01% w/v to about 5% w/v, from about 0.01% w/v to about 0.5% w/v, from about 0.05 w/v to about 3% w/v, or from about 0.1% w/v to about 0.3% w/v.

In one embodiment, the immunogenic composition of the invention comprises sorbitol in combination with one or more other excipients. The concentration of sorbitol used in the composition of the invention in combination with other excipients may be from about 0.001% w/v to about 50% w/v, from about 0.01% w/v to about 45% w/v, from about 1% w/v to about 40% w/v, from about 2% w/v to about 30% w/v, from about 3% w/v to about 20% w/v, from about 5% w/v to about 15% w/v, from about 5% w/v to about 10% w/v, or from about 3% w/v to about 7% w/v.

In one embodiment, the immunogenic composition of the invention comprises chitosan in combination with one or more other excipients. The concentration of chitosan used in the composition of the invention in combination with other excipients may be from about 0.001% w/v to about 30% w/v, from about 0.005% w/v to about 20% w/v, from about 0.01% w/v to about 10% w/v, from about 0.01% w/v to about 5% w/v, from about 0.05% w/v to about 1% w/v, from about 0.05% w/v to about 3% w/v, or from about 0.1% w/v to about 0.5% w/v.

In one embodiment, the immunogenic composition of the invention comprises urea in combination with one or more other excipients. The concentration of urea used in the composition of the invention in combination with other excipients may be from about 0.001% w/v to about 50% w/v, from about 0.005% w/v to about 40% w/v, from about 0.01% w/v to about 30% w/v, from about 0.05% w/v to about 20% w/v, from about 0.1% w/v to about 10% w/v, from about 1% w/v to about 15% w/v, from about 0.1% w/v to about 5% w/v, or from about 0.2% w/v to about 2% w/v.

In one specific embodiment, an immunogenic composition of the invention comprises the combination of LUTROL® and methylcellulose. The concentration of LUTROL® used in the immunogenic compositions of the invention may be from about 1% w/v to about 25% w/v, from about 3% w/v to about 15% w/v, or from about 5% w/v to about 10% w/v. The concentration of methylcellulose used in the immunogenic compositions of the invention may be from about 0.001% w/v to about 1% w/v, from about 0.01% w/v to about 0.5% w/v, or from about 0.02% w/v to about 0.1% w/v.

In another embodiment, an immunogenic composition of the invention comprises the combination of LUTROL® and sorbitol. The concentration of LUTROL® used in the immunogenic compositions of the invention may be from about 1% w/v to about 25% w/v, from about 3% w/v to about 15% w/v, or from about 5% w/v to about 10% w/v. The concentration of sorbitol used in the immunogenic compositions of the invention may be from about 0.5% w/v to about 25% w/v, from about 3% w/v to about 15% w/v, or from about 5% w/v to about 10% w/v.

In another embodiment, an immunogenic composition of the invention comprises the combination of LUTROL® and urea. The concentration of LUTROL® used in the immunogenic compositions of the invention may be from about 1% w/v to about 25% w/v, from about 3% w/v to about 15% w/v, or from about 5% w/v to about 10% w/v. The concentration of urea used in the immunogenic compositions of the invention may be from about 0.01% w/v to about 40% w/v, from about 0.1% w/v to about 10% w/v, or from about 0.2% w/v to about 1% w/v.

In another embodiment, an immunogenic composition of the invention comprises the combination of LUTROL® and chitosan. The concentration of LUTROL® used in the immunogenic compositions of the invention may be from about 1% w/v to about 25% w/v, from about 3% w/v to about 15% w/v, or from about 5% w/v to about 10% w/v. The concentration of chitosan used in the immunogenic composition of the invention may from about from about 0.01% w/v to about 1% w/v, from about 0.05% w/v to about 0.5% w/v, or from about 0.1% w/v to about 0.25% w/v.

In another embodiment, an immunogenic composition of the invention comprises the combination of methylcellulose and gelatin. The concentration of methylcellulose used in the immunogenic compositions of the invention may be from about 0.001% w/v to about 1% w/v, from about 0.01% w/v to about 0.5% w/v, or from about 0.02% w/v to about 0.1% w/v. The concentration of gelatin used in the immunogenic composition of the invention may be from about 0.01% w/v to about 5% w/v, from about 0.05% w/v to about 0.5% w/v, or from about 0.1% w/v to about 0.225 w/v.

The invention encompasses dermal vaccine formulations for for targeted delivery of the antigenic or immunogenic agent, preferably, selectively and specifically to a particular compartment of a subject's skin including the intradermal and epidermal compartments. In some embodiments, the dermal vaccine formulations of the invention are designed for targeted delivery of the antigenic or immunogenic agent, preferably, selectively and specifically, to the intradermal compartment of a subject's skin. In some embodiments, the intradermal vaccine formulations of the invention are targeted directly to the intradermal compartment of skin.

The benefits of the invention are based, in part, on the appreciation and recognition by the inventors that the intradermal compartment provides an ideal immunological space for a direct access of the antigenic or immunogenic agent to the immune cells residing therein. Indeed, the intradermal compartment has rarely been effectively targeted as a site of delivery of an antigenic or immunogenic agent, at least, in part, due to the difficulty of a specific and reproducible delivery of the antigenic or immunogenic agent, i.e., the precise needle placement into the intradermal space and adequate pressures of delivery.

The benefits of the invention are also appreciated in other dermal compartments including but not limited to the epidermal compartment of skin since. Although not intending to be bound by any particular mechanism of action, the skin represents an attractive target site for delivery of vaccines and gene therapeutic agents. In the case of vaccines (both genetic and conventional), the skin is an attractive delivery site due to the high concentration of antigen presenting cells (APC) and APC precursors found within this tissue, especially the epidermal Langerhan's cells (LC) and the immune cells in the intradermal compartment.

The enhanced efficacy of the formulations of the inventions may be achieved with dermal vaccine formulations including formulations for intradermal and epidermal delivery. In some embodiments, the dermal vaccine formulations of the invention (including the epidermal and intradermal formulations) comprise an antigenic or immunogenic agent, and two or more agents, which enhances the presentation and/or availability of the antigenic or immunogenic agent to an immune cell, e.g., the immune cells of the intradermal compartment (e.g., antigen presenting cells) or the immune cells of the epidermal compartment (e.g., epidermal Langerhan's cells (LC)), resulting in an enhanced protective immune response. In a specific embodiment, the two or more agents acts to prolong the exposure of the antigenic or immunogenic agent to the immune cells of the dermal compartment, e.g., antigen presenting cells, epidermal Langerhan's cells (LC), resulting in an enhanced protective immune response.

The dermal vaccine formulations of the invention (including the epidermal and intradermal formulations) have enhanced efficacy, e.g., enhanced protective immune response, as the antigenic or immunogenic agent is delivered to the dermal compartment with an enhanced availability and/or presentation to the immune cells that reside therein, e.g., antigen presenting cells. Alternatively, the dermal vaccine formulations of the invention have enhanced efficacy as the antigenic or immunogenic agent is delivered to the dermal compartment, with a prolonged exposure of the antigenic or immunogenic agent to the immune cells that reside therein, resulting in an enhanced immune response. The enhanced efficacy of the dermal vaccine formulations (including the epidermal and dermal formulations) results in a therapeutically effective response, e.g., protective immune response, after a single dermal dose, with lower doses of the antigenic or immunogenic agent than conventionally used, and without the need for booster immunizations.

Although not intending to be bound by a particular mechanism of action, the intradermal vaccine formulations of the invention achieve an enhanced therapeutic efficacy, e.g., enhanced protective immune response, in part, due to the persistance of the antigenic or immunogenic agent at the site of the injection, i.e., the "depot effect". Preferably, the intradermal vaccine formulations of the invention decrease the clearance rate of the antigenic or immunogenic agent from the site of the injection. More preferably, the intradermal vaccine formulations of the invention allow slow release of the antigenic or immunogenic agent at the site of injection, e.g., the dermal space.

The intrademal vaccine formulations of the invention may enhance the immunological response or therapeutic efficacy of the antigenic or immunogenic agent by (1) enhancing the immunogenicity of the antigenic or immunogenic agent; (2) enhancing the speed and/or duration of the immune response; (3) modulating the avidity, specificity, isotype or class distribution of the antibody response; (4) stimulating cell-mediated immune response; (5) promoting mucosal immunity, or (6) decreasing the dose of the antigenic or immunogenic agent.

Although not intending to be bound by a particular mode of action, the intradermal vaccine formulations of the invention enhance cell-mediated immune response by specifically targeting the antigenic or immunogenic agent to the intradermal compartment of skin, which comprises of antigen presenting cells, e.g., dendritic cells and Langerhan cells. The intradermal vaccine formulations of the invention may enhance cell-mediated and/or humoral mediated immune response. Cell-mediated immune responses that may be modulated by the intradermal vaccine formulations of the invention include for example, Th1 or Th2 CD4+ T-helper cell-mediated or CD8+ cytotoxic T-lymphocytes mediates responses.

In some embodiments, the dermal vaccine formulations of the invention are designed for targeted delivery of the antigenic or immunogenic agent, preferably, selectively and specifically, to the epidermal compartment of a subject's skin. In some embodiments, the epidermal vaccine formulations of the invention are targeted directly to the epidermal compartment of skin.

The geling agents that may be used in the dermal vaccine formulations of the invention include polymers that polymerize or gel, e.g., form a semi-solid or solid two or three dimensional matrix. Preferably such molecules once administered to the intradermal or epidermal compartment, thus allow for example, interaction and exposure of the antigenic or immunogenic agent with the immunological space therein. In most preferred embodiments, polymers used in the dermal vaccine formulations of the invention do not form liposomal or micellar structures. The polymer preferably enhances the presentation and/or availability of the antigenic or immunogenic agent to the immune cells of the dermal compartment, e.g., immune cells in the intradermal or epidermal compartments. Preferably, the molecule used in the dermal vaccine formulations (including intradermal and epidermal vaccine formulations) of the invention is biocompatible and/or biodegradable. In a specific embodiment, the molecule is a biomolecule, including, but not limited to, a protein, a polypeptide, and a peptide.

The geling agents that may be used in the compositions of the invention polymerize or gel once administered to the dermal space, creating a semi-solid to solid gelatinous matrix. In some embodiments, the gelatinous matrix allows for an enhanced presentation and/or interaction of the antigenic and/or or immunogenic agent with the immune cells in the dermal space. In a specific embodiment, the geling agent is a polymer that polymerizes or gels once administered to the dermal space. Preferably, the polymers for use in the dermal vaccine formulations of the invention enhance the presentation and/or availability of the antigenic or immunogenic agent to the immune cells of the dermal compartment, e.g., antigen presenting cells.

Geling agents that may be used in the dermal vaccine formulations of the invention (including the epidermal and intradermal formulations) include polymers, preferably biocompatible and/or biodegradable polymers, which undergo a thermally induced physical transition from a liquid to a gel at a physiological temperature, e.g., a temperature ranging from 25° to 37° C. It will be appreciated by one skilled in the art, that the physiological temperature should be at a temperature above the liquid-gel transition of the polymer. Preferably, the polymer is a non-ionic block copolymer, also known as a PLURONIC® or Poloxamer, including, but not limited to, PLURONIC® F-127, PLURONIC® F-68, and PLURONIC® F108. In some embodiments, the polymer acts as a depot. Alternatively, the polymer may enhance the presentation and/or availability of the antigenic or immungenic agent to the immune cells of the dermal compartments, e.g., antigen presenting cells. In some embodiments, the polymer is an adjuvant. In yet other embodiments, the polymer is also a bioadhesive and/or a mucoadhesive. One advantage of the use of polymers in the intradermal vaccine formulations of the invention is that they are particularly well suited for intradermal delivery in that, at a temperature below the physiological temperature, e.g., a temperature ranging from 25° to 37° C., the intradermal vaccine formulation is a liquid, and after intradermal injection, the intradermal vaccine formulation forms a gel as it is warmed in the subject to a temperature above the liquid-gel transition temperature. In a specific embodiment, the gelatinous formulation may allow slow release of the antigenic or immunogenic agent in the dermis, potentiating an effective immune response. Furthermore, the intradermal vaccine delivery system of the invention is ideal for intradermal administration since the gelatinous material prevents any fluid leakage, thereby adding to an already established benefit of intradermal delivery.

Examples of muco or bioadhesives that may be used in the dermal vaccine formulations of the invention include, but are not limited to, polycarbophils, polyacrylic acid (PAA), carobopols, Carbopol EX55, capricol, carbomers, polysaccharides, hyaluronic acid, chitosans; lectins; cellulose, methylcellulose, carboxymethylcellulose, hydroxypropyl methyl cellulose, sodium alginate, gelatin, pectin, acacia, and povidone. Although not intending to be bound by a particular mechanism of action, muco or bioadhesives enhance the presentation and/or availability of the antigenic or immunogenic agent to the immune cells of the dermal compartment. In some embodiments, the muco or bioadhesive may permit the antigenic or immunogenic agent to adhere to the immune cells of the dermal space, e.g., antigen presenting cells. In some embodiments, the invention encompasses an dermal vaccine formulation comprising an antigenic or immunogenic agent and at least two muco or bioadhesive molecules. In some embodiments, the muco or bioadhesive used in the dermal vaccine formulations of the invention may facilitate adherence of the antigenic or immunogenic agent to the cell surface of the immune cells of the dermal compartment.

Excipients which may be used in the immunogenic compositions of the invention include, but are not limited to, stabilizers, preservatives, solvents, surfactants or detergents, suspending agents, tonicity agents, geling agents, muco/bioadhesives, vehicles and ingredients for growth medium. A non-limiting list of excipients that may be used in the immunogenic compositions of the invention are acetic acid, citric acid, fumaric acid, hydrochloric acid, nitric acid, sodium acetate, cellulose, charcoal, gelatin, ammonia solution, ammonium carbonate, mono-, di- or tri-ethanolamine, potassium hydroxide, sodium borate, sodium carbonate, sodium hydroxide, trolamine, nitrogen gas, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, sodium sulfite, glycine, potassium metaphosphate, potassium phosphate, monobasic sodium acetate, anhydrous or dihydrate sodium citrate, edetate disodium, edetic acid, glycerin, propylene glycol and sorbitol, amphotericin B, benzoic acid, methyl-, ethyl-, propyl- or butyl-paraben, sodium benzoate and sodium propionate, amiprilose, benzalkonium chloride, benzethonium chloride, benzyl alcohol, betapropiolactone, cetylpyridium chloride, chlorobutanol, chlortetracycline, EDTA, formaldehyde, gentamicin, kanamycin, neomycin, phenol, phenoxyethanol, phenylethyl alcohol, phenylmercuric nitrate, polymyxin B, streptomycin, thimerosal, tri-(n)-butyl phosphate, nystatin, water, alcohol especially ethyl alcohol, corn oil, cottonseed oil, glycerin, isopropyl alcohol, mineral oil, oleic acid, peanut oil, purified water, water for injection, sterile water for injection, benzalkonium chloride, magnesium stearate, nonoxynol 10, oxtoxynol 9 (Triton N-101), PLURONIC® or poloxamers such as PLURONIC® F-127, PLURONIC® F-68, PLURONIC® F-108, poloxamer 124, 188 (LUTROL® F-68), 237, 388 or 407 (LUTROL® F-127), polysorbate 20 (TWEEN™ 20), polysorbate 80 (TWEEN™ 80), sodium lauryl sulfate, sorbitan monopalmitate, agar, bentonite, carbomers (e.g., Carbopols such as carbopol EX55), carboxymethylcellulose sodium, gelatin, hydroxyethyl cellulose, hydroxypropyl cellulose, hydroxypropyl methylcellulose, kaolin, methylcellulose, tragacanth, veegum, carboxymethylcellulose sodium, gelatin, dextrose, glucose, sodium chloride, corn oil, mineral oil, peanut oil, sesame oil, bacteriostatic sodium chloride, bacteriostatic water, amino acids, bactopeptone, bovine albumin, bovine serum, egg protein, human serum albumin, mouse serum proteins, MRC-5 cellular protein, ovalbumin, vitamins, yeast proteins, apo-transferrin, aprotinin, anti-foaming agents such as polydimethylsilozone, silicon, fetuin (a serum protein), glycolic acid (a skin exfoliate), hydrogen peroxide (a detoxifier), lactose (a filler), mannose, urea, polycarbophils, polyacrylic acid (PAA), capricol, hyaluronic acid, chitosans, lectins, sodium alginate, pectin, acacia, and povidone.

The concentration of the excipient used in the immunogenic compositions of the invention depends on the particular excipient used. In some embodiments, the concentration of the excipient used in the immunogenic compositions of the invention may be at 0.000002% to 58% (w/v) and 0.05% to 0.45% (v/v). In other embodiments, the concentration of the excipient used may be at least 10% (w/v), at least 15% (w/v), at least 20% (w/v), at least 25% (w/v), or at least 30% (w/v). In other embodiments, the concentration of the excipient is greater than about 30% (w/v). In yet other embodiments, the concentration of the excipient is at least 0.1% (w/v), at least 0.5% (w/v), at least 1% (w/v), at least 5% (w/v), or at least 10% (w/v).

Antigenic or immunogenic agents that may be used in the immunogenic compositions of the invention include antigens from an animal, a plant, a bacteria, a protozoan, a parasite, a virus or a combination thereof. The antigenic or immunogenic agent may be any viral peptide, protein, polypeptide, or a fragment thereof derived from a virus including, but not limited to, RSV-viral proteins, e.g., RSV F glycoprotein, RSV G glycoprotein, influenza viral proteins, e.g., influenza virus neuraminidase, influenza virus hemagglutinin, herpes simplex viral protein, e.g., herpes simplex virus glycoprotein including for example, gB, gC, gD, and gE. The antigenic or immunogenic agent for use in the compositions of the invention may be an antigen of a pathogenic virus such as, an antigen of adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory syncytial virus), metapneumovirus (e.g., avian pneumovirus and human metapneumovirus), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses), lentivirus (e.g. human immunodeficiency virus 1 and human immunodeficiency virus 2), spumavirus, flaviviridae (e.g., hepatitis C virus), hepadnaviridae (e.g., hepatitis B virus), togaviridae (e.g., alphavirus (e.g., sindbis virus) and rubivirus (e.g., rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Alternatively, the antigenic or immunogenic agent in the immunogenic compositions of the invention may be a cancer or tumor antigen including but not limited to, KS 1/4 pancarcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, C017-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR (Epidermal growth factor receptor), HER2 antigen (p185$^{HER2}$), polymorphic epithelial mucin (PEM), malignant human lymphocyte antigen-APO-1, differentiation antigen such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA4 found in 4 to 8-cell stage embryos, and T cell receptor derived peptide from a Cutaneous T cell Lymphoma.

The antigenic or immunogenic agent for use in the immunogenic compositions of the invention may be any substance that under appropriate conditions results in an immune response in a subject, including, but not limited to, polypeptides, peptides, proteins, glycoproteins, lipids, nucleic acids and polysaccharides. The concentration of the antigenic or immunogenic agent in the immunogenic compositions of the invention may be determined using standard methods known to one skilled in the art and depends on the potency and nature of the antigenic or immunogenic agent. Given the enhanced efficay provided by the compositions of the invention, the concentration of the antigenic or immunogenic agent is preferably less than the conventional amounts used.

In other embodiments, the dermal vaccine formulations of the present invention (including intradermal and epidermal vaccine formulations) may further comprise one or more other pharmaceutically acceptable carriers, including any suitable diluent or excipient. Preferably, the pharmaceutically acceptable carrier does not itself induce a physiological response, e.g., an immune response. Most preferably, the pharmaceutically acceptable carrier does not result in any adverse or undesired side effects and/or does not result in undue toxicity. Pharmaceutically acceptable carriers for use in the dermal vaccine formulations of the invention (including intradermal and epidermal vaccine formulations) include, but are not limited to, saline, buffered saline, dextrose, water, glycerol, sterile isotonic aqueous buffer, and combinations thereof. Additional examples of pharmaceutically acceptable carriers, diluents, and excipients are provided in *Remington's Pharmaceutical Sciences* (Mack Pub. Co., N.J., current edition; all of which is incorporated herein by reference in its entirety).

In particular embodiments, the dermal vaccine formulation of the invention (including intradermal and epidermal vaccine formulations), may also contain wetting agents, emulsifying agents, or pH buffering agents. The dermal vaccine formulations of the invention (including intradermal and epidermal vaccine formulations) can be a solid, such as a lyophilized powder suitable for reconstitution, a liquid solution, a suspension, a tablet, a pill, a capsule, a sustained release formulation, or a powder. In a specific preferred embodiment, the intradermal vaccine formulation of the invention is not an emulsion, since intradermal delivery of emulsions are technically difficult and are labor intensive.

The intradermal vaccine formulations of the invention may be in any form suitable for intradermal delivery. In one embodiment, the intradermal vaccine formulation of the invention is in the form of a flowable, injectable medium, i.e., a low viscosity formulation that may be injected in a syringe. In another embodiment, the intradermal vaccine formulation of the invention is in the form of a gelatinous matrix, e.g., a semi-solid or solid two or three dimensional matrix. In yet another embodiment, the intradermal vaccine formulation of the invention is in the form of a highly viscous, thick medium with limited fluidity. In either embodiment, the antigenic or immunogenic agent is uniformly and homogenously dispersed throughout the formulation. In a preferred embodiment, the intradermal vaccine formulation is capable of transitioning from a flowable, injectable medium to a gel, and vice versa, by a change in temperature so that the intradermal vaccine formulation is in the form of a flowable, injectable medium below the transition temperature and a gel above the transition temperature. The flowable, injectible medium may be a liquid. Alternatively, the flowable, injectable medium is a liquid in which particulate material is suspended, such that the medium retains fluidity to be injectable and syringible, e.g., can be administered using a syringe.

The epidermal vaccine formulations of the invention may be in any form suitable for intradermal delivery, such as those dislcosed in U.S. Provisional patent application Nos. 60/330, 713, 60/333,162 and U.S. application Ser. Nos. 09/576,643, 10/282,231, filed Oct. 29, 2001, Nov. 27, 2001, and May 22, 2000 and Oct. 29, 2002, respectively, all of which are each hereby incorporated by reference in their entirety.

Preferably, the dermal vaccine formulations of the invention (including the intradermal and epidermal vaccine formulations) are stable formulations, i.e., undergo minimal to no detectable level of degradation and/or aggregation of the antigentic or immunogenic agent, and can be stored for an extended period of time with no loss in biological activity, e.g., antigenicity or immunogenicity of the antigenic agent. The stability of the dermal vaccine formulations of the invention is, in part, due to the antigenic or immuonogenic agent being embedded, e.g., uniformly and homogeneously dispersed, in the gelatinous matrix of the polymer, which provides a stable polymeric structural network that protects and shields the antigenic or immunogenic agent from degradation and/or other unwanted modifications that result in a decrease in biological activity.

In some embodiments, the dermal vaccine formulations of the present invention exhibit stability at the temperature ranges of 2° C.-8° C., preferably at 4° C., for at least 2 years when the intradermal vaccine formulation is in a liquid form (i.e., not in a gel form), as assessed by high performance size exclusion chromatography (HPSEC). Namely, the dermal vaccine formulations of the present invention have low to undetectable levels of aggregation and/or degradation of the anitgenic or immunogenic agent, after the storage for the defined periods as set forth above. Preferably, no more than 5%, no more than 4%, no more than 3%, no more than 2%, no more than 1%, and most preferably no more than 0.5%, of the antigenic or immunogenic molecule forms an aggregate or degrades as measured by HPSEC, after the storage for the defined periods as set forth above. Furthermore, the dermal vaccine formulations of the present invention exhibit almost no loss in biological activity of the antigenic or immunogenic agent during the prolonged storage under the conditions described above, as assessed by standard methods known in the art. The dermal vaccine formulations of the present invention retain after the storage for the above-defined periods more than 80%, more than 85%, more than 90%, more than 95%, more than 98%, more than 99%, or more than 99.5% of the initial biological activity prior to the storage.

The concentration of the antigenic or immunogenic agent in the dermal vaccine formulation of the invention (including intradermal and epidermal vaccine formulations) may be determined using standard methods skilled in the art and depends on the potency and nature of the antigenic or immunogenic agent. Given the enhanced delivery system of the invention, the concentration of the antigenic or immunogenic agent is preferably less than the conventional amounts used when alternative routes of administration are employed, e.g., intramuscular. The concentration of the antigenic or immunogenic agent used in the dermal vaccine formulations of the invention (including intradermal and epidermal vaccine formulations) is 60%, preferably 50%, more preferably 40% of the concentration conventionally used in obtaining an effective immune response. Typically, the starting concentration of the antigenic or immunogenic agent in the dermal vaccine formulation of the invention (including intradermal and epidermal vaccine formulations) is the amount that is conventionally used for eliciting the desired immune response, using the conventional routes of administration, e.g., intramuscular injection. The concentration of the antigenic or immunogenic agent in the dermal vaccine formulations of the invention (including intradermal and epidermal vaccine formulations) is then adjusted, e.g., by dilution using a suitable diluent, so that an effective protective immune response is achieved, as assessed using standard methods known in the art and described herein.

The dermal vaccine formulations of the present invention (including intradermal and epidermal vaccine formulations) can be prepared as unit dosage forms. A unit dosage per vial may contain 0.1 mL to 1 mL, preferably 0.1 to 0.5 mL of the formulation. In some embodiments, a unit dosage form of the dermal vaccine formulations of the invention may contain 50 µL to 100 µL, 50 µL to 200 µL, or 50 µL to 500 µL of the formulation. If necessary, these preparations can be adjusted to a desired concentration by adding a sterile diluent to each vial. The dermal vaccine formulations of the invention are more effective in eliciting the desired immune response, and thus the total volume for dermal delivery may be less than the volume that is conventionally used.

In some embodiments, the components of the dermal vaccine formulations of the invention, e.g., the antigenic or immunogenic agent and the cocktail comprising two or more geling agents, two or more bio or mucoadhesives, two or more pre-selected excipients, or any combination thereof (herein referred to as the "cocktail"), are supplied either separately or mixed together in unit dosage form, for example, as a dry lyophilized powder or water free concentrate in a hermetically sealed container such as an ampoule or a sachette indicating the quantity of the active agent, e.g., the antigenic or immunogenic agent. In other embodiments, an ampoule of sterile diluent can be provided so that the components may be mixed prior to administration. In a specific embodiment, the cocktail may be mixed with the antigenic or immunogenic agent just prior to administration. In another specific embodiment, the cocktail may be mixed with the antigenic or immunogenic agent in an intradermal delivery device during administration. In another specific embodiment, the cocktail may be mixed with the antigenic or immunogenic agent in a dermal delivery device during administration. In another specific embodiment, the cocktail may be mixed with the antigenic or immunogenic agent in an epidermal delivery device during administration.

The invention also provides intradermal vaccine formulations that are packaged in a hermetically sealed container such as an ampoule or a sachette indicating the quantity of the components. In one embodiment, the intradermal vaccine formulation is supplied as a liquid, in another embodiment, as a dry sterilized lyophilized powder or water free concentrate in a hermetically sealed container and can be reconstituted, e.g., with water or saline to the appropriate concentration for administration to a subject.

In an alternative embodiment, the intradermal vaccine formulation is supplied in liquid form in a hermetically sealed container indicating the quantity and concentration of the components.

The intradermal vaccine formulation of the invention may be prepared by any method that results in a stable, sterile, injectable formulation. In a specific embodiment, when the molecule is a polymer, the polymer may be dissolved in an aqueous solution, e.g., water, at a temperature below the liquid-gel transition temperature of the polymer and at a concentration such that above the liquid-gel transition temperature a gelatinous matrix may be formed. The optimal concentration at which the polymer solution is formed depends on the particular polymer and is discussed below. In the same embodiment, the antigenic or immunogenic agent is dissolved in an aqueous solution, e.g., water, and combined with the polymer such that a stable, sterile, injectable formulation is formed. Alternatively, the antigenic or immunogenic agent may be particulate and dissolved in the polymeric solution such that a stable, sterile, injectable formulation is formed. For enhanced performance of the intradermal vaccine formulation of the invention, the antigenic or immunogenic agent should be uniformly dispersed throughout the gelatinous matrix, which can be achieved by dissolving the antigenic or immunogenic agent in a solution comprising the polymer at a temperature below the liquid-gel transition temperature of the polymer so that once the temperature is raised the antigenic or immunogenic agent is uniformly dispersed and embedded in the gelatinous matrix.

The intradermal vaccine formulation of the invention have particular utility for intradermal delivery of the antigenic or immunogenic agent to the intradermal compartment of a subject's skin. Preferably, the intradermal vaccine formulations of the invention are administered using any of the intradermal devices and methods disclosed in U.S. patent application Ser. No. 09/417,671, filed on Oct. 14, 1999; Ser. No. 09/606,909, filed on Jun. 29, 2000; Ser. No. 09/893,746, filed on Jun. 29, 2001; Ser. No. 10/028,989, filed on Dec. 28, 2001; Ser. No. 10/028,988, filed on Dec. 28, 2001; or International Publication No. EP 10922 444, published Apr. 18, 2001; WO 01/02178, published Jan. 10, 2002; and WO 02/02179, published Jan. 10, 2002; all of which are incorporated herein by reference in their entirety.

The intradermal vaccine formulations of the invention are administered to the intradermal compartment of a subject's skin such that the intradermal space of the subject's skin is penetrated, without passing through it. Preferably, the intradermal vaccine formulations are administered to the intradermal space at a depth of about 1.0 to 3.0 mm, most preferably at a depth of 1.0 to 2.0 mm. The intradermal vaccine formulations of the invention for intradermal delivery provide a pain-free and less invasive mode of administration as compared to conventional modes of administrations, e.g., i.m., for vaccine formulations, and therefore are more advantageous, for example, in terms of the subjects' compliance.

The epidermal vaccine formulation of the invention have particular utility for epidermal delivery of the antigenic or immunogenic agent to the epidermal compartment of a subject's skin. Preferably, the epidermal vaccine formulations of the invention are administered using any of the methods and devices disclosed in U.S. Provisional patent application Nos. 60/330,713, 60/333,162 and U.S. application Ser. Nos. 09/576,643, 10/282,231, filed Oct. 29, 2001, Nov. 27, 2001, and May 22, 2000 and Oct. 29, 2002, respectively, all of which are each hereby incorporated by reference in their entirety.

In some embodiments, the intradermal vaccine formulations are administered within 12 hours, preferably within 6 hours, within 5 hours, within 3 hours, or within 1 hour after preparation, for example, after being reconstituted from the lyophilized powder. In a preferred embodiment, the intradermal vaccine formulations are prepared for intradermal administration into a subject immediately prior to the intradermal administration, i.e., mixed with the cocktail.

The dermal vaccine formulations of the invention (including the epidermal and intradermal vaccine formulations) have little or no short term and/or long term toxicity when administered in accordance with the methods of the invention. Most preferably, the intradermal vaccine formulations of the invention when intradermally administered have little or no adverse or undesired reaction at the site of the injection, e.g., skin irritation, swelling, rash, necrosis, skin sensitization. In yet other most preferred embodiments, the epidermal vaccine formulations of the invention when epidermally administered have little or no adverse or undesired reaction at the site of the injection, e.g., skin irritation, swelling, rash, necrosis, skin sensitization.

In a specific embodiment, the intradermal vaccine formulation of the invention is preferably administered to the intradermal compartment of a subject's skin in the form of a flowable medium, e.g., a liquid, at a temperature below the physiological temperature of the subject. Preferably, the temperature at which the administration occurs is below the liquid-gel transition of the polymer in the intradermal vaccine formulation. The viscosity of the intradermal vaccine formulation increases once the formulation is introduced into the intradermal compartment of the subject's skin, such that a gelatinous matrix, i.e., an immobile solid or a semi-solid phase of the flowable injected medium that has resistance to flow, is formed. The viscosity of the gelatinous matrix is increased relative to the flowable injected medium by at least 30%, or at least 50%, or at least 60%, or at least 80%, or at least 90%.

The invention also provides a pharmaceutical pack or kit comprising an intradermal vaccine formulation of the invention. In a specific embodiment the invention provides a kit comprising, one or more containers filled with one or more of the components of the intradermal vaccine formulation of the invention, e.g., an anitgenic or immunogenic agent, a cocktail. In another specific embodiment, the kit comprises two containers, one containing an anitgenic or immunogenic agent, and the other containing the cocktail. Associated with such container(s) can be a notice in the form prescribed by a governmental agency regulating the manufacture, use or sale of pharmaceuticals or biological products, which notice reflects approval by the agency of manufacture, use or sale for human administration.

The invention further contemplates kits comprising an intradermal administration device and an intradermal vaccine formulation of the invention as described herein. The invention further contemplates kits comprising a dermal administration device and a dermal vaccine formulation of the invention as described herein. The invention further contemplates kits comprising an epidermal administration device and an epidermal vaccine formulation of the invention as described herein.

The invention encompasses a method for immunization and/or stimulating an immunological immune response in a subject comprising intradermal delivery of a single dose of an intradermal vaccine formulation of the invention to a subject, preferably a human. In some embodiments, the invention encompasses one or more booster immunizations.

It will be appreciated by one skilled in the art that the principles set forth herein are also applicable for delivering vaccine formulations beyond the stratum corneum for deposition into the epidermal compartment of a subject's skin. Methods and devices for abrading the skin, and particularly, the stratum corneum of the skin are known in the art and encompassed in the present invention for depositing a substance into the epidermal compartment, such as those disclosed in U.S. Provisional patent application Nos. 60/330, 713, 60/333,162 and U.S. application Ser. Nos. 09/576,643, 10/282,231, filed Oct. 29, 2001, Nov. 27, 2001, and May 22, 2000 and Oct. 29, 2002, respectively, all of which are each hereby incorporated by reference in their entirety.

5.1 Immunogenic Compositions 5.1.1 Geling Agents

In some embodiments, the cocktails which may be used in the dermal vaccine formulations of the invention (including intradermal and epidermal vaccine formulations) comprise a geling agent that polymerizes or gels once administered to the dermal compartment of a subject's skin. Such geling agents, preferably create a semi-solid to solid matrix, which may be two or three dimensional that may allow interaction of the antigenic or immunogenic agent with the biological and immunological space of the dermal compartment, specifically with the immune cells residing therein. In some embodiments, the geling agents enhance the presentation and/or availability of the antigenic or immunogenic agent with the biological and immunological space of the dermal compartment. Geling agents suitable for the dermal vaccine formulations of the invention (including intradermal and epidermal vaccine formulations) preferably break down and/or degrade within the body of the subject to which they are administered, and do not result in any toxic, deleterious, or undesired effects on the subject.

In some embodiments, the geling agent may not gel and merely thickens, i.e., the viscosity of the molecule is increased as assessed visually. Regardless of the physical state of the geling agent below the liquid-gel transition temperature, the viscosity of the geling agent may increase by at least 30%, at least 50%, at least 60%, at least 80%, at least 90%, or at least 99% at a temperature above the transition temperature, e.g., at a physiological temperature.

The geling agent used in the dermal vaccine formulations of the invention (including intradermal and epidermal vaccine formulations) preferably undergoes a thermally induced physical transition from a liquid to a gel as the temperature of the dermal vaccine formulation is increased over a temperature range consisting of a first temperature and a second temperature. Preferably, the first temperature is in a range from 1° C. to 20° C. and the second temperature is in the range of 25° C. to 37° C.

The geling agent used in the dermal vaccine formulations of the invention (including intradermal and epidermal vaccine formulations) preferably undergoes a thermally induced liquid-gel transition at a physiological temperature of the subject to which the dermal vaccine formulations of the invention are administed. In a specific embodiment, when the subject is human, the geling agent used in the dermal vaccine formulations of the invention (including intradermal and epidermal vaccine formulations) is selected and formulated such that the dermal vaccine formulation undergoes a thermally induced liquid-gel transition at a temperature below 40° C., preferably below 37° C. In some embodiments, the geling agent undergoes a thermally induced liquid-gel transition at a temperature from about 10° C. to about 37° C., preferably at a temperature from about 25° C. to 37° C. Preferably, the liquid-gel transition of the dermal vaccine formulation of the invention is accompanied by an increase in the viscosity of the dermal vaccine formulation.

In a specific embodiment, the geling agent used in the dermal vaccine formulations of the invention is a polymer. Any biocompatible, biodegradable polymer may be used that as formulated in the dermal vaccine formulation of the invention is capable of imparting the desired liquid-gel transition property to the dermal vaccine formulation. Non-limiting examples of some polymers useful for preparing the dermal vaccine formulations of the invention (including intradermal and epidermal vaccine formulations) include polyethers, preferably polyoxyalkylene block copolymers, more preferably polyoxyalkylene block copolymers including polyoxyethylene-polyoxypropylene block copolymers referred to herein as POE-POP block copolymers, such as PLURONIC® F68, PLURONIC® F127, PLURONIC® L121, and PLURONIC® 101, and TETRONIC®0 T1501; and poly (ether-ester) block copolymers. Some examples of the above-identified polymers are disclosed in U.S. Pat. Nos. 5,702,717 and 5,861,174; which are incorporated herein by reference in their entirety.

The invention encompasses dermal vaccine formulations (including intradermal and epidermal vaccine formulations) comprising more than one of the above identified polymers and/or other polymers that provide the desired characteristics, e.g., enhanced protective immune response when delivered to the intradermal compartment of a subject's skin. In some embodiments, the dermal vaccine formulation (including intradermal and epidermal vaccine formulations) may further comprise other polymers and/or other additives, to the extent the inclusion of the additional components is not inconsistent with performance requirements of the dermal vaccine formulation of the invention. Furthermore, these polymers may be combined, e.g., mixed with other polymers or other additives, such as sugars, to vary the liquid-gel transition temperature, typically in aqueous solutions.

Polyoxyalkylene block copolymers (PLURONIC® copolymer) are particularly preferred to use as the polymer in accordance with the invention. A polyoxyalkylene block copolymer is a polymer including at least one block (i.e., a polymer segment) of a first polyoxyalkylene and at least one block of a second polyoxyalkylene, although other blocks may be present as well.

In a specific embodiment of the invention, the polyoxyalkylene block copolymer comprises at least one block of a first polyoxyalkylene and at least one block of a second polyoxyalkylene. In yet another specific embodiment, the first polyoxylakylene is polyoxyethylene and the second polyoxyalkylene is polyoxypropylene.

POE-POP block copolymers are one class of preferred polyoxyalkylene block copolymers for use as the biocompatible polymer in the dermal vaccine formulations of the invention (including intradermal and epidermal vaccine formulations). These polymers can be designed and synthesized using variable amounts of the POE-POP blocks and with differential arrangement of the POP and POE blocks. Any of the polyoxyalkylene block copolymers known in the art are encompassed within the methods and formulations of the instant invention. For a review of polyoxyalkylene block copolymers, their molecular structure, synthesis, and purification see, e.g., Newman et al., 1998, *Advanced Drug Delivery Reviews* 32: 199-223; Verheul & Snippe, 1992, *Res. Immunol.* 143(5): 512-9; Hunter et al., 1994 *AIDS Res. and Human Retroviruses,* 10: Suppl. 2, S95-8; Newman et al., 1998, *Crit. Rev. Ther. Drug. Carrier Syst.* 15(2): 89-142; Kabanov et al., 2002 *Advanced Drug Delivery Review* 54: 223-233; Moghimi et al., 2000 *TIBTECH,* 18: 412-20; all of which are incorporated herein by reference in their entirety.

The polyoxyalkylene copolymers that may be used as a geling agent in the dermal vaccine formulations of the invention (including intradermal and epidermal vaccine formulations) may be triblocks, e.g., L81, L92, L101, L121, L122, L141, L180, L185, reversed triblocks, e.g., 25R1, 31R1, octablocks, e.g., T1101, T1301, T1501, reversed octablocks, e.g., T130R1, T130R2, T150R1. The invention encompasses polyoxyalkylene copolymers wherein the orientation and size of the POP and POE blocks may be varied using common methods known in the art to achieve a desired surfactant property, depending on the intradermal vaccine formulation being prepared. In a specific embodiment, the polyoxyalkylene copolymer used in the dermal vaccine formulation (including intradermal and epidermal vaccine formulations) and methods of the invention is a linear molecule with the polymer blocks organized as POE-POP-POE The invention encompasses low molecular weight polyoxyalkylene copolymers as well as high molecular weight polyoxyalkylene copolymers. The low molecular weight copolymers may be about 2 to 6 KDa. The high molecular weight copolymers may be about 12 to 15 KDa. Preferably, the copolymers used within the dermal vaccine formulations of the invention have adjuvant activity, e.g., enhance the therapeutic efficacy of a vaccine formulation. In a preferred embodiment, the polyoxyalkylene copolymers used in the dermal vaccine formulations of the invention are about 12 to 15 KDa, with adjuvant activity. In yet another preferred embodiment, the polyoxyalkylene copolymers used in the dermal vaccine formulation of the invention (including intradermal and epidermal vaccine formulations) has a low POE concentration, preferably 10%, more preferably 8%, most preferably 5% so that optimal adjuvant activity is achieved. In a most preferred embodiment, the POE concentration of the polyoxyalkylene is no more than 5%.

The invention encompasses any of the PLURONIC® copolymers that are commercially available, e.g., TITERMAX® (CytRx Corporation, Atlanta, Ga.); Syntex Adjuvant formulation (Syntex Res., Palo Alto, Calif.). In preferred embodiments, the invention encompasses PLURONIC® copolymers manufactured by Wyandotte Chemical Corporation and BASF Performance Chemicals (Parsiponny, N.J.), including, but not limited to, L31, L81, L92, L101, L121, L122, P102, F108, L141, L180, L185, P1004, and P1005.

In some embodiments, the invention encompasses the use of high molecular weight CRL copolymers, such as those commercially available from CytRx Corporation (Norcross, Ga.). The CRL copolymers are similar to PLURONIC® copolymers in orientation of the POE and POP blocks, however, they are significantly larger in size. CRL copolymers containing 9000-20,000 dalton POP cores flanked by POE blocks that constitute 2.5-20% of the total molecular weight. Any of the CRL copolymers known in the art are encompassed in the methods and dermal vaccine formulations of the invention.

The concentration of the polymer used in the dermal vaccine formulations (including intradermal and epidermal vaccine formulations) of the invention may be at least 10% (w/v), at least 15% (w/v), at least 20% (w/v), at least 25% (w/v), or at least 30% (w/v). In some embodiments, the concentration of the polymer used in the dermal vaccine formulations of the invention is less than 10% (w/v). In other embodiments, the concentration of the polymer used in the dermal vaccine formulations of the invention is more than 30% (w/v). The concentration of the polymer used in the dermal vaccine formulations of the invention (including intradermal and epidermal vaccine formulations) is preferably the concentration at which an aqueous solution of the polymer gels, i.e., forms a semi-solid to solid two or three dimensional matrix at a physiological temperature, e.g., at 37° C. In some embodiments, the polymer used in the dermal vaccine formulations of the invention gels within 20 minutes or less, preferably within 10 minutes or less, and most preferably within 5 minutes or less at a physiological temperature, e.g., at 37° C., as assessed by visual inspection. Preferably, the concentration at which an aqueous solution of the polymer gels is also the concentration at which the therapeutic efficacy of the dermal vaccine formulation of the invention is enhanced as determined using standard methods known in the art, e.g., as determined by the antibody response to the antigenic or immunogenic agent, relative to a control formulation, e.g., a formulation comprising the antigenic or immunogenic agent alone.

An exemplary method for determining the concentration of the polymer for the intradermal vaccine formulations of the invention may comprise the following: an aqueous stock solution of the polymer is prepared; the solution is then incubated, preferably, by mechanical agitation, e.g., magnetic stirring, at a temperature below the liquid-gel transition temperature, e.g., on ice at 4° C.; the pH of the solution is adjusted to a physiological pH, ranging from 7.0 to 7.4, preferably to 7.2; the solution is then sterilized, preferably by filtration, e.g., using a 0.2 micron Gelman Acrodisc PF Syringe Filter # 4187; the solution is then incubated at 37° C., e.g., by placing it in a 37° C. water bath; and the solution is visually monitored. Specifically, the viscosity of the solution is visually monitored. In some embodiments, the solution gels within 5 minutes or less. In other embodiments, the solution gels within 20 minutes or less, 15 minutes or less, 10 minutes or less. If the solution does not gel within the time frame specified above, the concentration of the polymer may be adjusted so that a higher percentage of the polymer is used. The concentration of the polymer may be adjusted so that the solution preferably gels, as determined by visual inspection of the solution at a physiological temperature, e.g., 37° C.

In a specific embodiment, the invention encompasses the LUTROL® F grade chemicals supplied by BASF Corporations including, but not limited to, F127, F68, F87, and F108. Preferably, the LUTROL® F grade chemicals polymerize to form a gel at a physiological temperature, e.g., temperature ranging from 25° C. to 37° C., at a concentration ranging from about 10% (w/v) to 20% (w/v), from about 10% (w/v) to 25% (w/v), from about 10% (w/v) to about 30% (w/v), or from about 10% (w/v) to about 35% (w/v). Although not intending to be bound by a particular mechanism of action, polymerization of the LUTROL® chemicals results in cross-linking, either covalently or non-covalently, of the chemical to form a two or three dimensional gelatinous matrix. The degree of polymerization may range from 5% to 50%, preferably 60% to 80%, most preferably about 90%.

In a specific embodiment, the LUTROL® F grade used in the intradermal vaccine formulations and methods of the invention is F127, which forms a gelatinous matrix at a temperature of 37° C. and at a concentration of 20% (w/v). The polymerization of the F127 PLURONIC® may be chemically and/or thermally induced. Preferably, the polymerization of the F127 PLURONIC® is thermally induced.

In another specific embodiment, the LUTROL® F grade used in the dermal vaccine formulations (including intradermal and epidermal vaccine formulations) and methods of the invention is F68, which forms a gelatinous matrix at a temperature of 37° C. and at a concentration of more than 30% (w/v). In yet another specific embodiment, the LUTROL® F grade used in the dermal vaccine formulations and methods of the invention is F108, which forms a gelatinous matrix at a temperature of 37° C. and at a concentration of 20% (w/v).

In most preferred embodiments, the geling agent used in the intradermal vaccine formulations and methods of the invention polymerizes, e.g., forms a gel, at body temperature, i.e., a temperature ranging from 25°-37° C. Polymerization of the geling agent may be chemically and/or thermally induced. Although not intending to be bound by a particular mode of action, polymerization of the geling agent involves cross-linking, either covalently or non-covalently, of the polymer to form a two or three dimensional gelatinous matrix. The degree of polymerization may range from 5% to 50%, preferably 60% to 80%, most preferably about 90%. The geling agent used in accordance with the methods of the invention may be solid, liquid or a paste prior to the thermal and/or chemical change.

In most preferred embodiments, the geling agent used in the dermal vaccine formulations of the invention has one or more biological properties of an adjuvant. As used herein, the term "adjuvant" refers to an auxiliary compound that when present in an intradermal vaccine formulation assists the active molecule, e.g., an immunogenic or antigenic agent in the dermal vaccine formulation, in producing the desired physiological response, e.g., enhancing the immune response to an antigenic or immunogenic agent. In yet other embodiments, the geling agent used in the dermal vaccine formulations of the invention has muco or bioadesive properties.

The amount of the geling agent that may be used in the dermal vaccine formulation of the invention is typically from about 1% to 50% (w/v) of the intradermal vaccine formulation, from about 15% (w/v) to about 30% (w/v), preferably from about 10% (w/v) to about 30% (w/v).

5.1.2 Muco or Bioadhesives

In certain embodiments, the cocktail used in the dermal vaccine formulations of the invention (including intradermal and epidermal vaccine formulations) comprises a muco or bioadhesive molecule which may facilitate adherence of the antigenic or immunogenic agent to the biological and immunological surface of the dermal compartment, i.e., the surface of the immune cells. As used herein, bioadhesive or mucoadhesive means having the ability to adhere to a biological surface for an extended period of time. Preferably, such mucoadhesion or bioadhesion results in an enhancement of biological activity of the intradermal vaccine formulations, e.g., enhanced therapeutic efficacy. Although not intending to be bound by a particular mechanism of action, muco or bioadhesion allows prolonged exposure of the immunogenic or antigenic agent in the intradermal vaccine formulations of the invention to the cells of the immune system, e.g., antigen presenting cells, residing in the intradermal compartment. The adhesion property offered by the muco or bioadhesive molecule most likely leads to a prolonged residence time of the antigenic or immunogenic agent in the dermal compartment. Delivery of the antigenic or immunogenic agent benefits from mucoadhesion or bioadhesion by allowing adherence or "sticking" of the antigenic or immunogenic agent to the targeted biological surface, i.e., the dermal space. Furthermore, the antigenic or immunogenic agent may be held at the targeted biological surface thus allowing slow release of the antigenic or immunogenic agent, i.e., a depot effect.

Muco or bioadhesive molecules that may be used in the dermal vaccine formulations of the invention include, but are not limited to, polymers, e.g., polycarbophils polyacrylic acid (PAA), carobopols, capricol, Carbopol EX55, carbomers, polysaccharides, hyaluronic acid, chitosans; lectins; cellulose, methylcellulose, carboxymethylcellulose, hydroxypropyl methyl cellulose, sodium alginate, gelatin, pectin, acacia, povidone. For a review of available mucoadesive and bioadhesive molecules see reviews by Robinson et al., *Annals New York Academy of Sciences,* 307-314; Haas et al., 2002, *Expert Opin. Biol. Ther.* 2(3): 287-298; Woodley, 2001, *Clin. Pharmacokin.* 40(2): 77-84; Peppas et al., 1996, *Biomaterials* 17; 1553-61; all of which are incorporated herein by reference in their entirety.

The concentration of the bioadhesive or mucoadhesive molecule in the dermal vaccine formulations of the invention may be 0.1% (w/v) to 1% (w/v), 0.1% (w/v) to 5% (w/v), or 0.1% (w/v) to 10% (w/v), or 0.01% (w/v) to 10% (w/v), or 0.01% (w/v) to 0.04% (w/v). The concentration of the muco or bioadhesive molecule used in the intradermal vaccine formulations of the invention is preferably the concentration at which the therapeutic efficacy of the intradermal vaccine formulation of the invention is enhanced, e.g., as determined by the antibody response to the antigenic or immunogenic agent, relative to a control formulation, e.g., a formulation comprising the antigenic or immunogenic agent alone.

5.13 Excipients

As used herein, and unless otherwise specified, the term "excipient" means an ingredient or an additive in a pharmaceutical composition, which itself possesses no pharmacological or biological activity for which the composition is intended. Excipients used in the methods of the present invention are pre-selected excipients. As used herein, "pre-selected" excipients encompass traditional, non-traditional, and any other exicipient that, in combination with one another, has an adjuvant activity when delivered to a patient. It has been unexpectedly discovered that specific combinations of two or more of these excipients or in combination with another agent disclosed herein, when co-administered with an antigenic or immunogenic agent, act as an adjuvant, i.e., enhance the immune response to the antigenic or immunogenic agent in a subject receiving such composition as compared to a subject receiving the composition without the combination of excipients.

In some embodiments, without being bound by a particular mechanism of action, when the combination of excipients of the instant invention is administered at the concentrations and by the delivery routes in accordance with the methods of the invention, they may exhibit non-specific adjuvant activity, perhaps through promotion of mechanical damage, mild irritation, or stretching of the skin. In some embodiments, without being bound by a particular mechanism of action, once the combination of excipients are delivered to a subject in accordance with the present invention, they may act as a skin irritant leading to the recruitment of antigen presenting cells at the site of the injection, and thus act as an adjuvant, i.e., enhance the immune response to the immunogenic composition.

As used herein, when the excipients as an irritant, they cause a reversible and asymptomatic inflammatory effect on tissue by chemical action at the site of contact and yet is not corrosive. Inflammatory effect at the site of injection involves an influx of blood at the site of injection and may be marked by swelling, redness, heat, and/or pain. One skilled in the art can determine if an excipient is a skin irritant using, for example, the methods disclosed in Code of Federal Regulation (Title 16, Vol. 2; 6 CFR 1500.41, which is incorporated herein by reference in its entirety). According to 6 CFR 1500.41, a chemical is a skin irritant if, when tested on the intact skin of albino rabbits by the methods of 16 CFR 1500.41 for four hours exposure or by other appropriate techniques, it results in an empirical score of five or more. Preferably, the excipients used in the methods of the invention have a score of 5 or less, more preferably a score of 4 or less, and most preferably a score of 3 or less. When an excipient of the invention is characterized as a skin irritant, one or more other excipients that are not skin irritants may be used in the immunogenic compositions to reduce the skin irritation. In a specific embodiment, in order to determine if the immunogenic composition of the invention results in skin irritation, once the immunogenic composition, e.g., a vaccine, is delivered to a subject, e.g., an animal, the site of the injection is visually checked within one hour of the immunization, at 24 hours and again at 21 days. Any observation other than the initial "Bleb" which resolves in hours, would be noted as unacceptable. In a specific embodiment, when a DNA immunogenic agent, e.g., pDNA-HA is delivered to a subject, the site of the injection is checked within one hour of the immunization (prime or boost), 24 hours afterwards, at 21 days just before boost, 24 hours after the boost and 21 days after the boost (actual day 42 of schedule).

Excipients are typically classified into subclasses according to their function. Excipients used in the immunogenic compositions of the invention may have one or more functions. Several subclasses of excipients are known in the art and are encompassed in the present invention. See, e.g., Ansel et al., *Pharmaceutical Dosage Forms and Drug Delivery System*, 6$^{th}$ Ed., pp. 110-133, Williams & Wilkins (1995), which is incorporated herein by reference in its entirety. For example, an excipient can be categorized as a stabilizer, a preservative, a solvent, a surfactant or detergent, a suspending agent, a tonicity agent or a vehicle. In the case of vaccines, ingredients for growth medium, which are used to facilitate or maintain the growth of the immunogen, are commonly used as excipients. Some excipients have more than one function and can be used for multiple purposes. It will be apparent to those of ordinary skill in the art that these subclasses are not an exhaustive list of all available excipients, thus other types of excipients can also be used in accordance with the immunogenic compositions and methods of the invention. Additional categories and examples of excipients are provided in *Handbook of Pharmaceutical Excipients*, 2003 (4$^{th}$ ed., American Pharmaceutical Association, London), the entirety of which is incorporated herein by reference.

In one embodiment, at least one of the excipients used in the immunogenic compositions of the invention is a stabilizer. As used herein, a stabilizer is a chemical agent that increases the stability of a pharmaceutical composition. As used herein, a stable composition refers to a composition that undergoes minimal to no detectable level of degradation and/or aggregation of the antigenic or immunogenic agent, and can be stored for an extended period of time with no loss in biological activity, e.g., antigenicity or immunogenicity of the antigenic agent. Preferably, the immunogenic compositions of the present invention exhibit stability at the temperature ranges of 2° C.-8° C., preferably at 4° C., for at least 2 years, as assessed by high performance size exclusion chromatography (HPSEC). Preferably, the immunogenic compositions of the present invention to have low to undetectable levels of aggregation and/or degradation of the antigenic or immunogenic agent, after the storage for the defined periods as set forth above. Preferably, no more than 20%, no more than 10%, no more than 5%, no more than 4%, no more than 3%, no more than 2%, no more than 1%, and most preferably no more than 0.5%, of the antigenic or immunogenic molecule forms an aggregate or degrades as measured by HPSEC, after the storage for the defined periods as set forth above. In most preferred embodiments, the immunogenic compositions of the present invention will exhibit almost no loss in biological activity of the antigenic or immunogenic agent during a prolonged storage under the conditions described above, as assessed by standard methods known in the art. The immunogenic compositions of the present invention retain after the storage for the above-defined periods more than 80%, more than 85%, more than 90%, more than 95%, more than 98%, more than 99%, or more than 99.5% of the initial biological activity prior to the storage.

Depending on the mechanism by which an excipient stabilizes the composition, the stabilizers can be further categorized into an acidifying or alkalinizing agent, an adsorbent, an air displacement agent, an antioxidant, a buffering agent, a chelating agent or a humectant, which are all encompassed within the instant invention. An acidifying agent as used herein stabilizes a pharmaceutical composition by providing an acidic medium for the active ingredient in the composition, i.e., the antigenic or immunogenic agent, that is otherwise labile in an alkaline condition. Examples of an acidifying agent include, but are not limited to, acetic acid, citric acid, fumaric acid, hydrochloric acid, nitric acid and sodium acetate. An alkalinizing agent stabilizes the composition by providing an alkaline medium for the active ingredient in the composition, i.e., the antigenic or immunogenic agent that are labile in an acidic environment. Examples of an alkalinizing agent include, but are not limited to, ammonia solution, ammonium carbonate, mono-, di- or tri-ethanolamine, potassium hydroxide, sodium borate, sodium carbonate, sodium hydroxide and trolamine.

In a specific embodiment, at least one of the excipients used in the immunogenic composition of the invention is an adsorbent. An adsorbent as used herein is an agent capable of allowing other molecules to adhere or adsorb onto its surface by physical and/or chemical means. Examples of an adsorbent include, but are not limited to, cellulose, charcoal and gelatin.

In another embodiment, at least one of the excipients used in an immunogenic composition of the invention is an air displacement agent. An air displacement agent as known to one skilled in the art is employed to displace air in a hermetically sealed container to enhance the stability of a pharmaceutical composition. Examples include, but are not limited to, nitrogen gas.

In another embodiment, at least one of the excipients used in an immunogenic composition of the invention is an antioxidant. Although not intending to be bound by a particular mechanism of action an antioxidant stabilizes a pharmaceutical composition by inhibiting oxidation, and thus preventing the deterioration of the composition by the oxidative process. Examples of an antioxidant for use in the immunogenic compositions of the invention include, but are not limited to, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite and sodium sulfite.

In another embodiment, at least one of the excipients used in an immunogenic composition of the invention is a buffering agent. Although not intending to be bound by a particular mechanism of action, a buffering agent stabilizes a pharmaceutical composition by providing resistance to alterations in pH for example, upon dilution or addition of acid or alkali. Examples of buffering agents that may be used in the immunogenic compositions of the invention include, but are not limited to, glycine, potassium metaphosphate, potassium phosphate, monobasic sodium acetate, and anhydrous or dihydrate sodium citrate.

In another embodiment, at least one of the excipient used in an immunogenic composition of the invention is a chelating agent. Although not intending to be bound by a particular mechanism of action, a chelating agent stabilizes a pharmaceutical composition by forming a stable, water soluble complex with one or more metals, e.g., heavy metals. Heavy metals are typically critical in enzymatic activity of proteases, and thus chelating agents limit the activity of the proteases by sequestering a metal needed for their enzymatic activity. Examples of a chelating agents that may be used in the compositions of the invention include, but are not limited to, edetate disodium and edetic acid.

In another embodiment, at least one of the excipients used in an immunogenic compositions of the invention is a humectant. A humectant is an agent that prevents the drying out of preparations by retaining moisture. Examples of humectants that may be used in the immunogenic compositions of the invention include, but are not limited to, glycerin, propylene glycol and sorbitol. In a specific embodiment, at least one the excipients of this invention is sorbitol. Preferably, the concentration of sorbitol used in the immunogenic compositions of the invention may be from about 0.5% w/v to about 25% w/v, from about 3% w/v to about 15% w/v, or from about 5% w/v to about 10% w/v.

In another embodiment, at least one of the excipientss used in an immunogenic composition of this invention is a preservative. Although not intending to be bound by a particular mechanism of action a preservative is a substance that prevents the growth of exogenous organisms in a pharmaceutical composition. Preservatives include, for example, antifungal agents, i.e., an agent that prevents the growth of fungi, and antimicrobial agents, i.e., an agent that prevents the growth of microorganisms including viruses. Examples of antifungal agents that may be used in the immunogenic compositions and methods of the invention include, but are not limited to, amphotericin B, benzoic acid, methyl-, ethyl-, propyl- or butyl-paraben, sodium benzoate and sodium propionate. Examples of antimicrobial agents that may be used in the immunogenic compositions and methods of the invention include, but are not limited to, amiprilose, benzalkonium chloride, benzethonium chloride, benzyl alcohol, betapropiolactone, cetylpyridium chloride, chlorobutanol, chlortetracycline, EDTA, formaldehyde, gentamicin, kanamycin, neomycin, phenol, phenoxyethanol, phenylethyl alcohol, phenylmercuric nitrate, polymyxin B, streptomycin, thimerosal, tri-(n)-butyl phosphate.

In another embodiment, at least one of the excipients used in an immunogenic compositions of the invention is a solvent. Examples of solvents include, but are not limited to, ethanol.

In another embodiment, at least one of the excipients used in an immunogenic composition of the invention is a surfactant, i.e., surface active agent. Although not intending to be bound by a particular mechanism of action a surfactant absorbs to a surface or an interface and reduces surface or interfacial tension. A surfactant may be used as a wetting agent, detergent or emulsifying agent. Examples of a surfactants that may be used in the compositions of the invention include, but are not limited to, benzalkonium chloride, magnesium stearate, nonoxynol 10, oxtoxynol 9 (Triton N-101), poloxamers such as poloxamer 124, 188 (LUTROL® F 68), 237, 388 or 407 (LUTROL® F 127), polysorbate 20 (TWEEN™ 20), polysorbate 80 (TWEEN™ 80), sodium lauryl sulfate, sorbitan monopalmitate and Triton X-100.

In a specific embodiment, at least one of the excipients used in an immunogenic composition of the invention is LUTROL® (e.g., LUTROL® F 127). Preferably, the concentration of LUTROL® used in the immunogenic compositions of the invention may be from about 1% w/v to about 25% w/v, from about 3% w/v to about 15% w/v, or from about 5% w/v to about 10% w/v. Surfactants are typically used in the preparation and manufacturing of immunogenic compositions, particularly vaccines. In such cases, residual concentrations of the surfactant may be found in the final immunogenic composition, left over from the preparation or manufacturing of the composition. Such residual concentrations are too low to result in the adjuvant activity observed with the immunogenic compositions of the invention. Examples of such surfactants are octyl- or nonylphenoxy polyoxyethanols (e.g., Triton™ series), polyoxyethylene sorbitan esters (e.g., TWEEN™ series), and polyoxyethylene esters or ethers; Octylphenoxy polyoxyethanols and polyoxyethylene sorbitan esters including t-octylphenoxypolyoxyehtnaol; and Polyoxyethylene sorbitan esters including poloxyethylene sorbitan monooleate; Triton X-45, Triton X-102, Triton X-114, Triton X-165, Triton X-205, Triton X-305, Triton N-57, Triton N-101, Triton N-128, Breij 35, Laureth-9, Steareth-9, TWEEN™ 80. (For a list of surfactants see, e.g., *Surfactant Systems*, eds., Attwood and Florence, 1983, Chapman and Hall, which is incorporated herein by reference in its entirety).

In another embodiment, at least one of the excipients used in an immunogenic composition of the invention is a suspending agent. Although not intending to be bound by a particular mechanism of action, a suspending agent increases the viscosity of the composition by for example reducing the rate of sedimentation of particles dispersed throughout a vehicle in which they are not soluble. Examples of suspending agents that may be used in the compositions of the invention include, but are not limited to, agar, bentonite, carbomer (e.g., Carbopol), carboxymethylcellulose sodium, gelatin, hydroxyethyl cellulose, hydroxypropyl cellulose, hydroxypropyl methylcellulose, kaolin, methylcellulose, tragacanth and veegum.

In a specific embodiment, at least one of the excipients used in the composition of the invention is methylcellulose. Preferably, the concentration of methylcellulose used in the immunogenic compositions of the invention may be from about 0.001% w/v to about 1% w/v, from about 0.01% w/v to about 0.5% w/v, or from about 0.02% w/v to about 0.1% w/v.

In another embodiment, at least one of the excipients used in an immunogenic composition of the invention is a tonicity agent. Tonicity agents are particularly desired in the immunogenic compositions of the invention as they provide a solution with osmotic characteristics similar to physiologic fluid, and are thus optimal for injectable compositions of the invention. Examples of a tonicity agent that may be used in the immunogenic compositions of the invention include, but are not limited to, dextrose, glucose and sodium chloride.

In another embodiment, at least one of the excipients used in an immunogenic composition of the invention is a vehicle. As used herein, vehicle is a carrying agent for a substance in a pharmaceutical composition. Vehicles are frequently used in formulating a variety of compositions for oral and parenteral administration. Vehicles for use in the methods and immunogenic compositions of the invention may be aqueous or oleaginous vehicles. Examples of a vehicle which may be used in the immunogenic compositions of the invention include, but are not limited to, corn oil, mineral oil, peanut oil, sesame oil, bacteriostatic sodium chloride injection and bacteriostatic water.

In another embodiment, at least one of the excipients used in an immunogenic composition of the invention is a growth medium ingredient. Growth medium ingredients are particularly useful when the composition is a vaccine. Examples of growth medium ingredients that may be used in the immunogenic compositions and methods of the invention include, but are not limited to, amino acids, bactopeptone, bovine albumin, bovine serum, egg protein, human serum albumin, mouse serum proteins, MRC-5 cellular protein, ovalbumin, vitamins and yeast proteins.

Other compounds or agents such as, but not limited to, serum protein (e.g., apo-transferrin, fetuin), aprotinin, glycolic acid (a skin exfoliate), mannose and urea, may be used for the combination of excipients. Any supplemental protein may possess an adjuvant activity when used in accordance with the methods of the present invention and delivered to a subject. Supplemental proteins are particularly useful as adjuvants for DNA immunogens.

In a specific embodiment, at least one of the excipients used in an immunogenic composition of the invention is urea. Preferably, the concentration of urea used in the immunogenic compositions of the invention may be from about 0.01% w/v to about 10% w/v, from about 0.1% w/v to about 5% w/v, or from about 0.2% w/v to about 1% w/v.

In one specific embodiment, the immunogenic composition of the invention comprises the combination of a surfactant and a humectant. A specific combination is LUTROL® and sorbitol. Preferably, the concentration of LUTROL® used in the immunogenic compositions of the invention may be from about 1% w/v to about 25% w/v, from about 3% w/v to about 15% w/v, or from about 5% w/v to about 10% w/v. Preferably, the concentration of sorbitol used in the immunogenic compositions of the invention may be from about 0.5% w/v to about 25% w/v, from about 3% w/v to about 15% w/v, or from about 5% w/v to about 10% w/v.

In another specific embodiment, the immunogenic composition of the invention comprises the combination of a surfactant and a suspending agent. A specific combination is LUTROL® and methylcellulose. Preferably, the concentration of LUTROL® used in the immunogenic compositions of the invention may be from about 1% w/v to about 25% w/v, from about 3% w/v to about 15% w/v, or from about 5% w/v to about 10% w/v. Preferably, the concentration of methylcellulose used in the immunogenic compositions of the invention may be from about 0.001% w/v to about 1% w/v, from about 0.01% w/v to about 0.5% w/v, or from about 0.02% w/v to about 0.1% w/v.

In another specific embodiment, the immunogenic composition of the invention comprises the combination of a surfactant, in particular, LUTROL® , and urea. Preferably, the concentration of LUTROL® used in the immunogenic compositions of the invention may be from about 1% w/v to about 25% w/v, from about 3% w/v to about 15% w/v, or from about 5% w/v to about 10% w/v. Preferably, the concentration of urea used in the immunogenic compositions of the invention may be from about 0.01% w/v to about 40% w/v, from about 0.1% w/v to about 10% w/v, or from about 0.2% w/v to about 1% w/v.

In another embodiment, at least one of the excipients used in the immunogenic composition of this invention is a geling agent, such as PLURONIC® or Poloxamer, including, but not limited to, PLURONIC® F-127, PLURONIC® F-68, and PLURONIC® F108.

In another embodiment, at least one of the excipients used in the immunogenic composition of this invention is a mucoadhesive or bioadhesive, such as, but not limited to, polycarbophils, polyacrylic acid, carbopols, carbopol EX55, capricol, carbomers, polysaccharides, hyaluronic acid, chitosans, lectins, cellulose, methylcellulose, carboxymethylcellulose, hydroxypropyl methyl cellulose, sodium alginate, gelatin, pectin, acacia, and povidone. In a specific embodiment, at least one of the excipients used in the composition of the invention is chitosan, methylcellulose, or gelatin.

The excipients used in the immunogenic compositions of the invention can exist in a liquid, gas or solid form. Two or more excipients are used in combination to achieve an additive or a synergistic effect. In one embodiment, the concentration of the excipient in the immunogenic compositions of the invention does not include the residual concentration of the excipient that may be present from the preparation or manufacturing of the composition prior to preparation of the immunogenic composition in accordance with the methods of the instant invention.

5.2 Immunogenic or Antigenic Agent

Antigenic or immunogenic agents that may be used in the dermal vaccine formulations of the invention (including intradermal and epidermal vaccine formulations) include antigens from an animal, a plant, a bacteria, a protozoan, a parasite, a virus or a combination thereof. The antigenic or immunogenic agent for use in the intradermal vaccine formulations of the invention may be any substance that under appropriate conditions results in an immune response in a subject, including, but not limited to, polypeptides, peptides, proteins, glycoproteins, and polysaccharides.

The dermal vaccine formulations of the invention may comprise one or more antigenic or immunogenic agents. The amount of the antigenic or immunogenic agent used in the dermal vaccine formulations of the invention may vary depending on the chemical nature and the potency of the antigenic or immunogenic agent. Typically, the starting concentration of the antigenic or immunogenic agent in the dermal vaccine formulation of the invention is the amount that is conventionally used for eliciting the desired immune response, using the conventional routes of administration, e.g., intramuscular injection. The concentration of the antigenic or immunogenic agent in the dermal vaccine formulations of the invention is then adjusted, e.g., by dilution using a diluent, so that an effective protective immune response is achieved as assessed using standard methods known in the art and described herein. The concentration of the antigenic or immunogenic agent used in the dermal vaccine formulations of the invention is 60%, preferably 50%, more preferably 40% of the concentration conventionally used in obtaining an effective immune response.

In a specific embodiment, the antigenic or immunogenic agent may be any viral peptide, protein, polypeptide, or a fragment thereof derived from a virus including, but not limited to, RSV-viral proteins, e.g., RSV F glycoprotein, RSV G glycoprotein, influenza viral proteins, e.g., influenza virus neuraminidase, influenza virus hemagglutinin, herpes simplex viral protein, e.g., herpes simplex virus glycoprotein including for example, gB, gC, gD, and gE. Bacterial examples include the chlamydia MOMP and PorB antigens.

In other embodiments, the antigenic or immunogenic agent for use in the dermal vaccine formulations of the invention may be an antigen of a pathogenic virus, including as examples and not by limitation: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory syncytial virus), and metapneumovirus (e.g., avian pneumovirus and human metapneumovirus)), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

The antigenic or immunogenic agent used in the dermal vaccine formulations of the invention may be an infectious disease agent including, but not limited to, influenza virus hemagglutinin (Genbank accession no. JO2132; Air, 1981, *Proc. Natl. Acad. Sci. USA* 78:7639-7643; Newton et al., 1983, *Virology* 128:495-501), human respiratory syncytial virus G glycoprotein (Genbank accession no. Z33429; Garcia et al., 1994, *J. Virol.; Collins et al.,* 1984, *Proc. Natl. Acad. Sci. USA* 81:7683), core protein, matrix protein or other protein of Dengue virus (Genbank accession no. M19197; Hahn et al., 1988, *Virology* 162:167-180), measles virus hemagglutinin (Genbank accession no. M81899; Rota et al., 1992, *Virology* 188:135-142), herpes simplex virus type 2 glycoprotein gB (Genbank accession no. M14923; Bzik et al., 1986, *Virology* 155:322-333), poliovirus I VP1 (Emini et al., 1983, *Nature* 304:699), envelope glycoproteins of HIV I (Putney et al., 1986, *Science* 234:1392-1395), hepatitis B surface antigen (Itoh et al., 1986, *Nature* 308:19; Neurath et al., 1986, *Vaccine* 4:34), diptheria toxin (Audibert et al., 1981, *Nature* 289:543), streptococcus 24M epitope (Beachey, 1985, *Adv. Exp. Med. Biol.* 185:193), gonococcal pilin (Rothbard and Schoolnik, 1985, *Adv. Exp. Med. Biol.* 185:247), pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, *Serpulina hydodysenteriae* protective antigen, bovine viral diarrhea glycoprotein 55, Newcastle disease virus hemagglutinin-neuraminidase, swine flu hemagglutinin, swine flu neuraminidase, foot and mouth disease virus, hog colera virus, swine influenza virus, African swine fever virus, *Mycoplasma hyopneumoniae*, infectious bovine rhinotracheitis virus (e.g., infectious bovine rhinotracheitis virus glycoprotein E or glycoprotein G), or infectious laryngotracheitis virus (e.g., infectious laryngotracheitis virus glycoprotein G or glycoprotein I), a glycoprotein of La Crosse virus (Gonzales-Scarano et al., 1982, *Virology* 120:42), neonatal calf diarrhea virus (Matsuno and Inouye, 1983, *Infection and Immunity* 39:155), Venezuelan equine encephalomyelitis virus (Mathews and Roehrig, 1982, *J. Immunol.* 129:2763), punta toro virus (Dalrymple et al., 1981, in Replication of Negative Strand Viruses, Bishop and Compans (eds.), Elsevier, N.Y., p. 167), murine leukemia virus (Steeves et al., 1974, *J. Virol.* 14:187), mouse mammary tumor virus (Massey and Schochetman, 1981, *Virology* 115:20), hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, *Ann. Rev. Biochem.* 56:651-693; Tiollais et al., 1985, *Nature* 317:489-495), antigen of equine influenza virus or equine herpesvirus (e.g., equine influenza virus type A/Alaska 91 neuraminidase, equine influenza virus type A/Miami 63 neuraminidase, equine influenza virus type A/Kentucky 81 neuraminidase equine herpesvirus type 1 glycoprotein B, and equine herpesvirus type 1 glycoprotein D, antigen of bovine respiratory syncytial virus or bovine parainfluenza virus (e.g., bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase), bovine viral diarrhea virus glycoprotein 48 or glycoprotein 53.

In other embodiments, the antigenic or immunogenic agent in the dermal vaccine formulations of the invention is a cancer antigen or a tumor antigen. Any cancer or tumor antigen known to one skilled in the art may be used in accordance with the dermal vaccine formulations of the invention including, but not limited to, KS 1/4 pan-carcinoma antigen (Perez and Walker, 1990, *J. Immunol.* 142:3662-3667; Bumal, 1988, *Hybridoma* 7(4):407-415), ovarian carcinoma antigen (CA125) (Yu et al., 1991, *Cancer Res.* 51(2):468-475), prostatic acid phosphate (Tailor et al., 1990, *Nucl. Acids Res.* 18(16):4928), prostate specific antigen (Henttu and Vihko, 1989, *Biochem. Biophys. Res. Comm.* 160(2):903-910; Israeli et al., 1993, *Cancer Res.* 53:227-230), melanoma-associated antigen p97 (Estin et al., 1989, *J. Natl. Cancer Instit.* 81(6):445-446), melanoma antigen gp75 (Vijayasardahl et al., 1990, *J. Exp. Med.* 171(4):1375-1380), high molecular weight melanoma antigen (HMW-MAA) (Natali et al., 1987, *Cancer* 59:55-63; Mittelman et al., 1990, *J. Clin. Invest.* 86:2136-2144), prostate specific membrane antigen, carcinoembryonic antigen (CEA) (Foon et al., 1994, *Proc. Am. Soc. Clin. Oncol.* 13:294), polymorphic epithelial mucin antigen, human milk fat globule antigen, colorectal tumor-associated antigens such as: CEA, TAG-72 (Yokata et al., 1992, *Cancer Res.* 52:3402-3408), CO17-1A (Ragnhammar et al., 1993, *Int. J. Cancer* 53:751-758); GICA 19-9 (Herlyn et al., 1982, *J. Clin. Immunol.* 2:135), CTA-1 and LEA, Burkitt's lymphoma antigen-38.13, CD19 (Ghetie et al., 1994, *Blood* 83:1329-1336), human B-lymphoma antigen-CD20 (Reffet al., 1994, Blood 83:435-445), CD33 (Sgouros et al., 1993, *J. Nucl. Med.* 34:422-430), melanoma specific antigens such as ganglioside GD2 (Saleh et al., 1993, *J. Immunol.,* 151, 3390-3398), ganglioside GD3 (Shitara et al., 1993, *Cancer Immunol. Immunother.* 36:373-380), ganglioside GM2 (Livingston et al., 1994, *J. Clin. Oncol.* 12:1036-1044), ganglioside GM3 (Hoon et al., 1993, *Cancer Res.* 53:5244-5250), tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen (Hellstrom et al., 1985, *Cancer. Res.* 45:2210-2188), differentiation antigen such as human lung carcinoma antigen L6, L20 (Hellstrom et al., 1986, *Cancer Res.* 46:3917-3923), antigens of fibrosarcoma, human leukemia T cell antigen-Gp37 (Bhattacharya-Chatterjee et al., 1988, *J. of Immunospecifically.* 141:1398-1403), neoglycoprotein, sphingolipids, breast cancer antigen such as EGFR (Epidermal growth factor receptor), HER2 antigen ($p185^{HER2}$), polymorphic epithelial mucin (PEM) (Hilkens et al., 1992, *Trends in Bio. Chem. Sci.* 17:359), malignant human lymphocyte antigen-APO-1 (Bernhard et al., 1989, *Science* 245:301-304), differentiation antigen (Feizi, 1985, *Nature* 314:53-57) such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group $Le^a$) found in Adenocarcinoma, NS-10 found in adenocarcinomas, CO-43 (blood group $Le^b$), G49 found in EGF receptor of A431 cells, MH2 (blood group ALe$^b$/Le$^y$) found in colonic adenocarcinoma, 19.9 found in colon cancer, gastric cancer mucins, T$_5$A$_7$ found in myeloid cells, R$_{24}$ found in melanoma, 4.2, G$_{D3}$, D1.1, OFA-1, G$_{M2}$, OFA-2, G$_{D2}$, and M1:22:25:8 found in embryonal carcinoma cells, and SSEA-3 and SSEA-4 found in 4 to 8-cell stage embryos. In one embodiment, the antigen is a Tcell receptor derived peptide from a Cutaneous Tcell Lymphoma (see, Edelson, 1998, The Cancer Journal 4:62). The inoculum may also contain cancer antigens originating from the kidney. Such antigens may be autologous, whereby the antigen is harvested from a patient, processed ex-vivo and returned to the same patient.

In some embodiments, the antigenic or immungenic agent in the dermal vaccine formulation of the invention comprise a virus, against which an immune response is desired. In certain embodiments, the dermal vaccine formulations of the invention comprise recombinant or chimeric viruses. In yet other embodiments, the dermal vaccine formulations of the invention comprise a virus which is attenuated. Production of recombinant, chimeric and attenuated viruses may be performed using standard methods known to one skilled in the art. The invention encompasses a live recombinant viral vaccine or an inactivated recombinant viral vaccine to be formulated in accordance with the invention. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In a specific embodiment, the recombinant virus is non-pathogenic to the subject to which it is administered. In this regard, the use of genetically engineered viruses for vaccine purposes may require the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed for use in the dermal vaccine formulations of the invention. Such viruses would go through only one or a few rounds of replication within the host. When used as a vaccine, the recombinant virus would go through limited replication cycle(s) and induce a sufficient level of immune response but it would not go further in the human host and cause disease.

Alternatively, inactivated (killed) virus may be formulated in accordance with the invention. Inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled.

In certain embodiments, completely foreign epitopes, including antigens derived from other viral or non-viral pathogens can be engineered into the virus for use in the dermal vaccine formulations of the invention. For example, antigens of non-related viruses such as HIV (gp160, gp120, gp41) parasite antigens (e.g., malaria), bacterial or fungal antigens or tumor antigens can be engineered into the attenuated strain.

Virtually any heterologous gene sequence may be constructed into the chimeric viruses of the invention for use in the dermal vaccine formulations. Preferably, heterologous gene sequences are moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to, influenza and parainfluenza hemagglutinin neuraminidase and fusion glycoproteins such as the HN and F genes of human PIV3. In yet another embodiment, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

Other heterologous sequences may be derived from tumor antigens, and the resulting chimeric viruses be used to generate an immune response against the tumor cells leading to tumor regression in vivo. In accordance with the present invention, recombinant viruses may be engineered to express tumor-associated antigens (TAAs), including but not limited to, human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, β-catenin, MUM-1, CDK4; Nonmelanoma antigens for breast, ovarian, cervical and pancreatic carcinoma, HER-2/neu, human papillomavirus-E6, -E7, MUC-1.

The antigenic or immunogenic agent for use in the dermal vaccine formulation of the invention may include one or more of the select agents and toxins as identified by the Center for Disease Control. In a specific embodiment, the select agent for use in the dermal vaccine formulations of the invention may comprise one or more antigens from Staphyloccocal enterotoxin B, Botulinum toxin, protective antigen for Anthrax, and Yersinia pestis. A non-limiting examples of select agents and toxins for use in the dermal vaccine formulations of the invention are listed in Table I:

TABLE I

SELECT AGENTS

HHS NON-OVERLAP SELECT AGENTS AND TOXINS

| | |
|---|---|
| ☐ | Crimean-Congo haemorrhagic fever virus |
| ☐ | Coccidioides posadasii |
| ☐ | Ebola viruses |
| ☐ | Cercopithecine herpesvirus 1 (Herpes B virus) |
| ☐ | Lassa fever virus |
| ☐ | Marburg virus |
| ☐ | Monkeypox virus |
| ☐ | Rickettsia prowazekii |
| ☐ | Rickettsia rickettsii |
| | South American haemorrhagic fever viruses |
| ☐ | Junin |
| ☐ | Machupo |
| ☐ | Sabia |
| ☐ | Flexal |
| ☐ | Guanarito |

TABLE I-continued

SELECT AGENTS

Tick-borne encephalitis complex (flavi) viruses

- ☐ Central European tick-borne encephalitis
- ☐ Far Eastern tick-borne encephalitis
- ☐ Russian spring and summer encephalitis
- ☐ Kyasanur forest disease
- ☐ Omsk hemorrhagic fever
- ☐ Variola major virus (Smallpox virus)
- ☐ Variola minor virus (Alastrim)
- ☐ *Yersinia pestis*
- ☐ Abrin
- ☐ Conotoxins
- ☐ Diacetoxyscirpenol
- ☐ Ricin
- ☐ Saxitoxin
- ☐ Shiga-like ribosome inactivating proteins
- ☐ Tetrodotoxin

HIGH CONSEQUENCE LIVESTOCK PATHOGENS AND TOXINS/SELECT AGENTS (OVERLAP AGENTS)

- ☐ *Bacillus anthracis*
- ☐ *Brucella abortus*
- ☐ *Brucella melitensis*
- ☐ *Brucella suis*
- ☐ *Burkholderia mallei* (formerly *Pseuodomonas mallei*)
- ☐ *Burkholderia pseudomallei* (formerly *Pseuodomonas pseudomallei*)
- ☐ Botulinum neurotoxin producing species of *Clostridium*
- ☐ *Coccidioides immitis*
- ☐ *Coxiella burnetii*
- ☐ Eastern equine encephalitis virus
- ☐ Hendra virus
- ☐ *Francisella tularensis*

HHS NON-OVERLAP SELECT AGENTS AND TOXINS

- ☐ Nipah Virus
- ☐ Rift Valley fever virus
- ☐ Venezuelan equine encephalitis virus
- ☐ Botulinum neurotoxin
- ☐ *Clostridium perfringens* epsilon toxin
- ☐ Shigatoxin
- ☐ Staphylococcal enterotoxin
- ☐ T-2 toxin USDA HIGH CONSEQUENCE LIVESTOCK PATHOGENS AND TOXINS (NON-OVERLAP AGENTS AND TOXINS

- ☐ Akabane virus
- ☐ African swine fever virus
- ☐ African horse sickness virus
- ☐ Avian influenza virus (highly pathogenic)
- ☐ Blue tongue virus (Exotic)
- ☐ Bovine spongiform encephalopathy agent
- ☐ Camel pox virus
- ☐ Classical swine fever virus
- ☐ *Cowdria ruminantium* (Heartwater)
- ☐ Foot and mouth disease virus
- ☐ Goat pox virus
- ☐ Lumpy skin disease virus
- ☐ Japanese encephalitis virus
- ☐ Malignant catarrhal fever virus (Exotic)
- ☐ Menangle virus
- ☐ *Mycoplasma capricolumi M.F38/M. mycoides capri*
- ☐ *Mycoplasm mycoides mycoides*
- ☐ Newcastle disease virus (VVND)
- ☐ Peste Des Petits Ruminants virus
- ☐ Rinderpest virus
- ☐ Sheep pox virus
- ☐ Swine vesicular disease virus
- ☐ Vesicular stomatitis virus (Exotic)

LISTED PLANT PATHOGENS

- ☐ *Liberobacter africanus*
- ☐ *Liberobacter asiaticus*
- ☐ *Peronosclerospora phillippinensis*
- ☐ *Phakopsora pachyrhizi*

TABLE I-continued

SELECT AGENTS

- ☐ Plum Pox Potyvirus
- ☐ *Ralstonia solanacearum* race 3, biovar 2
- ☐ *Schlerophthora rayssiae* var zeae
- ☐ *Synchytrium endobioticum*
- ☐ *Xanthomonas oryzae*
- ☐ *Xylella fastidiosa* (citrus variegated chlorosis strain)

5.2.1 Influenza Virus Antigens

Preferred vaccine delivery systems of the invention for dermal delivery including epidermal and intradermal, in accordance with the methods of the invention are influenza virus vaccines, which may comprise one or more influenza virus antigens. Preferably, the influenza virus antigens used in the dermal vaccine formulations of the invention (including epidermal and intradermal vaccine formulations) are surface antigens, including, but not limited to, haemagglutinin and neuraminidase antigens or a combination thereof. The influenza virus antigens may form part of a whole influenza vaccine formulations. Alternatively, the influenza virus antigens can be present as purified or substantially purified antigens. Techniques for isolating and purifying influenza virus antigens are known to one skilled in the art and are contemplated in the present invention. An example of a haemagglutinin/neuraminidase preparation suitable for use in the compositions of the present invention is the "Fluvirin" product manufactured and sold by Evans Medical Limited of Speke, Merseyside, United Kingdom, and see also S. Renfrey and A. Watts, 1994 *Vaccine*, 12(8): 747-752; which is incorporated herein by reference in its entirety.

The influenza vaccines useful in the dermal vaccine formulations of the present invention (including epidermal and intradermal vaccine formulations) may be any commercially available influenza vaccine, preferably a trivalent subunit vaccine, e.g., FLUZONE™ attenuated flu vaccine, Aventis Pasteur, Inc. Swiftwater, Pa.). The influenza vaccine formulations of the invention have a therapeutic efficacy at a dose which is lower than the conventional dose used for intramuscular delivery of influenza vaccines. The influenza vaccine used in the dermal vaccine of the invention (including epidermal and intradermal vaccine formulations) may be a non-live influenza antigenic preparation, preferably a split influenza or a subunit antigenic preparation, prepared using common methods known in the art. Most preferably, the influenza vaccine used in accordance with the invention is a trivalent vaccine.

The invention encompasses influenza vaccine formulations comprising a non-live influenza antigenic preparation, preferably a split influenza preparation or a subunit antigenic preparation prepared from a live virus. Most preferably the influenza antigenic preparation is a split influenza antigenic preparation.

The influenza vaccine formulation of the invention may contain influenza virus antigens from a single viral strain, or from a plurality of strains. For example, the influenza vaccine formulation may contain antigens taken from up to three or more viral strains. Purely by way of example the influenza vaccine formulation may contain antigens from one or more strains of influenza A together with antigens from one or more strains of influenza B. Examples of influenza strains are strains of influenza A/Texas/36/91, A/Nanchang/933/95 and B/Harbin/7/94).

In a most preferred embodiment, the influenza vaccine formulation of the invention comprises a commercially available influenza vaccine, FLUZONE™, which is an attenuated flu vaccine (Connaught Laboratories, Swiftwater, Pa.). FLUZONE is a trivalent subvirion vaccine comprising three 15 ug/dose(s) of three indivudial prototype Influenza strains—a B-strain, an H1N1 strain and an H3N2 strain, for example, A/Texas/36/91 (H1N1), A/Beijing/32/92 (H3N2) and B/Panama, 45/90.

Preferably, the influenza vaccine formulations of the invention have a lower quantity of haemagglutinin than conventional vaccines and are administered in a lower volume. In some embodiments, the quantity of haemagglutinin per strain of influenza is about 1-7.5 μg, more preferably approximately 3 μg or approximately 5 μg, which is about one fifth or one third, respectively, of the dose of haemagglutinin used in conventional vaccines for intramuscular administration.

The volume of a dose of an influenza vaccine formulation according to the invention is between 0.025 ml and 2.5 ml, more preferably approximately 0.1 ml or approximately 0.2 ml. In a specific embodiment, the invention encompasses a 50 μl dose volume of the influenza vaccine. A 0.1 ml dose is approximately one fifth of the volume of a conventional intramuscular flu vaccine dose. The volume of liquid that can be administered intradermally depends in part upon the site of the injection. For example, for an injection in the deltoid region, 0.1 ml is the maximum preferred volume whereas in the lumbar region a large volume e.g. about 0.2 ml can be given.

Standards are applied internationally to measure the efficacy of influenza vaccines. The European Union official criteria for an effective vaccine against influenza are set out in the table below. Theoretically, to meet the European Union requirements, and thus be approved for sale in the EU, an influenza vaccine has to meet one of the criteria in the table below, for all strains of influenza included in the vaccine. However in practice, at least two or more, probably all three of the criteria will need to be met for all strains, particularly for a new vaccine coming onto the market. Under some circumstances, two criteria may be sufficient. For example, it may be acceptable for two of the three criteria to be met by all strains while the third criterion is met by some but not all strains (e.g. two out of three strains). The requirements are different for adult populations (18-60 years) and elderly populations (>60 years).

TABLE II

EU STANDARDS FOR AN EFFECTIVE INFLUENZA VACCINE

|  | 18-60 years | >60 years |
| --- | --- | --- |
| Seroconversion rate | >40% | >30% |
| Conversion factor | >2.5 | >2.0 |
| Protection rate | >70% | >60% |

Seroconversion rate is defined as the percentage of vaccines who have at least a 4-fold increase in serum haemagglutinin inhibition (HI) titres after vaccination, for each vaccine strain. Conversion factor is defined as the fold increase in serum HI geometric mean titres (C3MTs) after vaccination, for each vaccine strain. Protection rate is defined as the percentage of vaccines with a serum HI titre equal to or greater than 1:40 after vaccination (for each vaccine strain) and is normally accepted as indicating protection.

The influenza vaccine formulations of the invention meet some or all of the EU criteria for influenza vaccines as set out hereinabove, such that the vaccine is approvable in Europe. Preferably, at least two out of the three EU criteria are met, for the or all strains of influenza represented in the vaccine. More preferably, at least two criteria are met for all strains and the third criterion is met by all strains or at least by all but one of the strains. More preferably, all strains present meet all three of the criteria. Preferably, the influenza vaccine formulations of the invention additionally meet some or all criteria of the Federal Drug Administration and/or USPHS requirements for the current influenza vaccines.

5.3 Additives

In certain embodiments, the dermal vaccine formulations of the invention (including intradermal and epidermal vaccine formulations) further comprise one or more additives, including, but not limited to, adjuvants, excipients, stabilizers, penetration enhancers, mucoadhesive molecules, and bioadhesive molecules. The additives in the dermal vaccine formulations may act in a synersgisitic or additive manner to enhance the efficacy of the dermal vaccine formulations of the invention.

In some embodiments, the dermal vaccine formulation of the invention may further comprise one or more adjuvants. Any of the conventional adjuvants used in vaccine formulations to enhance the efficacy and protective immune response of the vaccine formulation is encompassed within the invention. For a review of adjuvants, see, e.g., Vogel and Powell, 1995, A Compendium of Vaccine Adjuvants and Excipients; M. F. Powell, M. J. Newman (eds.), Plenum Press, New York, page 141-228; all of which is incorporated herein by reference in its entirety. A non-limiting example of adjuvants that may be used in the dermal vaccine formulations of the invention is listed in Table III.

Typically, adjuvants are characterized to encompass at least three categories of molecules as classified by their function and all such molecules are encompassed within the invention. In one embodiment, the adjuvant used in the dermal vaccine formulation of the invention may function as a depot. A non-limiting example of depots include Alum and Incomplete Freunds, which keep the antigenic or immunogenic agent concentrated and control its release. In another embodiment, the adjuvant used in the dermal vaccine formulation of the invention may act as a stimulant, i.e., a molecule that excites the antigen presenting cells and ultimately results in a broad effective immune response. A non-limiting example of stimulants are surface antigens from organisms such as C. Parvum and plant extracts. In yet another embodiment, the adjuvant used in the dermal vaccine formulation of the invention is an immunogen or antigen targeting molecule that for example, helps to concentrate the immunogenic or antigenic agent on the surface of immune antigen presenting cells (APCs) and thereby enhances their uptake, including, but not limited, to molecules such as antibodies and alpha 2-macroglobulin.

TABLE III

| ADJUVANTS | | | | |
|---|---|---|---|---|
| 1. Mineral | 2. Surface-active agents and Microparticles | 3. Bacterial Products | 4. Cytokines and Hormones | 5. Unique antigen Constructs |
| Aluminum ("Alum") Aluminum hydroxide * Aluminum phosphate * Calcium phosphate * | Nonionic block polymer surfactants * Virosomes * Ty-virus-like-particles * Saponin (QS-21) * Meningococcal outer membrane proteins (Proteosomes) * Immune stimulating complexes (ISCOMs) * Cochleates Dimethyl dioctadecyl ammonium bromide (DDA) Avridine )CP20, 961) Vitamin A Vitamin E | Cell wall skeleton of *Mycobacterium phlei* (Detox ®) * Muramyl dipeptides and tripeptides Threonyl MDP (SAF-1) * Butyl-ester MDP (Murabutide ®) * Dipalmitoyl phosphatidylethanolamine MTP * Monophosphoryl lipid A * *Klebsiella pneumonia* glycoprotein * *Bordetella pertussis* * *Bacillus* Calmette-Guérin * *V. cholerae* and *E. coli* heat labile enterotoxin * CpG oligodeoxynucleotides * Trehalose dimycolate | Interleukin-2 * Interleukin-12 * Interferon-alpha * Interferon-gamma * Granulocyte-macrophage colony stimulating factor * Dehydroepiandrosterone * Flt3 ligand * 1,25-dihydroxy vitamin $D_3$ Interleukin-1 Interleukin-6 Human growth hormone 2-microglobulin Lymphotactin | Multiple peptide antigens attached to lysine pr polyoxime core (MAP) * CT1, epitope linked to universal helper T cell epitope and palmitoylated at the N terminus (Theradigm-HBV) * |

| 6. Polyanions | 7. Polyacrylics | 8. Miscellaneous | 9. Carriers | 20. Living Vectors | 11. Vehicles |
|---|---|---|---|---|---|
| Dextran Double-stranded polynucleotides | Polymethylmethacrylate Acrylic acid cross-linked with allyl sucrose (Carbopol 934P) | N-acetyl-glucosamine-3yl-acetyl-L-alanyl-D-isoglutamine (CGP-11637) * Gamma inulin + aluminum hydroxide (Algammulin) * Transgenic plants * Human dendritic cells * Lysophosphatidyl glycerol Stearyl tyrosine Tripalmitoyl pentapeptide | Tetanus toxoid * Diphtheria-toxoid * Meningococcal B outer membrane protein (Proteosomes) * *Pseudomonas* exotoxin A * Cholera toxin B subunit * Mutant heat labile enterotoxin of enterotoxigenic *E. coli* * Hepatitis B virus core * CpG dinucleotides * Cholera toxin A fusion proteins Heat shock proteins Fatty acids | Vaccinia virus * Canarypox virus * Adenovirus Yellow fever vaccine virus * Attenuated *Salmonella typhi* * Attenuated *Shigella* * *Bacillus* Calmette-Guérin * *Streptococcus gordonni* * Herpes simplex virus Polio vaccine virus rhinovirus Venezuelan equine encephalitis virus Sindbis virus *Yersinia enterocolitica Listeria monocytogenes Bordetella pertussis Saccharomyces cerevisiae* | Water-in-oil emulsions Mineral oil (Freud's incomplete) * Vegetable oil (peanut oil) * Squalene and squalane * Oil-in-water emulsions Squalene + Tween 80 + Span 85 (MF59) * Liposomes * Biodegradable polymer microspheres Lactide and glycolide * Polyphosphazenes * Beta-glucan Proteinoids |

* Identifies adjuvants administered to humans. Of these, only aluminum salts, virosomes, and MF-59 are adjuvants approved as licensed vaccine formulations in the United States.

Adjuvants useful in the methods of the invention may stimulate humoral and/or cell mediated immunity, including CD4+ and CD8+ mediated immune response.

Non-limiting example of adjuvants for use in the dermal vaccine formulations of the invention are, Chitosan, derivatives and analogs thereof (a cationic polysaccharide derived by deacetylation of chitin;); bacterially derived products such as monophosphoryl lipid A (MPL; a derivative of lipopolysaccharaide primarily from *Salmonella minnesotta*); CpG motifs (derived from bacterial plasmid DNA which are typically used in the form of synthetic oligonucleotides; contain immunostimulatory sequences consisting of unmethylated CpG motifs that are uncommon in mammalian DNA); detoxified mutants of cholera toxin (CT; from *Virbrio cholorea*) and heat labile toxin (LT; from *E. coli*); outer membrane proteins of *Neisseria meningitidis* serogroup b; dimethyl dioctadecyl ammonium bromide (DDA); cytokines (e.g., IL-12, IL-6, GM-SF, IL-4, IL-7); triterpenoid glycoside or saponins, derivatives and analogs thereof (derived from Quillaja saponaria; chilean soap bark tree; saponins intercalate with cell membranes through interaction with cholesterol, forming pores that can enhance antigen transport across membranes); 3-Q-desacyl-4'-monophosphoryl lipid A (3D-MLA), formylated-met-leu-phe (fMLP); and IL-1 beta 163-171 peptide ("Sclavo Peptide").

In certain embodiments, the invention encompasses the use of chitosan as an additive in the dermal vaccine formulations of the invention. The invention encompasses all chitosan derivatives, analogs, and variants thereof (for a review see van der Lubben et al., 2001, *European Journal of Pharmaceutical Sciences*, 14: 201-7; Dodane et al., 1998, *Pharm. Sci. Tech. Today*, 1: 246-53; both of which are incorporated herein by reference in their entirety). Chitosan is a linear polysaccharide formed from repeating beta (1-4 inked) N-acetyl-D-glucosamine and D-glucosamine units, and is derived from the partial deacetylation of chitin obtained from the shells of crustaceans. Chitosan is usually made commercially by a heterogeneous alkaline hydrolysis of chitin to give a product which possesses a random distribution of remaining acetyl moieties. Preparation of chitosan for use in the methods of the invention may be done using any method known to one skilled in the art.

The properties of chitosans depend, in part, upon the degree of deacetylation, and the molecular weight. The invention encompasses the use of chitosans of varying degrees of deacetylation in order to achieve the desired biological response, e.g., an enhanced immune response, in the intradermal compartment. Varying the degree of acetylation of chitosan is within the purview of one skilled in the art. Most commercially available chitosans contain a population of chitosan molecules of varying molecular weights and varying concentrations of the component N-acetyl-D-glucosamine and D-glucosamine groups, all of which are encompassed within the invention. The immunological properties of chitosans are known to be linked to the ratio between the N-acetyl-D-glucosamine and D-glucosamine groups. The ratio of N-acetyl-D-glucosamine and D-glucosamine groups can be varied using methods known to one skilled in the art in order to achieve the desired biological response, e.g., an enhanced immune response, in the intradermal compartment. The use of chitosans in an immunological context has been described, see, e.g., Iida et al., 1994 *Vaccine* 5: 270-273; Nishimura et al., 1984 *Vaccine* 2(99): 94-100; both of which are incorporated herein by reference in their entirety.

The chitosan used in the dermal vaccine formulations of the invention may have one or more properties of an adjuvant, a penetration enhancer, a mucoadhesive, a bioadhesive, or a combination thereof.

In other embodiments, the invention encompasses the use of saponins, derivatives, and analogs thereof for use in the dermal vaccine formulations of the invention. Quillaja saponins are a mixture of triterpene glycosides extracted from the bark of the tree Quillaja saponaria. They have long been recognized as immune stimulators that can be used as vaccine adjuvants, see, e.g., Campbell and Peerbaye, 1992, *Res. Immunol.* 143(5):526-530, and a number of commercially available complex saponin extracts have been utilized as adjuvants, all of which are contemplated within the present invention. Any of the commercially available saponin based adjuvants are encompassed within the present invention. Methods for preparation of saponin based adjuvants are within the purview of the ordinary skilled artisan. A non-limiting example of Quillaja saponins are QS-7, QS-17, QS-18, and QS-21 (alternatively identified as QA-7, QA-17, QA-18, and QA-21) all of which may be used in the dermal vaccine formulations of the invention. Quillaja saponins, particularly QS-7, QS-17, QS-18, and QS-21, have been found to be excellent stimulators of antibody response and are thus particularly useful in the dermal vaccine formulations of the invention. The immune adjuvant effect of saponins is dependent upon dose, which can be determined using methods known to one skilled in the art.

Other examples of adjuvants for use in the dermal vaccine formulations of the invention are 25-dihydroxyvitamin D3 (calcitrol), calcitinin-gene regulated peptides, Dehydroepiandrosterone (DHEA), N-Acetylglucosaminyl-(PI-4)-N-acetylmuramyl-L-alanyl-D-glutamine (GMDP)/dimethyl dioctadecyla or disteary ammonium bromide (DDA)/Zinc L-proline, muramyl dipeptide (MDP), N-Acetylglucopaminyl-(PI4)-N-acetylmuramyl-L-alanyl-D-glutamine (GMDP), N-acetyl muramyl-L-tllreonyl-D-isoglutamine (Threonyl-MDP), N-acetyl-L-alanyl-Disoglutaminyl-L-alanine-2-(1,2-dipalmitoyl-sn-glycero-3-(hydroxy-phosphoryloxy)ethylamide monosodium salt(MTP-PE), Nac-Mur-L-Ala-D-Gln-OCH3, Nac-Mur-L-Thr-D-isoGln-snglycerol dipalmitoyl, Nac-Mur•D-Ala-D-isoGin-sn-glycerol dipalmitoyl, 1-(2-methypropyl)IH-imidazo[4,5-c]quinolin-4-artnine, 4-Amino-otec-dimethyl-2-ethoxymethyl-IH-imidazo [4,5c]quinoline-1-ethanol, N-acetyl$lucosaminyl-N-acetylmuramyl-L-Ala-D-isoGlu-L-Ala-glycerol dipalmitate (DTP-GDP), N-acetylglucosaminyl-N-acetylinuramyl-L-Ala-D-isoGlu-L-Aladipalmitoxy propylamide (DTP-PPP), gamma interferon, 7-allyl-8-oxoguanosine, Poly-adenylic acid-poly-uridylic acid complex, MIP-1 a, MIP-3a, RANTES; dibutyl phthahate and dibutyl phthalate analogues.

The excipients that can be used in the dermal vaccine formulations of the invention include for example, saccharides and polyols. Additional examples of pharmaceutically acceptable carriers, diluents, and other excipients are provided in *Remington's Pharmaceutical Sciences* (Mack Pub. Co., N.J., current edition; all of which is incorporated herein by reference in its entirety).

In some embodiments, the dermal vaccine formulations of the invention may comprise a penetration enhancer. As used herein, a "penetration enhancer" is any molecule that, when added to an dermal vaccine formulation of the invention, enables or enhances permeation of the immunogenic or antigenic agent across biological membranes, thereby increasing absorption of the immunogenic or antigenic agent. Non-limiting examples of penetration enhancers include, various molecular weight chitosans, such as chitosan and N,O-carboxymethyl chitosan; poly-L-arginines; fatty acids, such as lauric acid; bile salts such as deoxycholate, glycolate, cholate, taurocholate, taurodeoxycholate, and glycodeoxycholate; salts of fusidic acid such as taurodihydrofusidate; polyoxyethylenesorbitan such as TWEEN™ 20 and TWEEN™ 80; sodium lauryl sulfate; polyoxyethylene-9-lauryl ether (Laureth™ 9); EDTA; citric acid; salicylates; caprylic/capric glycerides; sodium caprylate; sodium caprate; sodium laurate; sodium glycyrrhetinate; dipotassium glycyrrhizinate; glycyrrhetinic acid hydrogen succinate, disodium salt (Carbenoxolone™); acylcarnitines such as palmitoylcarnitine; cyclodextrin; and phospholipids, such as lysophosphatidylcholine. Preferably, the penetration enhancer is selected from the group consisting of chitosan, fatty acids, polyethylene sorbitol and caprylic/capric glycerides.

The dermal vaccine formulations of the inventions may also comprise other additives besides an adjuvant and/or a penetration enhancer. For example, the intradermal formulation of the invention may comprise a protein stabilizer, e.g., trehalose, sucrose, glycine, mannitol, albumin, glycerol. In some embodiments, antigen-stabilizing solutes, typically protein-stabilizing solutes, are incorporated into the dermal vaccine formulation of the invention. The use of protein-stabilizing solutes, such as sucrose, not only aids in protecting and/or stabilizing the antigenic or immunogenic agent in the dermal vaccine formulation of the invention (especially when the antigenic or immunogenic agent is a protein), but also permits manipulation of the properties of the formulation, e.g., liquid-gel transition. For example, addition of certain protein-stabilizing solvents may allow the formulation to exhibit a desired thermally induced liquid-gel at lower concentration of the geling agent and/or at an altered liquid-gel transition temperature than when the protein-stabilizing is not used, especially when using the preferred polyalkoxyalkylene block copolymers. Thus, the working range of the concentration of the geling agent can be widened and the transition temperature modified. However, by introducing protein-stabilizing solutes to an dermal vaccine formulation of the present invention, the transition temperature may be manipulated, while also lowering the concentration of the geling agent that is necessary to form a gel. In this regard, preferred protein-stability solvents are sugars, such as, for example, sucrose.

5.4 Preparation of the Intradermal Vaccine Formulations

The intradermal vaccine formulation of the invention may be prepared by any method that results in a stable, sterile, injectable formulation. Preferably, the method for preparing an intradermal vaccine formulation of the invention comprises: providing a solution of the cocktail, e.g., a geling agent and a mucoadhesive; providing a solution of the antigenic or immunogenic agent; combining the solution of the cocktail and the solution of the antigenic or immunogenic agent to form the inoculum, e.g., the solution to be injected to the intradermal compartment; and mixing the resulting combination about 1 hour prior to administration of the formulation to a subject. In a specific embodiment, where the cocktail comprises a geling, preferably, the mixing is done at a temperature below the liquid-gel transition temperature of the geling agent.

In a specific embodiment, when the cocktail comprises a polymer, the polymer may be dissolved in an aqueous solution, e.g., water, at a temperature below the liquid-gel transition temperature of the polymer and at a concentration such that above the liquid-gel transition temperature a gelatinous matrix may be formed. An exemplary method for determining the concentration of the polymer for the intradermal vaccine formulations of the invention may comprise the following: an aqueous stock solution of the polymer is prepared, e.g., in tissue culture grade water; the solution is then incubated, preferably, by mechanical agitation, e.g., magnetic stirring, at a temperature below the liquid-gel transition temperature, e.g., on ice at 4° C.; the pH of the solution is adjusted to a physiological pH, ranging from 7.0 to 7.4, preferably to 7.2; the solution is sterilized, preferably by filtration, e.g., using a 0.2 micron Gelman Acrodisc PF Syringe Filter # 4187; the solution is incubated at 37° C., e.g., by placing it in a 37° C. water bath; and the solution is visually monitored, Specifically, the viscosity of the solution is visually monitored. Preferably, the solution gels within 5 minutes or less. In some embodiments, the solution gels within 20 minutes or less, 15 minutes or less, 10 minutes or less. If the solution does not gel within the time frame specified above, the concentration of the polymer is adjusted so that a higher percentage of the polymer is used. The concentration of the polymer is adjusted so that the solution preferably gels, as determined by visual inspection of the solution, within 20 minutes or less, within 10 minutes or less, preferably within 5 minutes or less at 37° C.

The optimal concentration at which the polymer solution is formed depends on the particular polymer as discussed above. The concentration of the polymer used in the intradermal vaccine formulations of the invention may be at least 10% (w/v), at least 10% (w/v), at least 15% (w/v), at least 20% (w/v), at least 25% (w/v), or at least 30% (w/v). The concentration of the polymer used in the intradermal vaccine formulations of the invention is preferably the concentration at which an aqueous solution of the polymer gels, i.e., forms a semi-solid to solid two or three dimensional matrix, within 20 minutes or less, preferably within 10 minutes or less, and most preferably within 5 minutes or less at a physiological temperature, e.g., at 37° C. Preferably the concentration at which an aqueous solution of the polymer gels is also the concentration at which the therapeutic efficacy of the intradermal vaccine formulation of the invention is enhanced as determined using standard methods known to one skilled in the art, e.g., as determined by the antibody response to the antigenic or immunogenic agent, relative to a control formulation, e.g., a formulation comprising the antigenic or immunogenic agent alone.

The antigenic or immunogenic agent may be dissolved in the aqueous solution, comprising the cocktail such that a stable, sterile, injectable formulation is formed. Alternatively, the antigenic or immunogenic agent may be particulate and dissolved in the cocktail solution such that a stable, sterile, injectable formulation is formed. Where the cocktail comprises a geling agent, for enhanced performance of the intradermal vaccine formulation of the invention, the antigenic or immunogenic agent should be uniformly dispersed throughout the gelatinous matrix, which can be achieved by dissolving the antigenic or immunogenic agent in a solution comprising the polymer at a temperature below the liquid-gel transition temperature of the polymer so that once the temperature is raised the antigenic or immunogenic agent is uniformly dispersed and embedded in the gelatinous matrix.

In other embodiments, when the cocktail comprises a muco or bioadhesive, the concentration of the muco or bioadhesive molecule in the intradermal vaccine formulations of the invention may be 0.1% (w/v) to 1% (w/v), 0.1% (w/v) to 5% (w/v), or 0.1% (w/v) to 10% (w/v). The concentration of the muco or bioadhesive molecule used in the intradermal vaccine formulations of the invention is preferably the concentration at which the therapeutic efficacy of the intradermal vaccine formulation of the invention is enhanced, e.g., as determined by the antibody response to the antigenic or immunogenic agent, relative to a control formulation, e.g., a formulation comprising the antigenic or immunogenic agent alone.

The amount of the antigenic or immunogenic agent used in the intradermal vaccine formulations of the invention may vary depending on the chemical nature and the potency of the antigenic or immunogenic agent. Typically, the starting concentration of the antigenic or immunogenic agent in the intradermal vaccine formulation of the invention is the amount that is conventionally used for eliciting the desired immune response, using the conventional routes of administration, e.g., intramuscular injection. The concentration of the antigenic or immunogenic agent is then adjusted, e.g., by dilution using a diluent, in the intradermal vaccine formulations of the invention so that an effective protective immune response is achieved as assessed using standard methods known in the art and described herein. The concentration of the antigenic or immunogenic agent used in the intradermal vaccine formulations of the invention is 60%, preferably 50%, more preferably 40% of the concentration conventionally used in obtaining an effective immune response.

5.5 Preparation of Epidermal Vaccine Formulations

The epidermal vaccine formulations of the invention may be prepared by any method that results in a stable, sterile formulation such as those known in the art and disclosed in U.S. Provisional patent application Nos. 60/330,713, 60/333,162 and U.S. application Ser. No. 09/576,643, U.S. application Ser. No. 10/282,231, filed Oct. 29, 2001, Nov. 27, 2001, and May 22, 2000 and Oct. 29, 2002, respectively, all of which are each hereby incorporated by reference in their entirety. They can be delivered, inter alia, in the form of dry powders, gels, solutions, suspensions, and creams.

The vaccine formulation may be delivered into the epidermal compartment of skin in any pharmaceutically acceptable form. In one embodiment the vaccine formulation is applied to the skin and an abrading device is then moved or rubbed reciprocally over the skin and the substance. It is preferred that the minimum amount of abrasion to produce the desired result be used. Determination of the appropriate amount of abrasion for a selected vaccine formulation is within the ordinary skill in the art. In another embodiment the vaccine formulation may be applied in dry form to the abrading surface of the delivery device prior to application. In this embodiment, a reconstituting liquid is applied to the skin at the delivery site and the formulation-coated abrading device is applied to the skin at the site of the reconstituting liquid. It is then moved or rubbed reciprocally over the skin so that the vaccine formulation becomes dissolved in the reconstituting liquid on the surface of the skin and is delivered simultaneously with abrasion. Alternatively, a reconstituting liquid may be contained in the abrading device and released to dissolve the vaccine formulation as the device is applied to the skin for abrasion. It has been found that certain vaccine formulations, may also be coated on the abrading device in the form of a gel.

5.6 Administration of the Intradermal Vaccine Formulations

Figure 8:
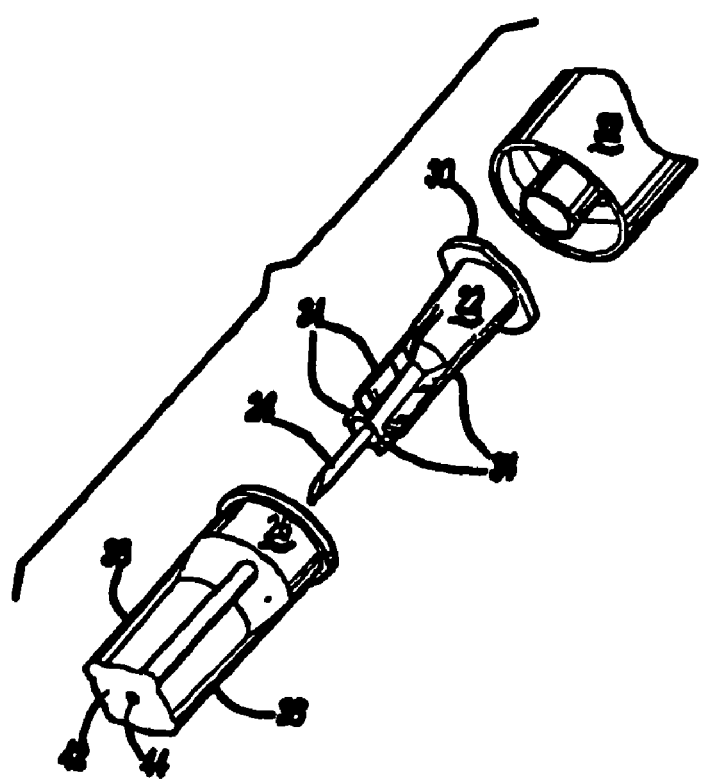
Figure 9:
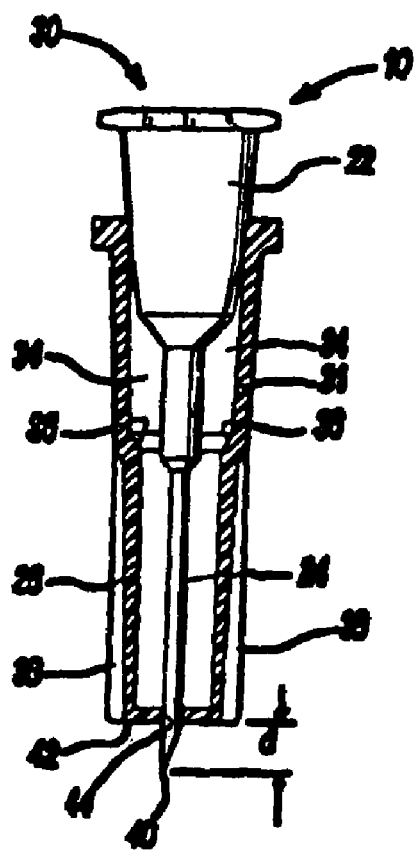
Figure 10:
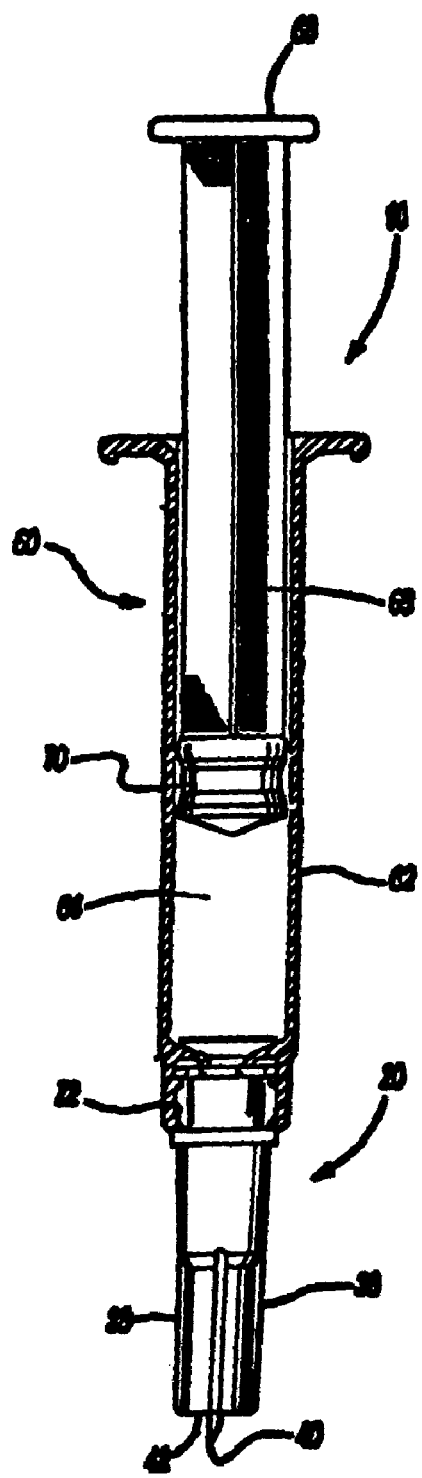
Figure 11:
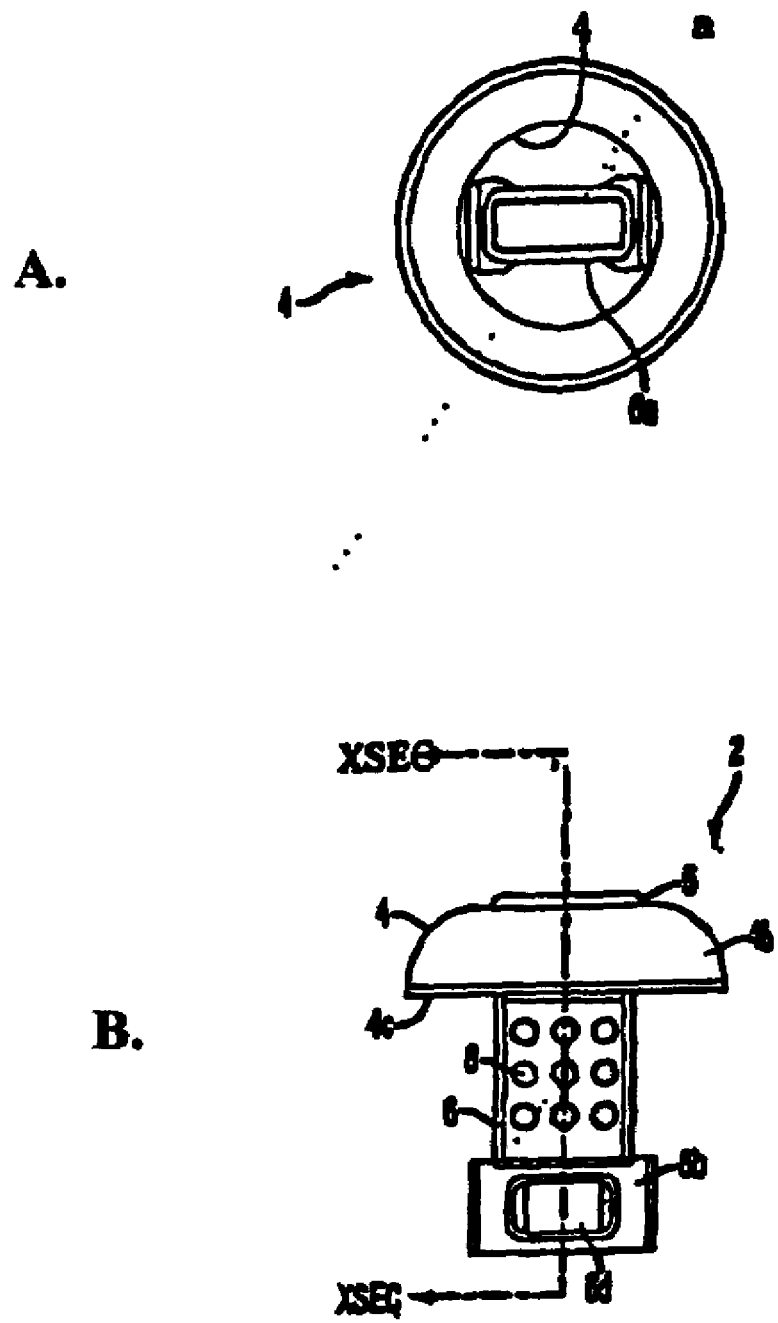

The present invention encompasses methods for intradermal delivery of the vaccine formulations described and exemplified herein to the intradermal compartment of a subject's skin, preferably by directly and selectively targeting the intradermal space. Once the intradermal vaccine formulation is prepared in accordance to the methods described supra, the inoculum is typically transferred to an injection device for intradermal delivery, e.g., a syringe. Preferably, the inoculum is administered to the intradermal compartment of a subject's skin within 1 hour of preparation. The intradermal vaccine formulations of the invention are administered using any of the intradermal devices and methods disclosed in U.S. patent application Ser. No. 09/417,671, filed on Oct. 14, 1999; Ser. No. 09/606,909, filed on Jun. 29, 2000; Ser. No. 09/893,746, filed on Jun. 29, 2001; Ser. No. 10/028,989, filed on Dec. 28, 2001; Ser. No. 10/028,988, filed on Dec. 28, 2001; or International Publication No. EP 10922 444, published Apr. 18, 2001; WO 01/02178, published Jan. 10, 2002; and WO 02/02179, published Jan. 10, 2002; all of which are incorporated herein by reference in their entirety. Exemplary devices are shown in FIGS. 8-10.

The present invention improves the clinical utility and therapeutic efficacy of vaccine formulations described herein by specifically and selectively, preferably directly, targeting the intradermal space. The intradermal vaccine formulations may be delivered to the intradermal space as a bolus or by infusion.

The inventors have discovered unexpectedly that the delivery of the vaccine formulations described and exemplified herein to the dermis provides for efficacious and/or improved responsiveness to the vaccine formulation. The vaccine formulations of the invention as administered to the intradermal compartment have an improved adsorption and/or cellular uptake within the intradermal space. The immunological response to a vaccine formulation delivered according to the methods of the invention has been found to be equivalent to or improved over conventional routes of delivery, e.g., intramuscular.

The present invention provides a method to improve the availability of a vaccine formulation of the invention to the immune cells residing in the skin, e.g., antigen presenting cells, in order to effectuate an antigen-specific immune response to the vaccine formulation by accurately targeting the intradermal space. Preferably, the methods of the invention, allow for smaller doses of the intradermal vaccine formulation to be administered via the intradermal route.

The intrademal methods of administration comprise microneedle-based injection and infusion systems or any other means to accurately target the intradermal space. The intradermal methods of administration encompass not only microdevice-based injection means, but other delivery methods such as needless or needle-free ballistic injection of fluids or powders into the intradermal space, Mantoux-type intradermal injection, enhanced iontophoresis through microdevices, and direct deposition of fluid, solids, or other dosing forms into the skin.

In a specific embodiment, the intradermal vaccine formulations of the invention are administered to an intradermal compartment of a subject's skin using an intradermal Mantoux type injection, see, e.g., Flynn et al., 1994, *Chest* 106: 1463-5, which is incorporated herein by reference in its entirety.

In a specific embodiment, the intradermal vaccine formulation of the invention is delivered to the intradermal compartment of a subject's skin using the following exemplary method. The intradermal vaccine formulation as prepared in accordance to methods disclosed herein, is drawn up into a syringe, e.g., a 1 mL latex free syringe with a 20 gauge needle; after the syringe is loaded it is replaced with a 30 gauge needle for intradermal administration. The skin of the subject, e.g., mouse, is approached at the most shallow possible angle with the bevel of the needle pointing upwards, and the skin pulled tight. The injection volume is then pushed in slowly over 5-10 seconds forming the typical "bleb" and the needle is subsequently slowly removed. Preferably, only one injection site is used. More preferably, the injection volume is no more than 100 μL, due in part, to the fact that a larger injection volume may increase the spill over into the surrounding tissue space, e.g., the subcutaneous space.

The invention encompasses the use of conventional injection needles, catheters or microneedles of all known types, employed singularly or in multiple needle arrays. The terms "needle" and "needles" as used herein are intended to encompass all such needle-like structures. The term "microneedles" as used herein are intended to encompass structures smaller than about 30 gauge, typically about 31-50 gauge when such structures are cylindrical in nature. Non-cylindrical structures encompass by the term microneedles would therefore be of comparable diameter and include pyramidal, rectangular, octagonal, wedged, and other geometrical shapes.

The intradermal delivery of the vaccine formulations of the invention may use ballistic fluid injection devices, powder jet delivery devices, piezoelectric, electromotive, electromagnetic assisted delivery devices, gas-assisted delivery devices, which directly penetrate the skin to directly deliver the vaccine formulations of the invention to the targeted location within the dermal space.

The actual method by which the intradermal vaccine formulations of the invention are targeted to the intradermal space is not critical as long as it penetrates the skin of a subject to the desired targeted depth within the intradermal space without passing through it. The actual optimal penetration depth will vary depending on the thickness of the subject's skin. In most cases, skin is penetrated to a depth of about 0.5-2 mm. Regardless of the specific intradermal device and method of delivery, the intradermal vaccine formulation preferably targets the vaccine formulations of the invention to a depth of at least 0.3 mm, more preferably at least 0.5 mm up to a depth of no more than 2.5 mm, more preferably no more than 2.0 mm, and most preferably no more than 1.7 mm. The methods of the invention comprise use of delivery devices as disclosed infra which place the needle outlet at an appropriate depth in the intradermal space and control the volume and rate of fluid delivery provide accurate delivery of the formulation to the desired location without leakage.

The invention encompasses use of devices comprising microneedles which have a length sufficient to penetrate the intradermal space (the "penetration depth") and an outlet at a depth within the intradermal space (the "outlet depth") which allows the skin to seal around the needle against the back-pressure which tends to force the delivered formulation toward the skin surface. In general, the needle is no more than about 2 mm long, preferably about 300 μm to 2 mm long, most preferably about 500 μm to 1 mm long. The needle outlet is typically at a depth of about 250 μm to 2 mm when the needle is inserted in the skin, preferably at a depth of about 750 μm to 1.5 mm, and most preferably at a depth of about 1 mm. The exposed height of the needle outlet and the depth of the outlet within the intradermal space influence the extent of sealing by the skin around the needle. That is, at a greater depth a needle outlet with a greater exposed height will still seal efficiently whereas an outlet with the same exposed height will not seal efficiently when placed at a shallower depth within the intradermal space. Typically, the exposed height of the needle outlet will be from 0 to about 1 mm, preferably from 0 to about 300 μm. A needle outlet with an exposed height of 0 has no bevel and is at the tip of the needle. in this case, the depth of the outlet is the same as the depth of penetration of the needle. A needle outlet which is either formed by a bevel or by an opening though the side of the needle has a measurable exposed height.

In some embodiments, the vaccine formulations are delivered at a targeted depth just under the stratum corneum and encompassing the epidermis and upper dermis, e.g., about 0.025 mm to about 2.5 mm. In order to target specific cells in the skin, the preferred target depth depends on the particular cell being targeted and the thickness of the skin of the particular subject. For example, to target the Langerhan's cells in the dermal space of human skin, delivery would need to encompass, at least, in part, the epidermal tissue depth typically ranging from about 0.025 mm to about 0.2 mm in humans.

In some embodiments, when the vaccine formulations require systemic circulation, the preferred target depth would be between, at least about 0.4 mm and most preferably, at least about 0.5 mm, up to a depth of no more than about 2.5 mm, more preferably, no more than about 2.0 mm and most preferably, no more than about 1.7 mm. Targeting the vaccine formulations predominately at greater depths and/or into a lower portion of the reticular dermis is usually considered to be less desirable.

The invention provides a method for an improved method of delivering the vaccines formulations into the intradermal compartment of a subject's skin compring the steps of providing a drug delivery device, e.g., such as those exemplified in FIGS. 8-10, including a needle cannula having a forward needle tip and the needle cannula being in fluid communication with a formulation contained in the drug delivery device and including a limiter portion surrounding the needle cannula and the limiter portion including a skin engaging surface, with the needle tip of the needle cannula extending from the limiter portion beyond the skin engaging surface a distance equal to approximately 0.5 mm to approximately 3.0 mm and the needle cannula having a fixed angle of orientation relative to a plane of the skin engaging surface of the limiter portion, inserting the needle tip into the skin of an animal and engaging the surface of the skin with the skin engaging surface of the limiter portion, such that the skin engaging surface of the limiter portion limits penetration of the needle cannula tip into the dermis layer of the skin of the animal, and expelling the formulation from the drug delivery device through the needle cannula tip into the skin of the subject.

Also, in other preferred embodiment, the invention encompass selecting an injection site on the skin of the subject, cleaning the injection site on the skin of the subject prior to expelling the vaccine formulations of the invention from the drug delivery device into the skin of the subject. In addition, the method comprises filling the drug delivery device with the vaccine formulations of the invention. Further, the method comprises pressing the skin engaging surface of the limiter portion against the skin of the subject and applying pressure, thereby stretching the skin of the subject, and withdrawing the needle cannula from the skin after injecting the vaccine formulations. Still further, the step of inserting the forward tip into the skin is further defined by inserting the forward tip into the skin to a depth of from approximately 1.0 mm to approximately 2.0 mm, and most preferably into the skin to a depth of 1.5 mm±0.2 to 0.3 mm. FIGS. 8-10 exemplify specific embodiments of the intradermal methods of the invention.

In the preferred embodiment of the method, the step of inserting the forward tip into the skin of the subject is further defined by inserting the forward tip into the skin at an angle being generally perpendicular to the skin within about fifteen degrees, with the angle most preferably being generally ninety degrees to the skin, within about five degrees, and the fixed angle of orientation relative to the skin engaging surface is further defined as being generally perpendicular. In the preferred embodiment, the limiter surrounds the needle cannula, having a generally planar flat skin engaging surface. Also, the drug delivery device comprises a syringe having a barrel and a plunger received within the barrel and the plunger being depressable to expel the substance from the delivery device through the forward tip of the needle cannula, e.g., see FIGS. 7-10.

In a preferred embodiment, expelling the vaccine formulation, from the delivery device is further defined by grasping the hypodermic needle with a first hand and depressing the plunger with an index finger of a second hand and expelling vaccine formulation from the delivery device by grasping the hypodermic needle with a first hand and depressing the plunger on the hypodermic needle with a thumb of a second hand, with the step of inserting the forward tip into the skin of the animal further defined by pressing the skin of the animal with the limiter. In addition, the method may further comprise the step of attaching a needle assembly to a tip of the barrel of the syringe with the needle assembly including the needle cannula and the limiter, and may comprise the step of exposing the tip of the barrel before attaching the needle assembly thereto by removing a cap from the tip of the barrel. Alternatively, the step of inserting the forward tip of the needle into the skin of the subject may be further defined by simultaneously grasping the hypodermic needle with a first hand and pressing the limiter against the skin of the animal thereby stretching the skin of the animal, and expelling the substance by depressing the plunger with an index finger of the first hand or expelling the substance by depressing the plunger with a thumb of the first hand. The method further encompasses withdrawing the forward tip of the needle cannula from the skin of the subject after the substance has been injected into the skin of the subject. Still further, the method encompasses inserting the forward tip into the skin preferably to a depth of from approximately 1.0 mm to approximately 2.0 mm, and most preferably to a depth of 1.5 mm±0.2 to 0.3 mm.

Preferably, prior to inserting the needle cannula 24 (see FIG. 8-10), an injection site upon the skin of the subject is selected and cleaned. Subsequent to selecting and cleaning the site, the forward end 40 of the needle cannula 24 is inserted into the skin of the subject at an angle of generally 90 degrees until the skin engaging surface 42 contacts the skin. The skin engaging surface 42 prevents the needle cannula 42 from passing through the dermis layer of the skin and injecting the vaccine formulation into the subcutaneous layer. While the needle cannula 42 is inserted into the skin, the vaccine formulation is intradermally injected. The vaccine formulation may be prefilled into the syringe 60, either substantially before and stored therein just prior to making the injection. Several variations of the method of performing the injection may be utilized depending upon individual preferences and syringe type. In any event, the penetration of the needle cannula 42 is most preferably no more than about 1.5 mm because the skin engaging surface 42 prevents any further penetration.

Also, during the administration of an intradermal injection, the forward end 40 of the needle cannula 42 is embedded in the dermis layer of the skin which results in a reasonable amount of back pressure during the injection of the vaccine formulation of the invention. This back pressure could be on the order of 76 psi. In order to reach this pressure with a minimal amount of force having to be applied by the user to the plunger rod 66 of the syringe, a syringe barrel 60 with a small inside diameter is preferred such as 0.183" (4.65 mm) or less. The method of this invention thus comprises selecting a syringe for injection having an inside diameter of sufficient width to generate a force sufficient to overcome the back pressure of the dermis layer when the vaccine formulation is expelled from the syringe to make the injection.

In addition, since intradermal injections are typically carried out with small volumes of the vaccine formulation to be injected, i.e., on the order of no more than 0.5 ml, and preferably around 0.1 ml, a syringe barrel 60 with a small inside diameter is preferred to minimize dead space which could result in wasted substance captured between the stopper 70 and the shoulder of the syringe after the injection is completed. Also, because of the small volumes of vaccine formulation, on the order of 0.1 ml, a syringe barrel with a small inside diameter is preferred to minimize air head space between the level of the substance and the stopper 70 during process of inserting the stopper. Further, the small inside diameter enhances the ability to inspect and visualize the volume of the vaccine formulation within the barrel of the syringe.

The intradermal administration methods useful for carrying out the invention include both bolus and infusion delivery of the vaccine formulations to a subject, preferably a mammal, most preferably a human. A bolus dose is a single dose delivered in a single volume unit over a relatively brief period of time, typically less than about 10 minutes. Infusion administration comprises administering a fluid at a selected rate that may be constant or variable, over a relatively more extended time period, typically greater than about 10 minutes.

The intradermal delivery of the formulations into the intradermal space may occur either passively, without application of the external pressure or other driving means to the vaccine formulations to be delivered, and/or actively, with the application of pressure or other driving means. Examples of preferred pressure generating means include pumps, syringes, elastomer membranes, gas pressure, piezoelectric, electromotive, electromagnetic pumping, or Belleville springs or washers or combinations thereof. If desired, the rate of delivery of the intradermal vaccine formulations of the invention may be variably controlled by the pressure-generating means.

The vaccine formulations delivered or administered in accordance with the invention include solutions thereof in pharmaceutically acceptable diluents or solvents, suspensions, gels, particulates such as micro- and nanoparticles either suspended or dispersed, as well as in-situ forming vehicles of same.

The invention also encompasses varying the targeted depth of delivery of intradermal vaccine formulations of the invention. The targeted depth of delivery of intradermal vaccine formulations may be controlled manually by the practitioner, or with or without the assistance of an indicator to indicate when the desired depth is reached. Preferably however, the devices used in accordance with the invention have structural means for controlling skin penetration to the desired depth within the intradermal space. The targeted depth of delivery may be varied using any of the methods described in U.S. patent application Ser. No. 09/417,671, filed on Oct. 14, 1999; Ser. No. 09/606,909, filed on Jun. 29, 2000; Ser. No. 09/893,746, filed on Jun. 29, 2001; Ser. No. 10/028,989, filed on Dec. 28, 2001; Ser. No. 10/028,988, filed on Dec. 28, 2001; or International Publication No. EP 10922 444, published Apr. 18, 2001; WO 01/02178, published Jan. 10, 2002; and WO 02/02179, published Jan. 10, 2002; all of which are incorporated herein by reference in their entirety.

The dosage of the intradermal vaccine formulation of the invention depends on the antigenic or immunogenic agent in the formulation. The dosage of the intradermal vaccine formulation may be determined using standard immunological methods known in the art, for example, by first identifying doses effective to elicit a prophylactic or therapeutic immune response, e.g., by measuring the serum titer of antigen specific immunoglobulins, relative to a control formulation, e.g., a formulation simply consisting of the antigenic or immunogenic agent without a molecule as disclosed herein. Preferably, the effective dose is determined in an animal model, prior to use in humans. Most preferably, the optimal dose is determined in an animal whose skin thickness approximates closely to that of human skin, e.g., pig.

Intradermal vaccine formulations of the invention may also be administered on a dosage schedule, for example, an initial administration of the vaccine formulation with subsequent booster administrations. In particular embodiments, a second dose of the vaccine formulation is administered anywhere from two weeks to one year, preferably from one to six months, after the initial administration. Additionally, a third dose may be administered after the second dose and from three months to two years, or even longer, preferably 4 to 6 months, or 6 months to one year after the initial administration. In most preferred embodiments, however no booster immunization is required.

The vaccine formulations of the invention are administered using any of the devices and methods known in the art or disclosed in WO 01/02178, published Jan. 10, 2002; and WO 02/02179, published Jan. 10, 2002, U.S. Pat. No. 6,494,865, issued Dec. 17, 2002 and U.S. Pat. No. 6,569,143 issued May 27, 2003 all of which are incorporated herein by reference in their entirety. Preferably the devices for intradermal administration in accordance with the methods of the invention have structural means for controlling skin penetration to the desired depth within the intradermal space. This is most typically accomplished by means of a widened area or hub associated with the shaft of the dermal-access means that may take the form of a backing structure or platform to which the needles are attached. The length of microneedles as dermal-access means are easily varied during the fabrication process and are routinely produced in less than 2 mm length. Microneedles are also a very sharp and of a very small gauge, to further reduce pain and other sensation during the injection or infusion. They may be used in the invention as individual single-lumen microneedles or multiple microneedles may be assembled or fabricated in linear arrays or two-dimensional arrays as to increase the rate of delivery or the amount of substance delivered in a given period of time. The needle may eject its substance from the end, the side or both. Microneedles may be incorporated into a variety of devices such as holders and housings that may also serve to limit the depth of penetration. The dermal-access means of the invention may also incorporate reservoirs to contain the substance prior to delivery or pumps or other means for delivering the drug or other substance under pressure. Alternatively, the device housing the dermal-access means may be linked externally to such additional components.

The intradermal methods of administration comprise microneedle-based injection and infusion systems or any other means to accurately target the intradermal space. The intradermal methods of administration encompass not only microdevice-based injection means, but other delivery methods such as needle-less or needle-free ballistic injection of fluids or powders into the intradermal space, Mantoux-type intradermal injection, enhanced ionotophoresis through microdevices, and direct deposition of fluid, solids, or other dosing forms into the skin.

In some embodiments, the present invention provides a drug delivery device including a needle assembly for use in making intradermal injections. The needle assembly has an adapter that is attachable to prefillable containers such as syringes and the like. The needle assembly is supported by the adapter and has a hollow body with a forward end extending away from the adapter. A limiter surrounds the needle and extends away from the adapter toward the forward end of the needle. The limiter has a skin engaging surface that is adapted to be received against the skin of an animal such as a human. The needle forward end extends away from the skin engaging surface a selected distance such that the limiter limits the amount or depth that the needle is able to penetrate through the skin of an animal In a specific embodiment, the hypodermic needle assembly for use in the methods of the invention comprises the elements necessary to perform the present invention directed to an improved method for delivering vaccine formulations into the skin of a subject's skin, preferably a human subject's skin, comprising the steps of providing a drug delivery device including a needle cannula having a forward needle tip and the needle cannula being in fluid communication with a substance contained in the drug delivery device and including a limiter portion surrounding the needle cannula and the limiter portion including a skin engaging surface, with the needle tip of the needle cannula extending from the limiter portion beyond the skin engaging surface a distance equal to approximately 0.5 mm to approximately 3.0 mm and the needle cannula having a fixed angle of orientation relative to a plane of the skin engaging surface of the limiter portion, inserting the needle tip into the skin of an animal and engaging the surface of the skin with the skin engaging surface of the limiter portion, such that the skin engaging surface of the limiter portion limits penetration of the needle cannula tip into the dermis layer of the skin of the animal, and expelling the substance from the drug delivery device through the needle cannula tip into the skin of the animal.

In a specific embodiment, the invention encompasses a drug delivery device as disclosed in FIG. 8-FIG. 10 illustrate an example of a drug delivery device which can be used to practice the methods of the present invention for making intradermal injections illustrated in FIGS. 8-10. The device 10 illustrated in FIGS. 8-10 includes a needle assembly 20 which can be attached to a syringe barrel 60. Other forms of delivery devices may be used including pens of the types disclosed in U.S. Pat. No. 5,279,586, U.S. patent application Ser. No. 09/027,607 and PCT Application No. WO 00/09135, the disclosure of which are hereby incorporated by reference in their entirety. The needle assembly 20 includes a hub 22 that supports a needle cannula 24. The limiter 26 receives at least a portion of the hub 22 so that the limiter 26 generally surrounds the needle cannula 24 as best seen in FIG. 9.

One end 30 of the hub 22 is able to be secured to a receiver 32 of a syringe. A variety of syringe types for containing the substance to be intradermally delivered according to the present invention can be used with a needle assembly designed, with several examples being given below. The opposite end of the hub 22 preferably includes extensions 34 that are nestingly received against abutment surfaces 36 within the limiter 26. A plurality of ribs 38 preferably are provided on the limiter 26 to provide structural integrity and to facilitate handling the needle assembly 20.

By appropriately designing the size of the components, a distance "d" between a forward end or tip 40 of the needle 24 and a skin engaging surface 42 on the limiter 26 can be tightly controlled. The distance "d" preferably is in a range from approximately 0.5 mm to approximately 3.0 nm, and most preferably around 1.5 mm±0.2 mm to 0.3 mm. When the forward end 40 of the needle cannula 24 extends beyond the skin engaging surface 42 a distance within that range, an intradermal injection is ensured because the needle is unable to penetrate any further than the typical dermis layer of an animal. Typically, the outer skin layer, epidermis, has a thickness between 50-200 microns, and the dermis, the inner and thicker layer of the skin, has a thickness between 1.5-3.5 mm. Below the dermis layer is subcutaneous tissue (also sometimes referred to as the hypodermis layer) and muscle tissue, in that order.

As can be best seen in FIG. 9, the limiter 26 includes an opening 44 through which the forward end 40 of the needle cannula 24 protrudes. The dimensional relationship between the opening 44 and the forward end 40 can be controlled depending on the requirements of a particular situation. In the illustrated embodiment, the skin engaging surface 42 is generally planar or flat and continuous to provide a stable placement of the needle assembly 20 against an animal's skin. Although not specifically illustrated, it may be advantageous to have the generally planar skin engaging surface 42 include either raised portions in the form of ribs or recessed portions in the form of grooves in order to enhance stability or facilitate attachment of a needle shield to the needle tip 40. Additionally, the ribs 38 along the sides of the limiter 26 may be extended beyond the plane of the skin engaging surface 42.

Regardless of the shape or contour of the skin engaging surface 42, the preferred embodiment includes enough generally planar or flat surface area that contacts the skin to facilitate stabilizing the injector relative to the subject's skin. In the most preferred arrangement, the skin engaging surface 42 facilitates maintaining the injector in a generally perpendicular orientation relative to the skin surface and facilitates the application of pressure against the skin during injection. Thus, in the preferred embodiment, the limiter has dimension or outside diameter of at least 5 mm. The major dimension will depend upon the application and packaging limitations, but a convenient diameter is less than 15 mm or more preferably 11-12 mm.

It is important to note that although FIGS. 8 and 9 illustrate a two-piece assembly where the hub 22 is made separate from the limiter 26, a device for use in connection with the invention is not limited to such an arrangement. Forming the hub 22 and limiter 26 integrally from a single piece of plastic material is an alternative to the example shown in FIGS. 8 and 9. Additionally, it is possible to adhesively or otherwise secure the hub 22 to the limiter 26 in the position illustrated in FIG. 8 so that the needle assembly 20 becomes a single piece unit upon assembly.

Having a hub 22 and limiter 26 provides the advantage of making an intradermal needle practical to manufacture. The preferred needle size is a small Gauge hypodermic needle, commonly known as a 30 Gauge or 31 Gauge needle. Having such a small diameter needle presents a challenge to make a needle short enough to prevent undue penetration beyond the dermis layer of an animal. The limiter 26 and the hub 22 facilitate utilizing a needle 24 that has an overall length that is much greater than the effective length of the needle, which penetrates the individual's tissue during an injection. With a needle assembly designed in accordance herewith, manufacturing is enhanced because larger length needles can be handled during the manufacturing and assembly processes while still obtaining the advantages of having a short needle for purposes of completing an intradermal injection.

FIG. 9 illustrates the needle assembly 20 secured to a drug container such as a syringe 60 to form the device 10. A generally cylindrical syringe body 62 can be made of plastic or glass as is known in the art. The syringe body 62 provides a reservoir 64 for containing the substance to be administered during an injection. A plunger rod 66 has a manual activation flange 68 at one end with a stopper 70 at an opposite end as known in the art. Manual movement of the plunger rod 66 through the reservoir 64 forces the substance within the reservoir 64 to be expelled out of the end 40 of the needle as desired.

The hub 22 can be secured to the syringe body 62 in a variety of known manners. In one example, an interference fit is provided between the interior of the hub 22 and the exterior of the outlet port portion 72 of the syringe body 62. In another example, a conventional Luer fit arrangement is provided to secure the hub 22 on the end of the syringe 60. As can be appreciated from FIG. 10, such needle assembly designed is readily adaptable to a wide variety of conventional syringe styles.

This invention provides an intradermal needle injector that is adaptable to be used with a variety of syringe types. Therefore, this invention provides the significant advantage of facilitating manufacture and assembly of intradermal needles on a mass production scale in an economical fashion.

Prior to inserting the needle cannula 24, an injection site upon the skin of the animal is selected and cleaned. Subsequent to selecting and cleaning the site, the forward end 40 of the needle cannula 24 is inserted into the skin of the animal at an angle of generally 90 degrees until the skin engaging surface 42 contacts the skin. The skin engaging surface 42 prevents the needle cannula 42 from passing through the dermis layer of the skin and injecting the substance into the subcutaneous layer.

While the needle cannula 42 is inserted into the skin, the substance is intradermally injected. The substance may be prefilled into the syringe 60, either substantially before and stored therein just prior to making the injection. Several variations of the method of performing the injection may be utilized depending upon individual preferences and syringe type. In any event, the penetration of the needle cannula 42 is most preferably no more than about 1.5 mm because the skin engaging surface 42 prevents any further penetration.

Also, during the administration of an intradermal injection, the forward end 40 of the needle cannula 42 is embedded in the dermis layer of the skin which results in a reasonable amount of back pressure during the injection of the substance. This back pressure could be on the order of 76 psi. In order to reach this pressure with a minimal amount of force having to be applied by the user to the plunger rod 66 of the syringe, a syringe barrel 60 with a small inside diameter is preferred such as 0.183" (4.65 mm) or less. The method of this invention thus includes selecting a syringe for injection having an inside diameter of sufficient width to generate a force sufficient to overcome the back pressure of the dermis layer when the substance is expelled from the syringe to make the injection.

In addition, since intradermal injections are typically carried out with small volumes of the substance to be injected, i.e., on the order of no more than 0.5 ml, and preferably around 0.1 ml, a syringe barrel 60 with a small inside diameter is preferred to minimize dead space which could result in wasted substance captured between the stopper 70 and the shoulder of the syringe after the injection is completed. Also, because of the small volumes of substance, on the order of 0.1 ml, a syringe barrel with a small inside diameter is preferred to minimize air head space between the level of the substance and the stopper 70 during process of inserting the stopper. Further, the small inside diameter enhances the ability to inspect and visualize the volume of the substance within the barrel of the syringe.

As shown in FIGS. 8-10, the syringe 60 may be grasped with a first hand 112 and the plunger 66 depressed with the forefinger 114 of a second hand 116. Alternatively, as shown in FIGS. 8-10 the plunger 66 may be depressed by the thumb 118 of the second hand 116 while the syringe 60 is held by the first hand. In each of these variations, the skin of the animal is depressed, and stretched by the skin engaging surface 42 on the limiter 26. The skin is contacted by neither the first hand 112 nor the second hand 116.

An additional variation has proven effective for administering the intradermal injection of the present invention. This variation includes gripping the syringe 60 with the same hand that is used to depress the plunger 66. FIG. 9 shows the syringe 60 being gripped with the first hand 112 while the plunger is simultaneously depressed with the thumb 120 of the first hand 112. This variation includes stretching the skin with the second hand 114 while the injection is being made. Alternatively, as shown in FIG. 10, the grip is reversed and the plunger is depressed by the forefinger 122 of the first hand 112 while the skin is being stretched by the second hand 116. However, it is believed that this manual stretching of the skin is unnecessary and merely represents a variation out of habit from using the standard technique.

In each of the variations described above, the needle cannula 24 is inserted only about 1.5 mm into the skin of the animal. Subsequent to administering the injection, the needle cannula 24 is withdrawn from the skin and the syringe 60 and needle assembly 20 are disposed of in an appropriate manner. Each of the variations were utilized in clinical trials to determine the effectiveness of both the needle assembly 20 and the present method of administering the intradermal injection.

The present invention encompasses any device for accurately and selectively targeting the junctional layer of a subject's skin. The nature of the device used is not critical as long as it penetrates the skin of the subject to the targeted depth within the junctional region without passing through it. Preferably, the device penetrates the skin at a depth of at least about 2 mm, up to a depth of no more than about 3 mm, most preferably, no more than about 2.5 mm.

5.7 Administration of the Epidermal Vaccine Formulations

The epidermal methods of administration comprise any method and device known in the art for accurately targeting the epidermal compartment such as those disclosed in U.S. Provisional patent application Nos. 60/330,713, 60/333,162 and U.S. application Ser. No. 09/576,643, 10/282,231, filed Oct. 29, 2001, Nov. 27, 2001, and May 22, 2000 and Oct. 29, 2002, respectively, all of which are each hereby incorporated by reference in their entirety. The present invention encompasses micoabrading devices for accurately targeting the epidermal space. These devices may have solid or hollow micro-protrusions. The micro-protrusions can have a length up to about 500 microns. Suitable micro-protrusions have a length of about 50 to 500 microns. Preferably the microprotrusions have a length of about 50 to 300 microns and more preferably in the range of about 150 to 250 microns, with 180 to 220 microns being most preferred.

The microabrader devices that may be used in the methods of the invention are preferably a device capable of abrading the skin such as those exemplified in FIGS. 11-16. In preferred embodiments, the device is capable of abrading the skin thereby penetrating the stratum corneum without piercing the stratum corneum.

As used herein, "penetrating" refers to entering the stratum corneum without passing completely through the stratum corneum and entering into the adjacent layers. This is not to say that that the stratum corneum can not be completely penetrated to reveal the interface of the underlying layer of the skin. Piercing, on the other hand, refers to passing through the stratum corneum completely and entering into the adjacent layers below the stratum corneum. As used herein, the term "abrade" refers to removing at least a portion of the stratum corneum to increase the permeability of the skin without causing excessive skin irritation or compromising the skin's barrier to infectious agents. The term "abrasion" as used herein refers to disruption of the outer layers of the skin, for example by scraping or rubbing, resulting in an area of disrupted stratum corneum. This is in contrast to "puncturing" which produces discrete holes through the stratum corneum with areas of undisrupted stratum corneum between the holes.

Preferably, the devices used for epidermal delivery in accordance with the methods of the invention penetrate, but do not pierce, the stratum corneum. The vaccine formulation to be administered using the methods of this invention may be applied to the skin prior to abrading, simultaneous with abrading, or post-abrading.

In a specific embodiment the invention encompasses a method for delivering a vaccine formulation into the skin of a patient comprising the steps of coating a patient's outer skin layer or a microabrader 2, see FIG. 11B with the formulation and moving microabrader 2 across the patient's skin to provide abrasions leaving furrows sufficient to permit entry of the formulation into the patient's viable epidermis. Due to the structural design of microabrader 2, the leading edge of microabrader 2 first stretches the patient's skin and then the top surface of microabrader 2 abrades the outer protective formulation e to enter the patient. After the initial abrasion of the outer protective skin layer, the trailing and leading edges of microabrader 2 can rub the surface of the abraded area working the formulation into the abraded skin area thereby improving its medicinal effect. As shown in FIGS. 11B, 12A and 12B, microabrader 2 includes base 4 onto which an abrading surface 5 can be mounted. Alternatively, the abrading surface may be integral with the base and fabricated as a single two-component part. Preferably, base 4 is a solid molded piece. In one embodiment, base 4 is configured with a mushroom-like crown 4b that curves upward and is truncated at the top. The top of base 4 is generally flat with abrading surface 5 being mounted thereon or integral therewith. Alternatively, the truncated top may have a recess for receiving abrading surface 5. In all embodiments, abrading surface 5 includes a platform with an array of microprotrusions that extends above the truncated top. In another embodiment of the microabrader, the handle, base and abrading surface may be integral with one another and fabricated as a single three-component device. Microabrader 2 is applied to a subject by moving microabrader 2 across the subject's skin with enough pressure to enable abrading surface 5 to open the outer protective skin or stratum corneum of the subject. The inward pressure applied to the base causes microabrader 2 to be pressed into the subject's skin. Accordingly, it is preferable that the height of the sloping mushroom-like crown 4b be sufficient to prevent the applied substance from flowing over and onto the facet 4c when microabrader 2 is being used. As will be described below, abrading surface 5 comprises an array of microprotrusions.

A handle 6 is attached to base 4 or may be integral with base 4. As shown in FIG. 12A, an upper end 6a of the handle may be either snap fit or friction fit between the inner circumferential sidewall 4a of base 4. Alternatively, as shown in FIGS. 11A and 12A, handle 6 may be glued (e.g., with epoxy) to the underside 4c of base 4. Alternatively, the handle and base may be fabricated (e.g., injection-molded) together as a single two-component part. The handle may be of a diameter that is less than the diameter of the base or may be of a similar diameter as the base. Underside 4c of base 4 may be flush with mushroom-like crown 4b or extend beyond the mushroom-like crown. The lower end 6b of handle 6 may be wider than the shaft 6c of handle 6 or may be of a similar diameter as shaft. Lower end 6b may include an impression 6d that serves as a thumb rest for a person administering the substance and moving microabrader 2. In addition, protrusions 8 are formed on the outside of handle 6 to assist a user in firmly gripping handle 6 when moving the same against or across a patient's skin.

As shown in the cross-section of FIG. 11B in FIG. 12B, lower end 6b may be cylindrical. Microabrader 2 may be made of a transparent material, as shown in FIG. 12A. Impressions 6d are disposed on both sides of the cylindrical lower end 6b to assist a person using microabrader 2 to grip the same. That is, the movement of microabrader 2 can be provided by hand or fingers. The handle 6, as well as the base 4, of the microabrader is preferably molded out of plastic or the like material. The microabrader 2 is preferably inexpensively manufactured so that the entire microabrader and abrading surface can be disposed after its use on one patient.

Abrading surface 5 is designed so that when microabrader 2 is moved across a patient's skin, the resultant abrasions penetrate the stratum corneum. Abrading surface 5 may be coated with a formulation desired to be delivered to the patient's viable epidermis.

In order to achieve the desired abrasions, the microabrader 2 should be moved across a patient's skin at least once. The patient's skin may be abraded in alternating directions. The structural design of the microabrader according to the invention enables the formulation to be absorbed more effectively thereby allowing less of the formulation to be applied to a patient's skin or coating abrading surface 5. Abrading surface 5 may be coated with a formulation desired to be delivered to the patient. In one embodiment, the formulation may be a powder disposed on abrading surface 5. In another embodiment, the formulation to be delivered may be applied directly to the patient's skin prior to the application and movement of microabrader 2 on the patient's skin.

Figure 13:
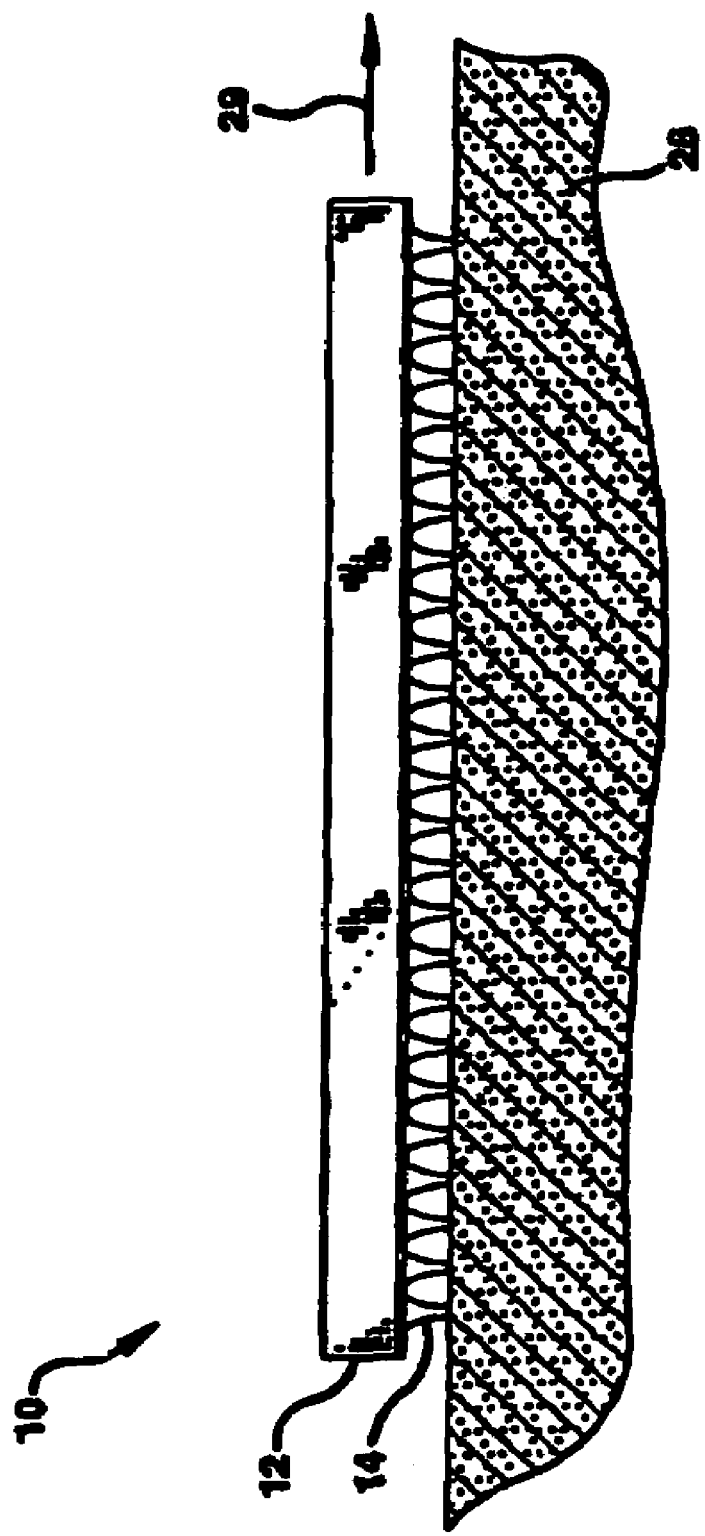
FIG. 13 is a side view of the abrading surface the microabrader device of FIGS. 11A, 11B, 12A, and 12B on the skin of a subject.

Referring to FIG. 13, the microabrader device 10 of the invention includes a substantially planar body or abrading surface support 12 having a plurality of microprotrusions 14 extending from the bottom surface of the support. The support generally has a thickness sufficient to allow attachment of the surface to the base of the microabrader device thereby allowing the device to be handled easily as shown in FIGS. 11B, 12A and 12B. Alternatively, a differing handle or gripping device can be attached to or be integral with the top surface of the abrading surface support 12. The dimensions of the abrading surface support 12 can vary depending on the length of the microprotrusions, the number of microprotrusions in a given area and the amount of the formulation to be administered to the patient. Typically, the abrading surface support 12 has a surface area of about 1 to 4 cm$^2$. In preferred embodiments, the abrading surface support 12 has a surface area of about 1 cm$^2$.

Figure 14A:
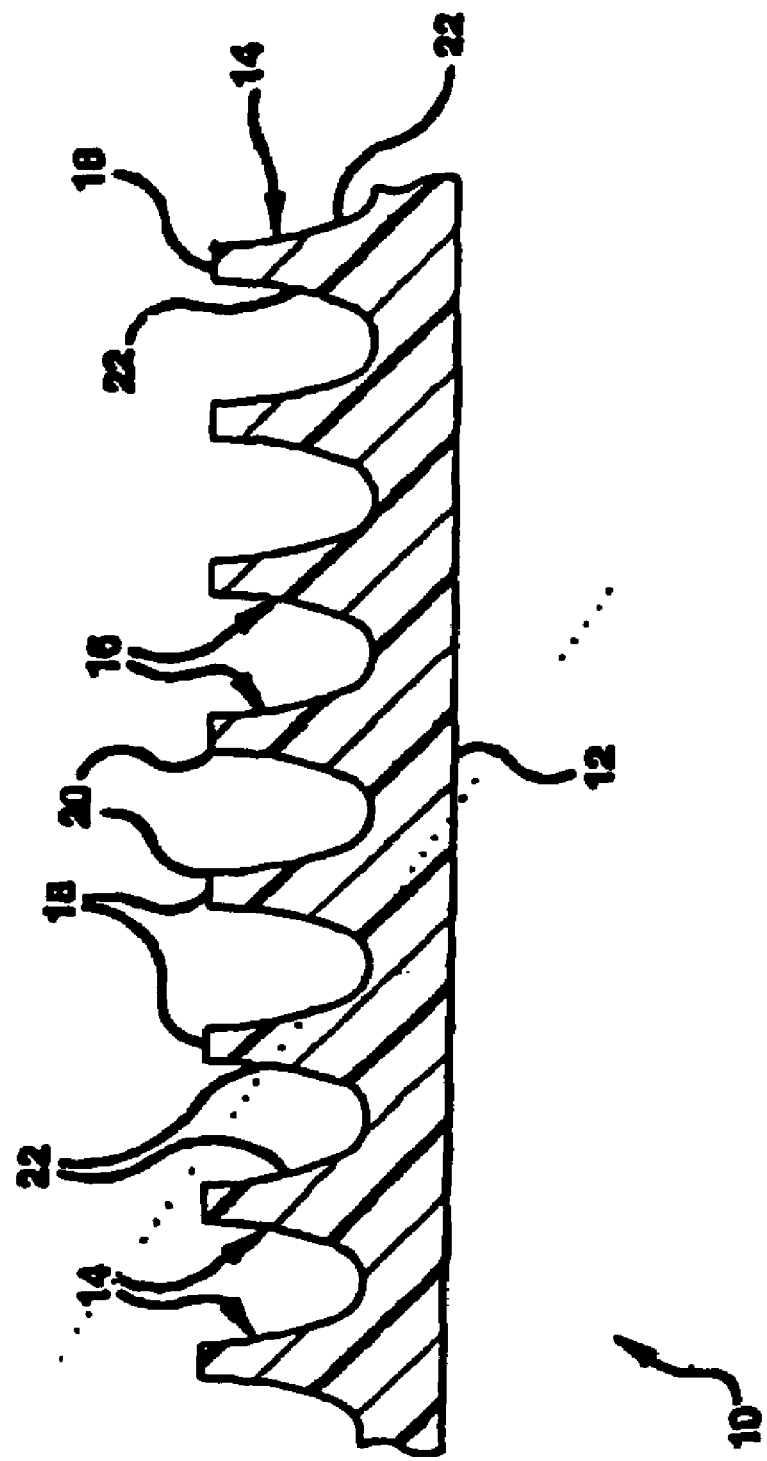
FIG. 14A is a perspective view of the abrading surface in the embodiment of FIG. 13.
Figure 14B:
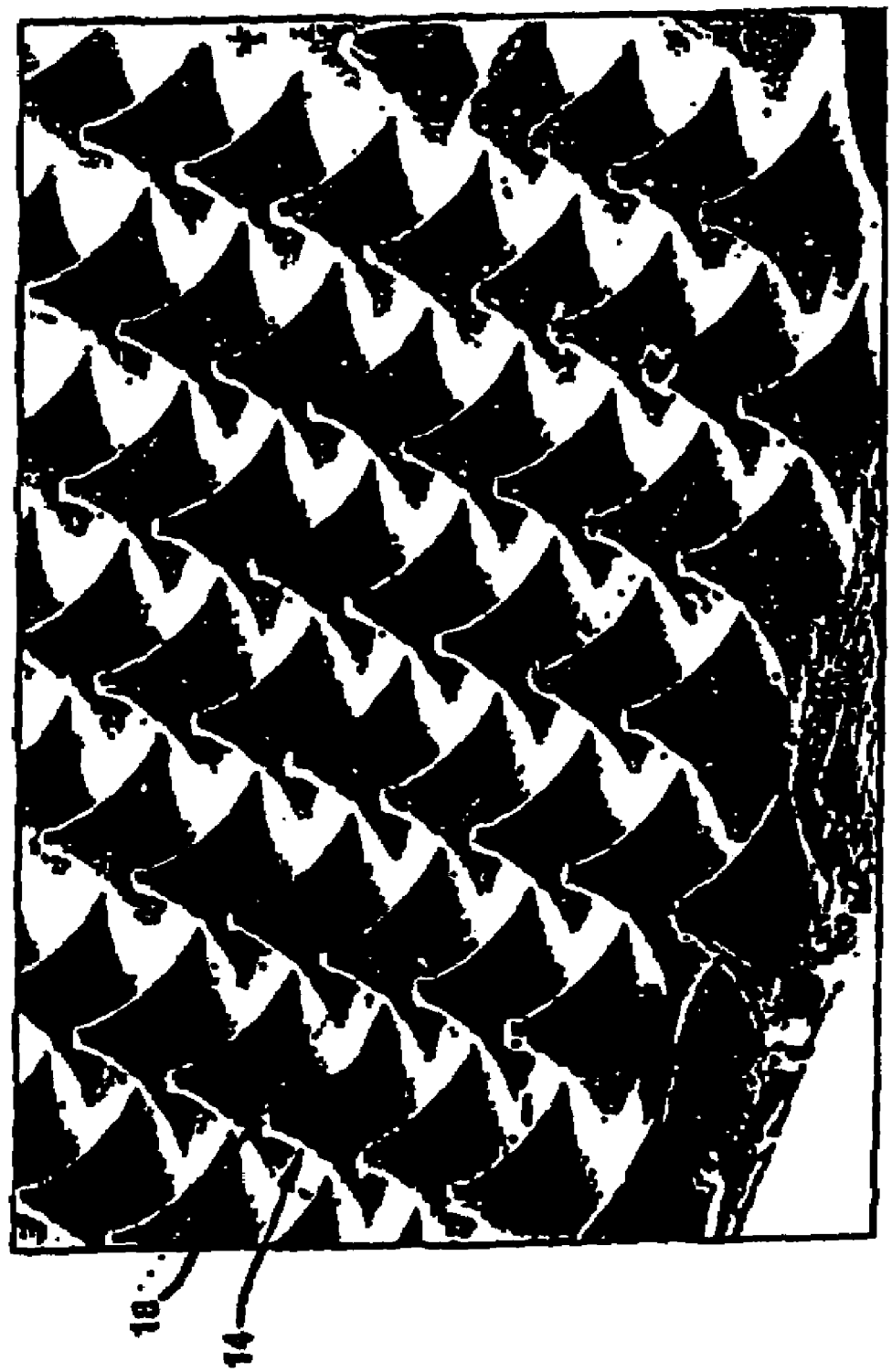
FIG. 14B is a cross sectional side view of the abrader surface.
Figure 15:
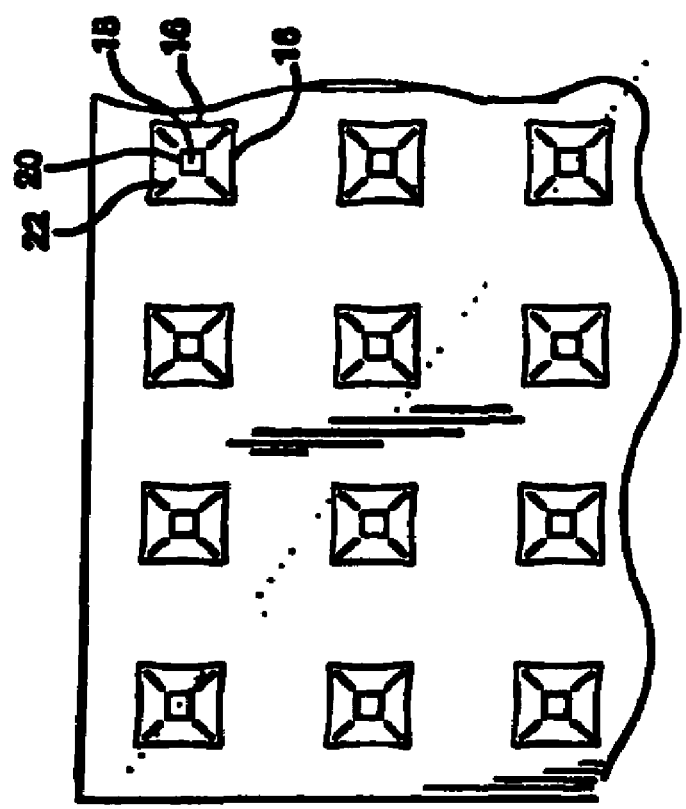
FIG. 15 is a bottom view of the abrader surface of the embodiment of FIG. 13.

As shown in FIGS. 13, 14, 14A and 15, the microprotrusions 14 project from the surface of the abrading surface support 12 and are substantially perpendicular to the plane of the abrading surface support 12. The microprotrusions in the illustrated embodiment are arranged in a plurality of rows and columns and are preferably spaced apart a uniform distance. The microprotrusions 14 have a generally pyramid shape with sides 16 extending to a tip 18. The sides 16 as shown have a generally concave profile when viewed in cross-section and form a curved surface extending from the abrading surface support 12 to the tip 18. In the embodiment illustrated, the microprotrusions are formed by four sides 16 of substantially equal shape and dimension. As shown in FIGS. 14A and 15, each of the sides 16 of the microprotrusions 14 have opposite side edges contiguous with an adjacent side and form a scraping edge 22 extending outward from the abrading surface support 12. The scraping edges 22 define a generally triangular or trapezoidal scraping surface corresponding to the shape of the side 16. In further embodiments, the microprotrusions 14 can be formed with fewer or more sides.

The microprotrusions 14 preferably terminate at blunt tips 18. Generally, the tip 18 is substantially flat and parallel to the support 14. When the tips are flat, the total length of the microprotrusions do not penetrate the skin; thus, the length of the microprotrusions is greater than the total depth to which said microprotrusions penetrate said skin. The tip 18 preferably forms a well defined, sharp edge 20 where it meets the sides 16. The edge 20 extends substantially parallel to the abrading surface support 12 and defines a further scraping edge. In further embodiments, the edge 20 can be slightly rounded to form a smooth transition from the sides 16 to the tip 18. Preferably, the microprotrusions are frustoconical or frustopyramidal in shape.

The microabrader device 10 and the microprotrusions can be made from a plastic material that is non-reactive with the substance being administered. A non-inclusive list of suitable plastic materials include, for example, polyethylene, polypropylene, polyamides, polystyrenes, polyesters, and polycarbonates as known in the art. Alternatively, the microprotrusions can be made from a metal such as stainless steel, tungsten steel, alloys of nickel, molybdenum, chromium, cobalt, titanium, and alloys thereof, or other materials such as silicon, ceramics and glass polymers. Metal microprotrusions can be manufactured using various techniques similar to photolithographic etching of a silicon wafer or micromachining using a diamond tipped mill as known in the art. The microprotrusions can also be manufactured by photolithographic etching of a silicon wafer using standard techniques as are known in the art. They can also be manufactured in plastic via an injection molding process, as described for example in U.S. application Ser. No. 10/193,317, filed Jul. 12, 2002, which is hereby incorporated by reference.

The length and thickness of the microprotrusions are selected based on the particular substance being administered and the thickness of the stratum corneum in the location where the device is to be applied. Preferably, the microprotrusions penetrate the stratum corneum substantially without piercing or passing through the stratum corneum. The microprotrusions can have a length up to about 500 microns. Suitable microprotrusions have a length of about 50 to 500 microns. Preferably, the microprotrusions have a length of about 50 to about 300 microns, and more preferably in the range of about 150 to 250 microns, with 180 to 220 microns most preferred. The microprotrusions in the illustrated embodiment have a generally pyramidal shape and are perpendicular to the plane of the device. These shapes have particular advantages in insuring that abrasion occurs to the desired depth. In preferred embodiments, the microprotrusions are solid members. In alternative embodiments, the microprotrusions can be hollow.

As shown in FIGS. 12 and 15, the microprotrusions are preferably spaced apart uniformly in rows and columns to form an array for contacting the skin and penetrating the stratum corneum during abrasion. The spacing between the microprotrusions can be varied depending on the substance being administered either on the surface of the skin or within the tissue of the skin. Typically, the rows of microprotrusions are spaced to provide a density of about 2 to about 10 per millimeter (mm). Generally, the rows or columns are spaced apart a distance substantially equal to the spacing of the microprotrusions in the array to provide a microprotrusion density of about 4 to about 100 microprotrusions per mm$^2$. In another embodiment, the microprotrusions may be arranged in a circular pattern. In yet another embodiment, the microprotrusions may be arranged in a random pattern. When arranged in columns and rows, the distance between the centers of the microprotrusions is preferably at least twice the length of the microprotrusions. In one preferred embodiment, the distance between the centers of the microprotrusions is twice the length of the microprotrusions 110 microns. Wider spacings are also included, up to 3, 4, 5 and greater multiples of the length of the micoprotrusions. In addition, as noted above, the configuration of the microprotrusions can be such, that the height to the microprotrusions can be greater than the depth into the skin those protrusions will penetrate.

The flat upper surface of the frustoconical or frustopyramidal microprotrusions is generally 10 to 100, preferably 30-70, and most preferably 35-50 microns in width.

The method of preparing a delivery site on the skin places the microabrader against the skin 28 of the patient in the desired location. The microabrader is gently pressed against the skin and then moved over or across the skin. The length of the stroke of the microabrader can vary depending on the desired size of the delivery site, defined by the delivery area desired. The dimensions of the delivery site are selected to accomplish the intended result and can vary depending on the substance, and the form of the substance, being delivered. For example, the delivery site can cover a large area for treating a rash or a skin disease. Generally, the microabrader is moved about 2 to 15 centimeters (cm). In some embodiments of the invention, the microabrader is moved to produce an abraded site having a surface area of about 4 $cm^2$ to about 300 $cm^2$.

The microabrader is then lifted from the skin to expose the abraded area and a suitable delivery device, patch or topical formulation may be applied to the abraded area. Alternatively, the substance to be administered may be applied to the surface of the skin either before, or simultaneously with abrasion.

The extent of the abrasion of the stratum corneum is dependent on the pressure applied during movement and the number of repetitions with the microabrader. In one embodiment, the microabrader is lifted from the skin after making the first pass and placed back onto the starting position in substantially the same place and position. The microabrader is then moved a second time in the same direction and for the same distance. In another embodiment, the microabrader is moved repetitively across the same site in alternating direction without being lifted from the skin after making the first pass. Generally, two or more passes are made with the microabrader.

Figure 16:
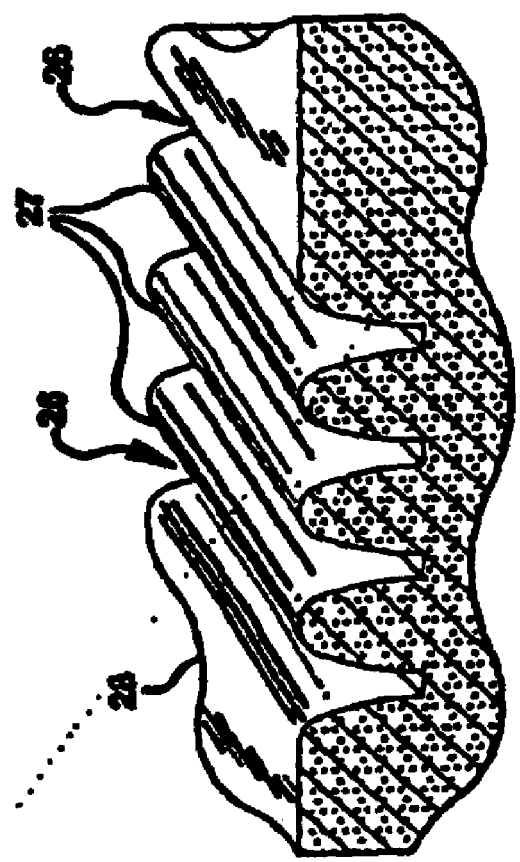
FIG. 16 is a perspective view in partial cross section of abraded furrows of skin.

In further embodiments, the microabrader can be swiped back and forth, in the same direction only, in a grid-like pattern, a circular pattern, or in some other pattern for a time sufficient to abrade the stratum corneum a suitable depth to enhance the delivery of the desired substance. The linear movement of the microabrader across the skin 28 in one direction removes some of the tissue to form grooves 26, separated by peaks 27 in the skin 28 corresponding to substantially each row of microprotrusions as shown in FIG. 16. The edges 20, 22 and the blunt tip 18 of the microprotrusions provide a scraping or abrading action to remove a portion of the stratum corneum to form a groove or furrow in the skin rather than a simple cutting action. The edges 20 of the blunt tips 18 of the microprotrusions 14 scrape and remove some of the tissue at the bottom of the grooves 26 and allows them to remain open, thereby allowing the substance to enter the grooves for absorption by the body. Preferably, the microprotrusions 14 are of sufficient length to penetrate the stratum corneum and to form grooves 26 having sufficient depth to allow absorption of the substance applied to the abraded area without inducing pain or unnecessary discomfort to the patient. Preferably, the grooves 26 do not pierce but can extend through the stratum corneum. The edges 22 of the pyramid shaped microprotrusions 14 form scraping edges that extend from the abrading surface support 12 to the tip 18. The edges 22 adjacent the abrading surface support 12 form scraping surfaces between the microprotrusions which scrape and abrade the peaks 27 formed by the skin between the grooves 26. The peaks 27 formed between the grooves generally are abraded slightly.

Any device known in the art for disruption of the stratum corneum by abrasion can be used in the methods of the invention. These include for example, microelectromechanical (MEMS) devices with arrays of short microneedles or microprotrusions, sandpaper-like devices, scrapers and the like.

The actual method by which the epidermal vaccine formulations of the invention are targeted to the epidermal space is not critical as long as it penetrates the skin of a subject to the desired targeted depth. The microabraiders discussed within initially deposit the inventive formulations to a skin depth of 0.0 to 0.025 mm and preferably not exceeding the statum corneum.

5.8 Determination of Efficacy of the Dermal Vaccine Formulations

The invention encompasses methods for determining the efficacy of the dermal vaccine formulations using any standard method known in the art or described herein. The assay for determining the efficacy of the dermal vaccine formulations of the invention may be in vitro based assays or in vivo based assays, including animal based assays. In some embodiments, the invention encompasses detecting and/or quantitating a humoral immune response against the antigenic or immunogenic agent of an dermal formulation of the invention in a sample, e.g., serum, obtained from a subject who has been administered a vaccine formulation of the invention. Preferably, the humoral immune response stimulated by the dermal vaccine formulations of the invention are compared to a control sample obtained from the similar subject, who has been administered a control formulation, e.g., a formulation which simply comprises of the antigenic or immunogenic agent.

Assays for measuring humoral immune response are well known in the art, e.g., see, Coligan et al., (eds.), 1997, *Current Protocols in Immunology*, John Wiley and Sons, Inc., Section 2.1. A humoral immune response may be detected and/or quantitated using standard methods known in the art including, but not limited to, an ELISA assay. Preferably, the humoral immune response is measured by detecting and/or quantitating the relative amount of an antibody which specifically recognizes an antigenic or immunogenic agent in the sera of a subject who has been treated with an intradermal vaccine formulation of the invention relative to the amount of the antibody in an untreated subject. ELISA assays can be used to determine total antibody titres in a sample obtained from a subject treated with a formulation of the invention. In other embodiments, ELISA assays may be used to determine the level of isotype specific antibodies using methods known in the art.

ELISA based assays comprise preparing an antigen, coating the well of a 96 well microtiter plate with the antigen, adding an antibody specific to the antigen conjugated to a detectable compound such as an enzymatic substrate (e.g., horseradish peroxidase or alkaline phosphatase) to the well and incubating for a period of time, and detecting the presence of the antigen. In an ELISA assay, the antibody does not have to be conjugated to a detectable compound; instead, a second antibody (which recognizes the first antibody) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, *Current Protocols in Molecular Biology*, Vol. 1, John Wiley & Sons, Inc., New York at 11.2.1.

In a specific embodiment, when the vaccine formulation comprises an influenza antigen any method known in the art for the detection and/or quantitation of an antibody response against an influenza antigen is encompassed within the methods of the invention. An exemplary method for determining an influenza antigen directed antibody response may comprise the following: an influenza antigen is used to coat a microtitre plate (Nunc plate); sera from a subject treated with an influenza vaccine formulation of the invention is added to the plate; antisera is added to the plate and incubated for a sufficient time to allow a complex to be formed, i.e., a complex between an antibody in the sera and the antigen. The complex is then detected using standard methods in the art. For exemplary assays for measuring an influenza specific antibody response see, e.g., Newman et al., 1997, *Mechanism of Aging & Development*, 93: 189-203; Katz et al., 2000, *Vaccine*, 18: 2177-87; Todd et al., (Brown and Haaheim, eds.), 1998 in *Modulation of the Immune Response to Vaccine Antigens*, Dev. Biol. Stand. Basel, Karger, 92: 341-51; Kendal et al., 1982, in *Concepts and Procedures for Laboratory-based Influenza Surveillance*, Atlanta: CDC, B17-35; Rowe et al., 1999, *J. Clin. Micro.* 37: 937-43; Todd et al., 1997, Vaccine 15: 564-70; WHO Collaborating Centers for Reference and Research on Influenza, in Concepts and Procedures for Laboratory-based Influenza Surveillance, 1982, p. B-23; all of which are incorporated herein by reference in their entirety.

In a specific embodiment, antibody response to an influenza vaccine formulation of the invention comprises: coating an influenza antigen, e.g., an antigen from the A/PR8/34 strain (specifically Influenza APR384 purified/inactivated at a concentration of 2 mg/mL from Charles River SPAFAS), as the test antigen on a microtitre plate (e.g., 96-well Immuno-Plate™ with MaxiSorp™ Surface). The coating solution preferably comprises 3.8 μg/mL of the influenza antigen in carbonate buffer, pH 9.6 (Sigma Chemical Company). The antigen is allowed to coat the surface of the plate by incubation for about 1 hour at 37° C. Subsequently, the plates are blocked with a blocking solution, e.g., phosphate buffered saline with TWEEN™ 20 (PBS-TW20) and 5% (w/v) non-fat dry milk. The plate is incubated for an additional 2 hours at 37° C. with the blocking buffer. The plate surfaces are then washed with PBS-TW20 at least twice. At this point serum samples of the subject, e.g., mouse, to which the intradermal vaccine formulation of the invention has been administered are assayed. The primary antibody, e.g., the antibody in the serum, is allowed to incubate with the coated and blocked plates for 1 hour at 37° C. The plates are washed 3 times with PBS-TW20 and a cocktail of anti-mouse horseradish peroxidase conjugate is added. The HRP secondary antibody cocktail is allowed to incubate on the plates for an additional hour at 37° C. The plates are washed and a TMB substrate is added for color development. The color is allowed to develop for 30 minutes in the dark. Color development is stopped by the addition of 0.5 M sulfuric acid. Plates are read at 450 nm, e.g., on a TECAN SUNRISE Plate reader.

In another specific embodiment, when the vaccine formulation comprises an influenza antigen any method known in the art for the detection and/or quantitation levels of antibody with hemagglutination activity are encompassed within the invention. The hemagglutination inhibition assays are based on the ability of influenza viruses to agglutinate erythrocytes and the ability of specific HA antibodies to inhibit agglutination. Any of the hemagglutination inhibition assays known in the art are encompassed within the methods of the inventions, such as those disclosed in Newman et al., 1997, *Mechanism of Aging & Development*, 93: 189-203; Kendal et al., 1982, in *Concepts and Procedures for Laboratory-based Influenza Surveillance*, Atlanta: CDC, B17-35; all of which are incorporated herein by reference in their entirety.

An exemplary procedure is as follows: Inoculums are administered intramusclularly or intradermally to a subject (mouse or guinea pig), and sera from the subject are collected and used as test samples. Fresh cRBC reagent is prepared daily. Sodium Chloride solution (0.9%) is added to wells of a Falcon® Non-Tissue Culture Treated Plate, 96 well, U-Bottom with Low Evaporation Lid. Viral lysate stock (8 HA/50 μl) is added to wells. Appropriate volume of test serum previously heat-inactivated for 10 minutes at 56° C. is added to a single row or column of "start wells," and a serial dilution is performed by transferring 50 μl of the serum dilution from the "start wells" into the next well, creating a 1:2 dilution. When completed, wells contain a serial serum dilution and a constant amount of viral lysate antigen, being 4HA per well. cRBC reagent (0.5%, 50 μl) is added to each well, including negative control wells, which contain no HA. The assay is allowed to incubate for 45 minutes at room temperature, ensuring that the plate is not jostled. For determination, plates are tilted at a 70-degree angle for 5 minutes, and viewed on a light box.

5.9 Prophylactic and Therapeutic Uses

The invention provides methods of treatment and prophylaxis which involve administering an dermal vaccine formulation of the invention (including intradermal and epidermal vaccine formulations) to a subject, preferably a mammal, and most preferably a human for treating, managing or ameliorating symptoms associated with a disease or disorder, especially an infectious disease or cancer. The subject is preferably a mammal such as a non-primate, e.g., cow, pig, horse, cat, dog, rat, and a primate, e.g., a monkey such as a Cynomolgous monkey and a human. In a preferred embodiment, the subject is a human.

The invention encompasses a method for immunization and/or stimulating an immunological immune response in a subject comprising intradermal delivery of a single dose of an intradermal vaccine formulation of the invention to a subject, preferably a human. In some embodiments, the invention encompasses one or more booster immunizations. The intradermal vaccine formulation of the invention is particularly effective in stimulating and/or upregualting an antibody response to a level greater than that seen in conventional vaccine formulations and administration schedules. For example, an intradermal vaccine formulation of the invention may lead to an antibody response comprising generations of one or more antibody classes, such as IgM, IgG, and/or IgA.

The invention encompasses a method for immunization and/or stimulating an immunological immune response in a subject comprising epidermal delivery of a single dose of an epidermal vaccine formulation of the invention to a subject, preferably a human.

Most preferably, the dermal vaccine formulations of the invention stimulate a systemic immune response that protects the subject from at least one pathogen. The dermal vaccine formulations of the invention may provide systemic, local, or mucosal immunity or a combination thereof.

5.9.1 Target Diseases

The invention encompasses dermal vaccine delivery systems including epidermal and intradermal delivery systems to treat and/or prevent an infectious disease in a subject preferably a human. Infectious diseases that can be treated or prevented by the methods of the present invention are caused by infectious agents including, but not limited to, viruses, bacteria, fungi protozoa, helminths, and parasites.

Examples of viruses that have been found in humans and can be treated by the vaccine delivery systems of the invention include, but are not limited to, Retroviridae (e.g., human immunodeficiency viruses, such as HIV-1 (also referred to as HTLV-III, LAV or HTLV-III/LAV, or HIV-III; and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (e.g., hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, e.g., Hepatitis C); Norwalk and related viruses, and astroviruses.

Retroviruses that results in infectious diseases in animals and humans and can be treated and/or prevented using the delivery systems and methods of the invention include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents.

Bacterial infections or diseases that can be treated or prevented by the methods of the present invention are caused by bacteria including, but not limited to, bacteria that have an intracellular stage in its life cycle, such as mycobacteria (e.g., *Mycobacteria tuberculosis, M. bovis, M. avium, M. leprae*, or *M. africanum*), rickettsia, mycoplasma, chlamydia, and legionella. Other examples of bacterial infections contemplated include but are not limited to infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species. Specific examples of infectious bacteria include but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia*, and *Actinomyces israelli*.

Fungal diseases that can be treated or prevented by the methods of the present invention include but not limited to aspergilliosis, crytococcosis, sporotrichosis, coccidioidomycosis, paracoccidioidomycosis, histoplasmosis, blastomycosis, zygomycosis, and candidiasis.

Parasitic diseases that can be treated or prevented by the methods of the present invention including, but not limited to, amebiasis, malaria, leishmania, coccidia, giardiasis, cryptosporidiosis, toxoplasmosis, and trypanosomiasis. Also encompassed are infections by various worms, such as but not limited to ascariasis, ancylostomiasis, trichuriasis, strongyloidiasis, toxoccariasis, trichinosis, onchocerciasis. filaria, and dirofilariasis. Also encompassed are infections by various flukes, such as but not limited to schistosomiasis, paragonimiasis, and clonorchiasis. Parasites that cause these diseases can be classified based on whether they are intracellular or extracellular. An "intracellular parasite" as used herein is a parasite whose entire life cycle is intracellular. Examples of human intracellular parasites include *Leishmania* spp., *Plasmodium* spp., *Trypanosoma cruzi, Toxoplasma gondii, Babesia* spp., and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at least one obligate intracellular stage in their life cycles. This latter category of parasites includes *Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

The invention also encompasses dermal vaccine formulations to treat and/or prevent cancers, including, but not limited to, neoplasms, tumors, metastases, or any disease or disorder characterized by uncontrolled cell growth. For example, but not by way of limitation, cancers and tumors associated with the cancer and tumor antigens listed supra may be treated and/or prevented using the dermal vaccine formulations of the invention.

6. EXAMPLES 6.1 Preparation of Stock Solutions of PLURONICS® and/or Mucoadhesives and Determination of Their Geling Properties PLURONIC® F127: PLURONIC® F127 (herein referred to as F127) was obtained from BASF Corporation Mount Olive, N.J. In preliminary experiments, a 20% (w/v) of F127 formed a gel at 37° C. Accordingly, enough F127 was placed in a weigh boat to prepare a 20% (w/v) stock solution. Tissue culture grade water, which is sterile and contains low amounts of endotoxin was used to hydrate the F127. The mixture was stirred on ice until the solution was clear and the pH was adjusted to 7.2 with dilute hydrochloric acid. The solution was placed in a 37° C. water bath where the solution immediately formed a gel.

PLURONIC® F127 and a bioadhesive: A clear solution (pH 7.2) comprising F127 (about 10% w/v) and a mucoadhesive was provided. The solution was then filtered through a 0.2 micron Gelman Acrodisc PF Syringe Filter #4187. The solution was placed in a 37° C. water bath where the solution thickened significantly as visually observed.

Gelatin: Gelatin was derived from bovine skin (Sigma Chemical Company, Catalog G9391) and contained low amounts of endotoxin. Enough gelatin powder was dispensed into a weigh boat to prepare a 0.5% (w/v) stock solution in tissue culture grade water; the pH was adjusted to 7.2 and sterile filtered through a 0.2 micron Gelman Acrodisc PF Syringe Filter #4187.

Methylcellulose: Methylcellulose was obtained from Sigma Chemical Company, Catalog number M-0555. Enough powder was dispensed into a weigh boat to prepare a 1.375% (w/v) stock in tissue culture grade water; the pH was adjusted to 7.2 and sterile filtered through a 0.2 micron Gelman Acrodisc PF Syringe Filter #4187.

PLURONIC® F127 and carboxymethylcellulose: Carboxymethylcellulose was obtained from Sigma Chemical Company (Cat C-9481). A 2.5% (w/v) solution was prepared using tissue culture grade water; the pH was adjusted to 7.2 and sterile filtered through a 0.2 micron Gelman Acrodisc PF Syringe Filter #4187. A 20% w/v solution of F127 was prepared using tissue culture grade water; and mixed with the carboxymethylcellulose solution; the mixture was stirred on ice until clear; the pH was adjusted to 7.2 and sterile filtered through a 0.2 micron Gelman Acrodisc PF Syringe Filter #4187.

6.2 Preparation of Fluzone Inoculum for the Initial Screening

PLURONIC® F127: Approximately one hour prior to immunization, the following was dispensed into a Nunc vial for mixing; 125 µL of FLUZONE and 375 µL of the F127 stock solution as prepared in Section 6.1. The final concentration of F127 in the solution for immunization (the inoculum) was about 15%. The inoculum readily thickened when placed in a 37° C. water bath, however it did not form a gel. Each animal received 100 µl of the inoculum thereby receiving $\frac{1}{10}^{th}$ of the human pediatric dose.

PLURONIC® F127 and a bioadhesive: Approximately one hour prior to immunization, the following was dispensed into a Nunc vial for mixing; 125 µL of FLUZONE and 375 µL of the stock solution as prepared in Section 6.1. The final concentration of F127/mucoadhesive in the solution for immunization (the inoculum) is about 75% (v/v) of the initial stock received by vendor. The inoculum readily thickened when placed in a 37° C. water bath, however it did not form a gel. Each animal received 100 µl of he inoculum thereby receiving $\frac{1}{10}^{th}$ of the human pediatric dose.

Gelatin: Approximately one hour prior to immunization, the following was dispensed into a Nunc vial for mixing; 125 µL of FLUZONE and 50 µL of the stock solution as prepared in Section 6.1, and 325 µL of sterile Hanks buffered saline. The final inoculum was about 0.0625% w/v gelatin, whereby the FLUZONE component contributed 0.0125% (w/v) and the Sigma Gelatin supplement was 0.05% w/v. Each animal received 100 µl of the inoculum thereby receiving $\frac{1}{10}^{th}$ of the human pediatric dose.

Methylcellulose: Approximately one hour prior to immunization, the following was dispensed into a Nunc vial for mixing; 175 µL of FLUZONE and 280 µL of the stock solution as prepared in Section 6.1, and 245 µL of sterile Hanks buffered saline. The final inoculum was about about 0.55% w/v methylcellulose. Each animal received 100 µl of the inoculum thereby receiving $\frac{1}{10}^{th}$ of the human pediatric dose.

PLURONIC® F127 and carboxymethylcellulose: Approximately one hour prior to immunization, the following was dispensed into a Nunc vial for mixing; 175 µL of FLUZONE and 262.5 µL of the F127 stock solution as prepared in Section 6.1.1, and 262.5 µL of the carboxymethylcellulose stock solution as prepared in Section 6.1.1. The final inoculum was about about 7.5% w/v F127 and 0.9% w/v carboxymethylcellulose. Each animal received 100 µL of the inoculum thereby receiving $\frac{1}{10}^{th}$ of the human pediatric dose Control Formulation: The control FLUZONE formulation comprised 125 µL of FLUZONE in 375 µL of sterile Hanks buffered saline.

6.2.1 Preparation of Fluzone Inoculum for Determining End-Point Titers

Methylcellulose: Approximately one hour prior to immunization, the following was dispensed into a Nunc vial for mixing; 175 µL of FLUZONE and a volume from the methylcellulose stock to yield a final inoculum as being 0.18% w/v methylcellulose. Each animal received 100 µl of the inoculum thereby receiving $\frac{1}{10}^{th}$ of the human pediatric dose Fluzone dose.

6.2.2 Preparation of Fluzone Inoculum for Draize Scoring

Methylcellulose: One ml of inoculum was prepared whereby the Fluzone component represented 50% by volume and the final inoculum concentration was 0.18% w/v methylcellulose. A Yorkshire pig received 3 separate 200 ul blebs of the Fluzone-methylcellulose inoculum.

6.3 Intradermal Administration of Fluzone Inoculum Into Mice

The FLUZONE formulations as described and prepared above were delivered to the intradermal compartment of Balb/c mice using an intradermal Mantoux method. The Balb/c mice used were between 4 and 8 weeks of age and were obtained from Charles River Laboratoreis. The inoculum preparations were administered within 1 hour of preparation. The inoculum preparations in each case were drawn up into a 1 mL latex free syringe with a 20 gauge needle. After the syringe was loaded, it was replaced with a 30 gauge needle for intradermal administration. The skin of the mice was approached at the most shallow possible angle with the bevel of the needle pointing upwards, and the skin pulled tight. The injection volume was then pushed in slowly over 5-10 seconds forming the typical "bleb" and the needle was subsequently slowly removed.

Only one injection site was used. The injection volume was no more than 100 µL, due in part, to the fact that a larger injection volume may increase the spill over into the surrounding tissue space, e.g., the subcutaneous space. The lower to mid back of the mice were used for injection. The mice were dry shaved just prior to injection with a Conair Electric Shaver.

Approximately fifteen minutes prior to receiving the FLU-ZONE injection each animal received an intraperitoneal injection of Ketamine/Xylazine/Acepromazine cocktail for sedation.

Animals were monitored for local and systemic indications of toxicity immediately after, 24 hours post administration and again at 3 weeks post administration. No signs of local or systemic toxicity were observed with either of the formulations described above.

6.4 Intradermal Administration of Fluzone Inoculum Into Swine

Yorkshire pigs were obtained from Archer Farms with weights ranging from 20-30 kilograms. Yorkshires were anesthetized with Isoflurane for the procedure. The injection site was dry-shaved and cleansed before delivery. Each animal received three replicated administrations with a 31gauge×1.5 mm hollow needle.

6.5 Determination of Fluzone Efficacy

In order to determine the antibody response to FLUZONE formulations as prepared supra the following ELISA assay was used. An Influenza APR384 purified/inactivated antigen at a concentration of 2 mg/mL (from Charles River SPAFAS) in carbonate buffer, pH 9.6 (Sigma Chemical Company), was used as the test antigen. The test antigen was used to coat a microtitre plate (96-well ImmunoPlate™ with MaxiSorp™ Surface). The antigen was allowed to coat the surface of the plate by incubation for about 1 hour at 37° C. Subsequently, the plates were blocked with a blocking solution, phosphate buffered saline with TWEEN™ 20 (PBS-TW20) and 5% (w/v) non-fat dry milk. The plate was incubated for an additional 2 hours at 37° C. with the blocking buffer. The plate surfaces were then washed with PBS-TW20 twice.

Serum from each mouse within a test or control group was pooled and the pooled serum was assayed at a 1:123 and 1:370 dilutions. The primary antibody was allowed to incubate with the coated and blocked plates for 1 hour at 37° C. The plates were washed 3 times with PBS-TW20 and a cocktail of anti-mouse horseradish peroxidase conjugate was added. The HRP conjugate pool consisted of 5 conjugates: Sigma A4416, Southern Biotech 1090-05, Southern Biotech 1070-05, Southern Biotech 1080-05 and Southern Biotech 1100-05. All conjugates were present in the final cocktail at a 1:15,000 dilution. The HRP secondary antibody cocktail was allowed to incubate on the plates for an additional hour at 37° C. The plates were washed and a TMB substrate was added for color development. The color was allowed to develop for 30 minutes in the dark. Color development was stopped by the addition of 0.5 M sulfuric acid. Plates were read at 450 nm on a TECAN SUNRISE Plate reader.

The ELISA used to determine titer by end-point was performed in the same manner as that described above, although with more dilutions (1:100, 1:200, 1:400, 1:800, 1:1600, 1:3200, 1:6400). The titers values plotted in FIG. 6 were determined by finding the intersection of the interpolated data curve with the interpolated curve for 3× the non-immune value.

Results

FIGS. 1-5 show serum antibody response of the various FLUZONE preparations as described above following FLUZONE vaccination of mice. Serum was obtained between 20 and 22 days post vaccination. In each case, serum response at 1:123 dilution to the influenza antigen was assessed using the ELISA assay described above. As shown in FIGS. 1-5, FLUZONE preparations that contained PLURONIC® F127, gelatin, methylcellulose, and a combination of carboyxmethylcellulse and F127, resulted in an enhanced antibody serum response as compared to FLUZONE alone.

Most significantly, the enhanced antibody response with the inoculum preparations described above were compatible with the intradermal compartment, since no negative skin results were observed with any of the formulations described. Additionally, the molecules used in the intradermal influenza vaccine formulations of the invention have been approved for clinical use, e.g., methylcellulose and PLURONIC® F127, indicating that the vaccine formulations described may be used in humans.

Figure 6:
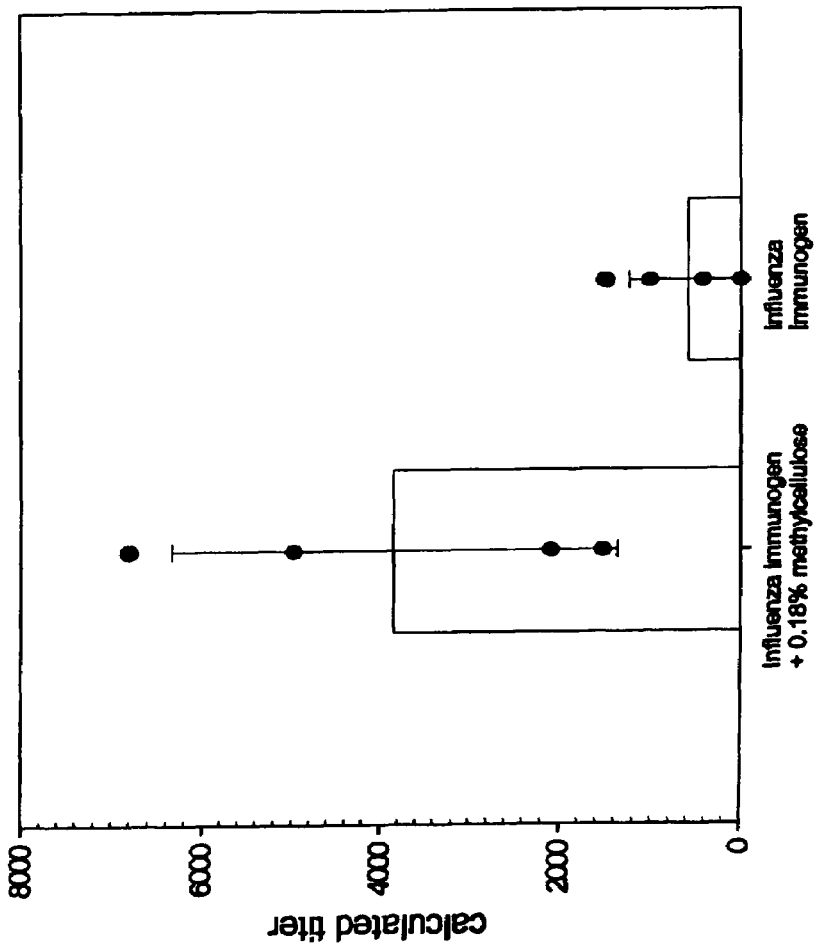

FIG. 6 shows the serum antibody response of the various FLUZONE preparations as described above following FLUZONE vaccination of mice. Where the data presented in FIGS. 1-5 was generated by assaying pools of serum from animals within a particular test or control group. FIG. 6 data provides individual animal responses. P-values less than 0.05 indicate significant change in population mean titer for animals receiving the methylcellulose supplemented Fluzone.

FIG. 7 shows inoculum comprising methylcellulose and methylcellulose with Fluzone as being compatible with the dermal tissue, as administration sites were monitored at 1 hour, 6 hours and 24 hours post delivery.

6.6 Preparation of Cocktails

Prior to preparation of various formulations, the pH of all excipient stock solutions were checked for a neutral pH, i.e., 7.0-7.4. The pH of the solutions was adjusted to neutral as necessary using dilute HCl or NaOH. All excipient stock solutions were sterile filtered through a 0.2 micron Gelman Acrodisc PF syringe filter #4187.

Aventis Fluzone® containing New Calcdonia A Strain, Panama A strain, and Hong Kong B Strain, as commercially available, was used for inoculums. Test inoculums were prepared by adding appropriate amount of Aventis Fluzone® vaccine, and the excipients at a final concentration as denoted in the table below. Sodium chloride at 9% w/v was used to adjust the volume. A control inoculum was prepared by adding sodium chloride to the appropriate amount of respective Fluzone™ to yield the same final volume as the inoculums. 4. Excipient Combination Concentration LUTROL® F127 5% w/v and Methylcellulose 0.18% w/v LUTROL® F127 5% w/v and Sorbitol 5% w/v LUTROL® F127 5% w/v and Urea 0.20% w/v Gelatin 0.225% w/v and Methylcellulose 0.18% w/v LUTROL® 5% w/v and Gelatin 0.225% w/v.

| Excipient Combination | Concentration |
|---|---|
| Lutrol F127 | 5% w/v |
| and | |
| Methylcellulose | 0.18% w/v |
| Lutrol F127 | 5% w/v |
| and | |
| Sorbitol | 5% w/v |
| Lutrol F127 | 5% w/v |
| and | |
| Urea | 0.2% w/v |

-continued

| Excipient Combination | Concentration |
|---|---|
| Gelatin | 0.225% w/v |
| and | |
| Methylcellulose | 0.18% w/v |
| Lutrol | 5% w/v |
| and | |
| Gelatin | 0.225% w/v |

6.6.1 Preparation of Chicken Red Blood Cells

Chicken Red Blood Cells (cRBC, 5 ml packed) were obtained from Charles River Laboratories (Cat. #S8776). cRBC was equally distribuited into four Flacon® Blue Max™ 50 ml polyethylene conical tubes, and centrifuged at 1500 rpm for 5-7 minutes at 4° C. Shipping buffer was removed from cRBC. Sodium chloride solution (0.9%) was added in 5 ml increments onto the cRBC pellet, and the pellet was resuspended. Combining the resuspended pellets from two of the first-wash, the volume was adjusted to 45 ml with sodium chloride solution (0.9%). The mixture was centrifuged at 1500 rpm for 5-7 minutes at 4° C., and the supernatant was discarded. Again, sodium chloride solution (0.9%) was added in 5 ml increments onto the cRBC pellet, and the pellet was resuspended. The resuspended pelletes from the two second-washs were combined, and the volume was adjusted to 45 ml with sodium chloride solution (0.9%). The mixture was centrifuged at 1500 rpm for 5-7 minutes at 4° C., and the supernatant discarded. Ten percent cRBC solution was prepared by resuspending the final pellet in ten times the original volume.

6.6.2 Determination of Hemaglutinin (HA) Content in Concentrated Influenza Viral Lysate Stocks In order to perform an HA Inhibition Assay, the HA titer of the viral lysate stock must be determined. The HA Inhibition Assay requires a viral lysate screening stock at a concentration of 8HA per 50 µl of solution. Determination of the viral lysate HA titer allows for proper dilution of the viral lysate stock for the HA Inhibition Assay.

Fresh 0.5% cRBC reagent was prepared daily. Sodium chloride solution (0.9%, 50 µl) was distributed into the wells of a Falcon® Non-Tissue Culture Treated Plate, 96 well, U-Bottom with Low Evaporation Lid. Viral Lysate (100 µl) was distributed into a set of wells, which did not contain the sodium chloride solution. Half of the viral lysate (50 µl) was then into the next well (containing 50 µl sodium chloride), creating a 1:2 dilution. This serial dilution for both replicates was continued through the last well containing the sodium chloride. cRBC solution (0.5%, 50 µl) was distributed into the wells. Wells with no viral lysate served as negative controls. The assay was allowed to incubate for 45 minutes at room temperature, ensuring that the plate is not jostled.

If there is too little viral lysate in the dilution to ensure hemagglutination, the cRBC's in the well settle at the bottom of the well due to gravity. Any well containing partial or total settling of the cRBC's to the bottom of the well is negative. The last well with complete suspension of the cRBC's in the solution was determined for the HA titer of the viral lysate.

6.6.3 Titration of the Influenza Antigen Working Stock to Verify HA Content

Prior to performing the HA Inhibition Assay, the HA titer of the viral lysate working stock must be validated. The working stock should be 8HA per 50 µl. Fresh 0.5% cRBC reagent was prepared daily. Predetermined dilution of the viral lysate to yield the presumptive 8 HA working stock was performed. Dilutions were prepared with sodium chloride solution (0.9%).

Sodium chloride solution (0.9%, 50 µl) was distributed into the wells of a Falcon® Non-Tissue Culture Treated Plate, 96 well, U-Bottom with Low Evaporation Lid. The presumptive 8HA/50 µl working stock (100 µl) was distributed into a single row or column of "start wells." Half volume (50 µl) of the stock was transferred from the start well to a second well, creating a 1:2 dilution. Using the 1:2 dilution, repeat the process and continue until the dilution series was complete. A complete dilution set had wells containing 0.0625 HA to 8HA. cRBC reagent (0.5%, 50 µl) was distributed into each well containing some level of HA, and the assay was allowed to incubate for 45 minutes at room temperature, ensuring that the plate is not jostled.

If too little viral lysate HA in the dilution to ensure hemagglutination, the cRBC's in the well settle at the bottom of the well due to gravity. Any well containing partial or total settling of the cRBC's to the bottom of the well is negative. The last well with complete suspension of the cRBC's in the solution is the HA titer of the viral lysate stock. If the stock was truly an 8HA per 50 µl stock, then upon retitration, the last positive wells contained 1HA.

6.6.4 Mesurement of HA Specific Antibody Titer by HAI

Inoculums were administered intramusclularly or intradermally to a subject (mouse or guinea pig), and sera from the subject were collected and used as test samples. Fresh cRBC reagent was prepared daily. Sodium Chloride solution (0.9%) was added to wells of a Falcons® Non-Tissue Culture Treated Plate, 96 well, U-Bottom with Low Evaporation Lid. Viral lysate stock (8 HA/50 µl) was added to wells. Appropriate volume of heat-inactivated (10 minutes 56° C.) serum was added to a single row or column of "start wells," and a serial dilution was performed by transferring 50 µl of the serum dilution from the "start wells" into the next well, creating a 1:2 dilution. When completed, wells contained a serial serum dilution and a constant amount of viral lysate antigen, being 4HA per well. cRBC reagent (0.5%, 50 µl) was added to each well, including negative control wells, which contained no HA. The assay was allowed to incubate for 45 minutes at room temperature, ensuring that the plate is not jostled. For determination, plates were tilted at a 70-degree angle for 5 minutes, and viewed on alight box.

6.7 Results 6.7.1 LUTROL® and Methylcellulose

In another set of experiments, the immune responses obtained from the same antigen, where the antigen was: 1) untreated and delivered IM; 2) untreated and delivered ID; and 3) reformulated with LUTROL® and methylcellulose and delivered ID, were examined. As shown in FIG. 17, the ID administration of the antigen reformulated with LUTROL® and methylcellulose elicited a higher immune response than either of the untreated antigens. These results clearly show that the combination of LUTROL® and methylcellulose exhibits an adjuvant activity when administered to a subject together with an immunogen.

The adjuvant activity exhibited by the combination of LUTROL® and methylceluose was unaffected where individual stain antigens were used (FIGS. 18-20), regardless of whether they were administered to Balb/c mice (FIGS. 18 and 19) or guinea pigs (FIG. 20). In addition, the combination of LUTROL® and methylcellulose exhibited the adjuvant activity in broad ranges of LUTROL® concentration, in particular, where the concentration of LUTROL® was 15% (FIG. 18) or 5% (FIG. 19).

6.7.2 LUTROL® and Urea

Untreated Aventis Fluzone® containing trivalent test antigen (50 μl dose) was administered intramusclulary to a first set of guinea pigs, and the same antigen reformulated with LUTROL® and urea was administered intrademally to another set of guinea pigs. From the comparison of immune responses obtained from the two sets (FIG. 21), it was shown that the antigen reformulated with LUTROL® and urea elicited a higher immune response than the untreated antigen.

In another set of experiments, the immune responses obtained from the following were compared: 1) untreated New Caledonia rHA, as commecially available, delivered ID, and the same antigen reformulated with LUTROL® and urea, delivered ID (panel 1); 2) untreated Panama rHA, as commercially available, delivered IM, and the same antigen reformulated with LUTROL® and urea, delivered ID (panel 2); and 3) untreated Hong Kong B strain antigen, as commercially available, delivered IM, and the same antigen reformulated with LUTROL® and urea, delivered ID (panel 3). As shown in FIG. 22, all of the reformulated antigens elicited higher immune responses than untreated antigen, regardless of the type of antigens used. These results show that LUTROL®-urea is an effective combination that can be used as adjuvant in immunogenic compositions.

6.7.3 Gelatin and Methylcellulose

Untreated Aventis Fluzone® containing trivalent test antigen (50 μl dose) was administered to guinea pigs either intramusclulary or intradermally. The immune responses obtained from the guinea pigs were compared to the response obtained from the same antigen reformulated with gelatin and methylcellulose, administered intradermally to guinea pigs. As shown in FIG. 23, the antigen reformulated with gelatin and methylcellulose elicited a higher immune response than the untreated antigen. The results show that the combination of gelatin and methylcellulose exhibits an adjuvant activity, when administered to a subject together with an immunogen.

6.7.4 LUTROL® and Sorbitol

Untreated Aventis Fluzone® containing trivalent test antigen (50 μl dose) was administered to guinea pigs either intramusclulary or intradermally. The immune responses obtained from the guinea pigs were compared to the response obtained from the same antigen reformulated with LUTROL® and sorbitol, administered intradermally to guinea pigs. As shown in FIG. 24, the antigen reformulated with LUTROL® and sorbitol elicited a higher immune response than the untreated antigen, as determined by HAI assay (panel 1) and ELISA (panel 2). The results show that the combination of LUTROL® and sorbitol exhibits an adjuvant activity, when administered to a subject together with an immunogen.

6.8 Draize Scoring of the Excipients Combinations

To assess the skin irritation that may be caused by the combination of excipients used in the compositions of the invention, Draize scoring tests were performed following the administration of certain excipients combinations to either Yorkshire swine or Hartley guinea pigs. A typical scoring scales are shown in Table 1 below.

TABLE 1

Draize Scoring
Key to interpreting skin reactions - Draize Scoring

| Erythema Score | | Edema Score | |
|---|---|---|---|
| No erythema | 0 | No edema | 0 |
| Slight erythema (barely perceptible) | 1 | Slight edema (barely perceptible) | 1 |
| Well-defined erythema | 2 | Well-defined edema | 2 |

TABLE 1-continued

Draize Scoring
Key to interpreting skin reactions - Draize Scoring

| Erythema Score | | Edema Score | |
|---|---|---|---|
| Moderate to severe | 3 | Moderate to severe | 3 |
| Severe erythema (beet redness to administration sight, injury by depth | 4 | Sever edema (extending beyond the site | 4 |

Erythema Draize scores of various combinations were as follows:

TABLE 2

Lutrol (10%) and Urea (5%), 200 μl per Injection: Combination was delivered without vaccine to swine using 31 guage 1.0 mm, 1.5 mm, or 2.0 mm needles

| Needle | 1 Hour After Injection | | | 24 Hours After Injection | | |
|---|---|---|---|---|---|---|
| 1.0 mm | 1 | 1+ | 1 | 1 | 1 | 1 |
| 1.5 mm | 0 | 1 | 1+ | 1 | 0 | 1+ |
| 2.0 mm | 0 | 0 | 0 | 0 | 0 | 0 |

TABLE 3

Various Combinations, 50 μl per Injection: Specified combinations were delivered without vaccine to guinea pigs using 34 guage, 1.0 mm needles

| Combinations | Immediately After Injection | | 1 Hour After Injection | | 24 Hours After Injection | |
|---|---|---|---|---|---|---|
| Lutrol (5%) + methylcellulose (0.18%) | 1 | 1 | 1 | 1 | 1+ | 1 |
| Lutrol (5%) + Urea (0.2%) | 1 | 1 | 0 | 0 | 0 | 0 |
| Lutrol (5%) + Sorbitol (5%) | 1 | 1 | 0 | 0 | 1+ | 1+ |
| Gelatin (0.225%) + methylcellulose (0.18%) | 1 | 1 | 0 | 0 | 1 | 0 |

TABLE 4

Various Combinations, 200 μl per Injection: Specified combinations were delivered without vaccine to swine using 34 guage, 1.5 mm needles

| Combinations | 1 Hour After Injection | | | 24 Hours After Injection | | |
|---|---|---|---|---|---|---|
| Lutrol (5%) + Methylcellulose (0.18%) | 2 | 2 | 2 | 0 | 0 | 0 |
| Lutrol (5%) + Urea (0.2%) | 1 | 2 | 1+ | 0 | 0 | 0 |
| Lutrol (5%) + Sorbitol (5%) | 0 | 0 | 1+ | 0 | 0 | 0 |
| Gelatin (0.225%) + Methylcellulose (0.18%) | 1 | 1 | 1 | 0 | 0 | 0 |
| Lutrol (5%) + Gelatin (0.225%) | 0 | 0 | 0 | 0 | 1 | 1+ |

As shown in Tables 2-4, none of the combinations tested exhibited a serious skin irritation when administered to a subject. The results suggest that the excipients combinations of the invention are also safe for the use in patients.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout this application various publications are cited. Their contents are hereby incorporated by reference into the present application in their entireties for all purposes.

What is claimed is:

1. An immunogenic composition, comprising an immunogenic or antigenic agent and a cocktail of at least two agents, wherein the first agent is selected from the group consisting of poloxamer 407, poloxamer 188, poloxamer 338, poloxamer 237, poloxamer 231, poloxamer 282, poloxamer 331, poloxamer 401, poloxamer 402, and poloxamer 461, and the second agent is urea, so that the cocktail enhances the immune response against the antigenic or immunogenic agent upon administration of the immunogenic composition to a subject.

2. The immunogenic composition of claim 1, wherein the concentration of the first agent used in the composition is from about 1% w/v to about 25% w/v of the composition.

3. The immunogenic composition of claim 1, wherein the concentration of the first agent used in the composition is from about 3% w/v to about 15% w/v of the composition.

4. The immunogenic composition of claim 1, wherein the concentration of the first agent used in the composition is from about 5% w/v to about 10% w/v of the composition.

5. The immunogenic composition of claim 1, wherein the concentration of urea used in the composition is from about 0.01% w/v to about 10% w/v of the composition.

6. The immunogenic composition of claim 1, wherein the concentration of urea used in the composition is from about 0.1% w/v to about 5% w/v of the composition.

7. The immunogenic composition of claim 1, wherein the concentration of urea used in the composition is from about 0.2% w/v to about 1% w/v of the composition.

8. The immunogenic composition of claim 1, wherein the concentration of the first agent used in the composition is about 5% w/v and the concentration of urea used in the composition is about 0.2% w/v.

9. The immunogenic composition of claim 1, wherein the first agent is poloxamer 407.

10. The immunogenic composition of claim 1, wherein the first agent is poloxamer 188.

11. The immunogenic composition of claim 1, wherein the first agent is poloxamer 338.

12. The immunogenic composition of claim 1, wherein the first agent is poloxamer 237.

13. The immunogenic composition of claim 1, wherein the first agent is poloxamer 231.

14. The immunogenic composition of claim 1, wherein the first agent is poloxamer 282.

15. The immunogenic composition of claim 1, wherein the first agent is poloxamer 331.

16. The immunogenic composition of claim 1, wherein the first agent is poloxamer 401.

17. The immunogenic composition of claim 1, wherein the first agent is poloxamer 402.

18. The immunogenic composition of claim 1, wherein the first agent is poloxamer 461.

19. An immunogenic composition comprising an immunogenic or antigenic agent, wherein the immunogenic or antigenic agent is a peptide, polypeptide, polypeptide fragment, or polysaccharide, and a cocktail of at least two agents, wherein the first agent is poloxamer 407 and the second agent is urea.

20. The immunogenic composition of claim 19, wherein the concentration of poloxamer 407 used in the composition is from about 1% w/v to about 25% w/v of the composition.

21. The immunogenic composition of claim 19, wherein the concentration of poloxamer 407 used in the composition is from about 3% w/v to about 15% w/v of the composition.

22. The immunogenic composition of claim 19, wherein the concentration of poloxamer 407 used in the composition is from about 5% w/v to about 10% w/v of the composition.

23. The immunogenic composition of claim 19, wherein the concentration of urea used in the composition is from about 0.01% w/v to about 10% w/v of the composition.

24. The immunogenic composition of claim 19, wherein the concentration of urea used in the composition is from about 0.1% w/v to about 5% w/v of the composition.

25. The immunogenic composition of claim 19, wherein the concentration of urea used in the composition is from about 0.2% w/v to about 1% w/v of the composition.

26. The immunogenic composition of claim 19, wherein the immunogenic or antigenic agent is a peptide.

27. The immunogenic composition of claim 19, wherein the immunogenic or antigenic agent is a polypeptide.

28. The immunogenic composition of claim 19, wherein the immunogenic or antigenic agent is a polypeptide fragment.

29. The immunogenic composition of claim 19, wherein the immunogenic or antigenic agent is a polysaccharide.

* * * * *

UNITED STATES PATENT AND TRADEMARK OFFICE
CERTIFICATE OF CORRECTION

| | | |
|---|---|---|
| PATENT NO. | : 7,588,774 B2 | Page 1 of 1 |
| APPLICATION NO. | : 11/006422 | |
| DATED | : September 15, 2009 | |
| INVENTOR(S) | : Campbell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this
Eighth Day of February, 2011

David J. Kappos
*Director of the United States Patent and Trademark Office*